US008738142B2

(12) United States Patent
Palermo et al.

(10) Patent No.: US 8,738,142 B2
(45) Date of Patent: May 27, 2014

(54) ELECTRICAL STIMULATION DEVICE AND METHOD FOR THE TREATMENT OF NEUROLOGICAL DISORDERS

(75) Inventors: Francis X. Palermo, Lafayette, CO (US); J. Chris Castel, Reno, NV (US)

(73) Assignee: Accelerated Care Plus Corp., Reno, NV (US)

( * ) Notice: Subject to any disclaimer, the term of this patent is extended or adjusted under 35 U.S.C. 154(b) by 0 days.

(21) Appl. No.: 13/113,389

(22) Filed: May 23, 2011

(65) Prior Publication Data
US 2011/0224753 A1 Sep. 15, 2011

Related U.S. Application Data

(62) Division of application No. 11/711,285, filed on Feb. 27, 2007, now Pat. No. 7,949,403.

(51) Int. Cl.
*A61N 1/18* (2006.01)

(52) U.S. Cl.
USPC .............................................. 607/46; 607/72

(58) Field of Classification Search
USPC ................ 607/2, 45–46, 70–75, 115
See application file for complete search history.

(56) References Cited

U.S. PATENT DOCUMENTS

| 3,817,254 | A |   | 6/1974  | Maurer |
|---|---|---|---|---|
| 3,902,502 | A |   | 9/1975  | Liss et al. |
| 4,844,075 | A |   | 7/1989  | Liss et al. |
| 5,109,847 | A |   | 5/1992  | Liss et al. |
| 5,540,736 | A |   | 7/1996  | Haimovich et al. |
| 5,562,718 | A | * | 10/1996 | Palermo ........................ 607/46 |
| 5,834,051 | A |   | 11/1998 | Woloszko et al. |
| 6,132,361 | A |   | 10/2000 | Epstein et al. |
| 6,405,079 | B1 |   | 6/2002  | Ansarinia |
| 6,418,344 | B1 |   | 7/2002  | Rezai et al. |
| 6,425,852 | B1 |   | 7/2002  | Epstein et al. |
| 6,526,318 | B1 |   | 2/2003  | Ansarinia |
| 6,567,702 | B1 |   | 5/2003  | Nekhendzy et al. |
| 6,572,594 | B2 |   | 6/2003  | Satterfield et al. |
| 6,904,322 | B2 |   | 6/2005  | Katsnelson |
| 7,146,217 | B2 |   | 12/2006 | Firlik et al. |
| 7,151,961 | B1 |   | 12/2006 | Whitehurst et al. |
| 2006/0004422 | A1 |   | 1/2006  | De Ridder et al. |
| 2006/0015153 | A1 | * | 1/2006  | Gliner et al. .................... 607/45 |
| 2006/0161219 | A1 |   | 7/2006  | Mock et al. |
| 2006/0195154 | A1 |   | 8/2006  | Jaax et al. |
| 2006/0241374 | A1 |   | 10/2006 | George et al. |
| 2007/0038252 | A1 |   | 2/2007  | Carroll |
| 2007/0156182 | A1 |   | 7/2007  | Castel et al. |

OTHER PUBLICATIONS

Ardolina et al., *Non-synaptic mechanisms underlie the after-effects of cathodal transcutaneous direct current stimulation of the human brain*, J. Physiology, 568 653-663 (2005); published online Jul. 21, 2005.

* cited by examiner

*Primary Examiner* — Rex R Holmes
(74) *Attorney, Agent, or Firm* — Thomas E. Jurgensen

(57) ABSTRACT

An electrical stimulation system and method for the treatment of neurological disorders is disclosed. In a preferred embodiment, the electrical stimulation system includes channels of electrodes positioned in electrical contact with tissue of a neuromuscular target body region of a patient to provide patterned neuromuscular stimulation to the patient's musculature. In addition, at least one electrode from a channel is positioned in electrical contact with a tissue of the motor control region of the brain. A series of patterned electrical pulses are then applied to the patient through the channels to provide peripheral neuromuscular stimulation, and a direct current is applied transcranially to the brain. Various exemplary embodiments of the invention are disclosed.

14 Claims, 21 Drawing Sheets

ELECTRICAL STIMULATION DEVICE AND METHOD FOR THE TREATMENT OF NEUROLOGICAL DISORDERS

CROSS-REFERENCE TO RELATED APPLICATIONS

This application is a divisional application of U.S. patent application Ser. No. 11/711,285, filed on Feb. 27, 2007, which is hereby incorporated herein by reference.

STATEMENT REGARDING FEDERALLY SPONSORED RESEARCH OR DEVELOPMENT

Not applicable.

FIELD OF THE INVENTION

The present invention is generally directed to the treatment of neurological disorders, and is more specifically directed to an electrical stimulation device and method for applying electrical stimulation, preferably pattered electrical pulses, to one or more channels of electrodes or bifurcated electrodes in accordance with a procedure for treating the neurological disorder along with transcranial electrical stimulation of the brain.

DESCRIPTION OF RELATED ART

There are multiple forms of surface and percutaneous neuromuscular electrical stimulation available for treatment of neurological conditions. One form is patterned neuromuscular stimulation that attempts to replicate the activation patterns of nerves, muscles and the central nervous system including the spine and the brain. These patterns can be created by a plurality of energy input configurations that ultimately produce muscle and nerve activation. The above devices typically produce transient or brief activation bursts which are repeated for a longer period of time.

Direct current stimulation has been shown to be well tolerated in applications to the brain through the skull or cranium. It is described as transcranial direct current stimulation and is accomplished by multiple devices that generate continuous low current ion flow through the skull into the brain tissue. Other forms of brain stimulation involve creating holes in the skull and implanting a variety of energy transmitters.

BRIEF SUMMARY OF THE INVENTION

The present invention is directed to an electrical stimulation system and method for the treatment of neurological disorders. The system combines both neuromuscular electrical stimulation to target body regions and transcranial direct current stimulation in a single treatment regime.

In one aspect, the electrical stimulation system comprises (1) a neuromuscular stimulator adapted to stimulate the sensory and motor nerves of the patient's musculature, such as the muscles of the face, trunk, lower extremities, or upper extremities of the patient combined with (2) a transcranial stimulator adapted to stimulate the regions of the brain associated with sensation and motor control of the patient's musculature. The neuromuscular stimulator and the transcranial stimulator may be contained in a single device or may be separate devices operated by one or more electronic control units.

In another aspect, the electrical stimulation system comprises a neuromuscular simulator having at least one electronic control unit connected to channels of electrodes, such as transcutaneous or percutaneous electrodes. Each channel comprises two electrodes (i.e., a relative positive electrode and a relative negative electrode). The electrodes of a first channel are positioned in electrical contact with tissue of a target region of the patient to stimulate one or more muscles associated with or afflicted by a neurological disorder. The electrodes of a second channel are positioned in electrical contact with tissue that is also associated with or afflicted by the neurological disorder. In many instances, the electrodes of the first and second channels are positioned bilaterally or in electrical contact with the tissue of agonist/antagonist pairs of muscles of the patient. The electronic control unit applies a series of patterned electrical pulses to the patient through the channels of electrodes in accordance with a procedure for treating the neurological disorder.

In addition, the electrical stimulation system comprises electrodes of a third channel and optional fourth channel positioned in electrical contact with the patient's cranium. The electronic control unit (or an electronic control unit in a separate device) applies a transcranial direct current to select areas of the patient's brain through the electrodes in accordance with a procedure for treating the neurological disorder. Typically, the positive electrodes of the third channel and optional fourth channel are placed over the brain region associated with control of the target muscles (e.g. the facial muscles, lower extremities, upper extremities, trunk, etc.) and related brain sensory region, and the negative electrode of the third and optional fourth channel may be placed in a neutral position. For example, the negative electrode may be placed contralaterally over the brain region associated with control of the target muscles(s) on the opposite side of the cranium, which may result in inhibition (not stimulation) of that brain region. Alternatively, the negative electrode may be placed on the prefrontal cortex (i.e., the forehead) or on the patient's opposite shoulder/neck region as the neutral position.

The electrical stimulation system of the present invention is well adapted to rehabilitate and treat the motor control of the major muscles the body, including but not limited to the major muscles of the face, neck, shoulder, back, trunk, arm, forearm, wrist, hand, hip, thigh, lower leg, ankle, and foot.

In a further aspect, the electrical stimulation system and method of the present invention may be used to enhance performance in otherwise normal or uninjured individuals, thus for example to enhance athletic performance.

In yet another aspect, the patient's musculature and brain motor-sensory regions are preferably stimulated in a manner that facilitates movement of the target muscles with limited or no pain in the patient.

Typically, the patient is treated with the electrical simulation system for between ten minutes and two hours, most preferably between 20 minutes and one hour, and still more preferably for about 20 to 40 minutes. Treatment sessions can be repeated as needed.

In one aspect, the neuromuscular patterned stimulation is performed at the same time that the transcranial direct current stimulation is performed on the patient. In another aspect, the method of treatment comprises an initial period of transcranial direct current stimulation only, typically 5, 10, 15, 20, or 30 minutes of constant or pulsed direct current stimulation, followed by simultaneous neuromuscular stimulation and transcranial direct current stimulation. In yet a further aspect, method of treatment comprises an initial period of neuromuscular stimulation only, typically 5, 10, 15, 20, or 30 minutes, followed by simultaneous neuromuscular stimulation and transcranial direct current stimulation.

It is envisioned that the transcranial direct current stimulation lowers the threshold of brain activation and will permit peripheral stimulation to be more effective in the functional reorganization of the brain and its response to stimuli from peripheral activation. Peripheral stimulation activates muscles and nerves. These peripheral nerves send sensory information back to the brain's somatosensory motor centers, activating central patterns or circuit reflexes in the brain.

Patterned Electrical Neuromuscular Stimulation ("PENS")

As discussed above, the present invention is directed to an electrical stimulation system and method which comprises a neuromuscular stimulator having a plurality of channels adapted to stimulate the motor and sensory nerves of the patient's musculature, such as the muscles of the face, trunk, lower extremities, or upper extremities of the patient.

The series of electrical pulses (which can be created from a variety of pulse or wave generators) applied to the channels may comprise a variety of different types of pulse train patterns. For example, a plurality of cycles of a biphasic sequential or overlapping pulse train pattern may be used, in which a first phase of electrical pulses is applied to a first channel of electrodes and a second phase of electrical pulses is applied to a second channel of electrodes. Using the biphasic sequential pulse train pattern, the second phase of electrical pulses commences after termination of the first phase of electrical pulses such that there is a time delay therebetween. Using the biphasic overlapping pulse train pattern, the second phase of electrical pulses commences simultaneous with or before termination of the first phase of electrical pulses such that there is an overlap therebetween.

In another example, a plurality of cycles of a triphasic sequential or overlapping pulse train pattern may be used, in which a first phase of electrical pulses is applied to a first channel of electrodes, a second phase of electrical pulses is applied to a second channel of electrodes, and a third phase of electrical pulses is applied to the first channel of electrodes. Using the triphasic sequential pulse train pattern, the second phase of electrical pulses commences after termination of the first phase of electrical pulses such that there is a time delay therebetween and, similarly, the third phase of electrical pulses commences after termination of the second phase of electrical pulses such that there is a time delay therebetween. Using the triphasic overlapping pulse train pattern, the second phase of electrical pulses commences simultaneous with or before termination of the first phase of electrical pulses such that there is an overlap therebetween and, similarly, the third phase of electrical pulses commences before termination of the second phase of electrical pulses such that there is an overlap therebetween. Furthermore, the biphasic or triphasic pulse train patterns can be coupled or paired together, creating four, five, or six phases grouped together.

In yet another example, the series of electrical pulses comprises a functional pulse train pattern applied to one or more channels of electrodes. In this example, the pulse train pattern attempts to mimic the electrical sequencing of particular muscles involved during normal functioning activity. Examples would include, but are not limited to, the dorsiflexion and eversion of the ankle typically accomplished during walking; extending, flexing, and opposing the fingers to assist in gripping or holding objects.

In a further example, the series of electrical pulses comprises a low-frequency pulse train pattern applied to one or more channels of electrodes, wherein the individual electrical pulses are generated at a frequency of between 4 Hz and 200 Hz to selectively generate the relative selective production neurotransmitters and modulators (endorphins, dynorphins, enkephalin, and serotonin, etc.) based on the frequency selected. Stimulation at specific frequencies is believed to have beneficial effects in the treatment of the neurological disorders due to the normalization of hyperactive sensory centers (which play a role in the re-education of the central pattern generators) or triggering descending inhibition to reduce overactive muscle tone and/or spasticity. The use of a single frequency of stimulation may be most effective in targeting a single mechanism of inhibition that may be dysfunctional.

Alternatively, a frequency-sequenced pulse burst train pattern may be applied to one or more channels of electrodes, wherein different sequences of modulated electrical pulses are generated at different burst frequencies. Preferably, the different burst frequencies are selected so as to generate the simultaneous production of endorphins, dynorphins, enkephalin, and serotonin during each of the respective sequences, which is believed to have beneficial effects in the treatment of neurological disorders due to the normalization of hyperactive sensory inputs (which play a role in the re-education of the central pattern generators) or triggering descending inhibition to reduce overactive muscle tone and/or spasticity. The combined effect of the generation of multiple inhibitory or excitatory neurotransmitters may provide a more powerful effect than a single neurotransmitter for use in more difficult cases or as a more generalized approach as compared to the single frequency method.

Transcranial Direct Current Stimulation

As discussed above, the present invention is directed to an electrical stimulation system and method which comprises a transcranial direct current stimulator having a one or more channels of electrodes adapted to stimulate the somatosensory and motor control regions of the brain.

The transcranial direct current stimulation may be constant, pulsed, modulated, or interferential. In one aspect, the direct current is a constant current or constant voltage or combination thereof. In another aspect, the direct current comprises a series of electrical pulses at a mid-frequency pattern applied to one or more channels of electrodes, wherein the individual electrical pulses are generated at a carrier frequency. The stimulation may be a constant current, constant voltage, or combination thereof. In still another aspect, the direct current is a frequency-sequenced pulse burst train pattern, wherein different sequences of modulated electrical pulses are generated at different burst frequencies.

In one aspect, the transcranial direct current stimulation is applied before the neuromuscular patterned electrical stimulation as a pre-conditioning step. The preconditioning step usually lasts for less than 500 milliseconds, and preferably less than 300 milliseconds, prior to the activation of the first channel of peripheral stimulation.

The electrical stimulation methods of the present invention may also be combined with the administration of therapeutically effective amounts of various pharmaceuticals useful for treating neurological disorders, such as dopamine uptake inhibitors, norepinephrine reuptake inhibitors, selective serotonin reuptake inhibitors, monoamine oxidase inhibitors, serotonin and noradrenaline reuptake inhibitors, norepinephrine uptake inhibitors, dopamine agonists, acetocholinesterase inhibitors, catechol O-methyltransferase inhibitors, and anticholinergic agents. Antioxidants can also be used with other neuroprotective agents as adjuncts to transcranial stimulation.

BRIEF DESCRIPTION OF THE DRAWINGS

The present invention will be described in greater detail in the following detailed description of the invention with reference to the accompanying drawings that form a part hereof, in which:

FIG. 3C (lower panel) illustrates a method for treating a neurological disorder in a patient by applying neuromuscular electrical stimulation in accordance with a third exemplary embodiment of the present invention, in which the facial muscles (e.g. masseter and/or pterygoid muscles) and the cervical paraspinal muscles of the patient are stimulated. The neuromuscular electrical stimulation is combined with transcranial direct current electrical stimulation as generally illustrated in FIG. 4.

In FIG. 4B, the negative electrode 118b is then placed contralaterally to the positive electrode 118a, and in FIG. 4C, the negative electrode is placed over the prefrontal cortex or on the patient's neck or shoulder region.

In FIG. 4D, the positive electrodes 118a and 120a are placed contralaterally to each over the somatosensory and motor control regions of the brain. The negative electrodes 118b and 120b are then placed contralaterally to each other on the same side as their corresponding positive electrodes 118a, 120a over the prefrontal cortex (top panel) or on the patient's shoulder (bottom panel).

In FIG. 4E, the positive electrodes 118a and 120a are placed contralaterally to each over the same somatosensory and motor control regions of the brain. The negative electrodes 118b and 120b are then placed contralaterally to each other on the opposite side of the prefrontal cortex (top panel) or the patient's shoulder (lower panel) compared to their corresponding positive electrodes 118a, 120a.

In FIG. 4E, the electrodes are crossed to form an interferential current. As each channel of direct or pulsed direct current is electrically isolated from each other, when the electrodes are placed in such a manner that the fields intersect, new fields are created in the deep tissue from the summation of the two or more fields. These fields are the vector sum of the two fields and allow the signal to be steered to selective areas of the deeper tissue in the brain that would not otherwise be accessible from surface stimulation, such as the lower extremity somatosensory and motor control sites. The polarity of the summation or vector field in the deep brain tissue is dependent on the polarity of the superficial electrode placement. This approach uniquely allows stimulation or inhibition of deep brain structures based on the polarity of the direct or pulsed direct current field. If the pulsed direct current is of a sufficient frequency it can overcome the tissue impedance and capacitively couple through the skull more efficiently than a straight direct current field, although both will cause summation vectors in the deep brain tissue.

FIG. 5 illustrates the timing diagram of the transcranial direct current stimulation.

DETAILED DESCRIPTION OF THE INVENTION

Figure 1A:
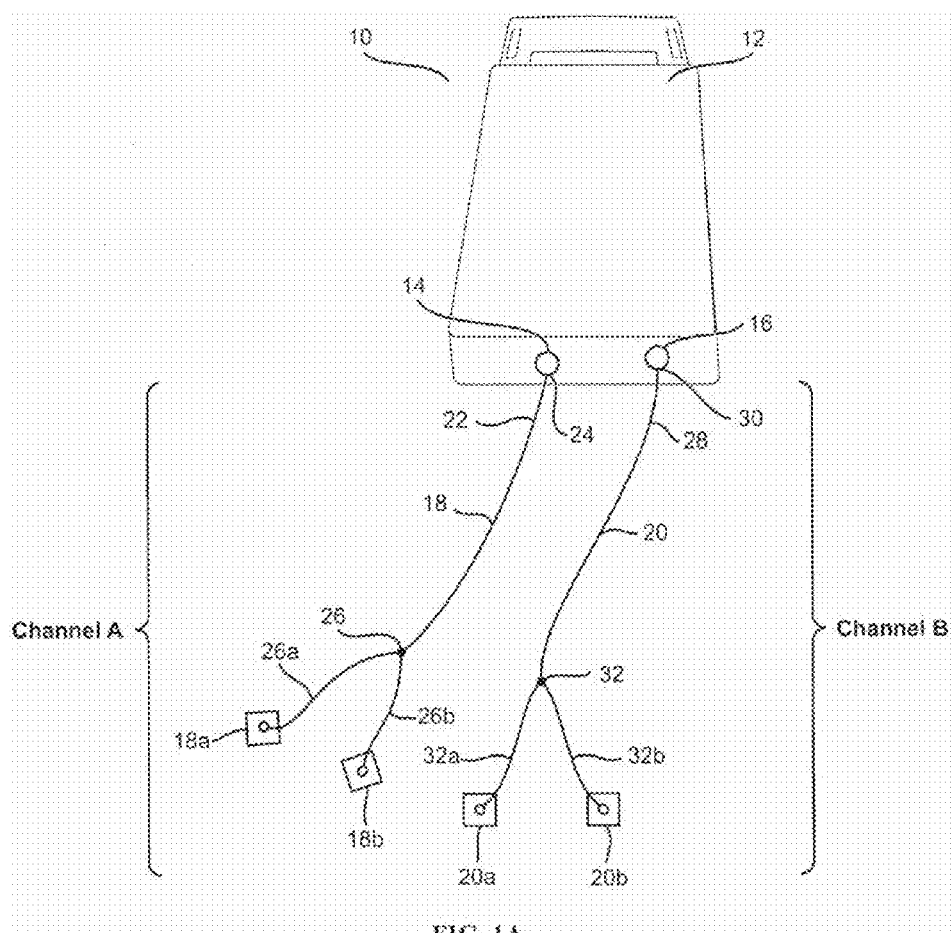
FIG. 1A is a block diagram of a neuromuscular electrical stimulation device that may be used in accordance with the electrical stimulation system and method of the present invention.

The present invention is directed to an electrical stimulation system and method for the treatment of neurological disorders.

As used herein, the term "administration" refers to a method of giving an agent to a patient, where the method is, e.g., topical, oral, intravenous, transdermal, intraperitoneal, or intramuscular. The preferred method of administration can vary depending on various factors, e.g., the components of the pharmaceutical composition.

As used herein, "concurrent administration," "co-administration," or "co-treatment" includes administration of the agents together, or before or after each other. The therapeutic agents co-administered with the electrical stimulation treatment methods may be administered by the same or different routes.

As used herein, the term "electrical stimulation" refers to the passing of various types of current to a patient through transcutaneous or percutaneous electrodes, and includes indirect nerve and/or muscle activation by stimulation of the nerves innervating the sensor (cutaneous and position sensors) and muscle fibers associated with central pattern generator inputs or inhibitory mechanism and stimulation of motor efferent fibers which activate the muscles in the target region.

Examples of the types of electrical stimulation that may be used include, but are not limited to, Patterned Electrical Neuromuscular Stimulation ("PENS"), Transcutaneous Electrical Nerve Stimulation ("TENS"), Neuromuscular Electrical Stimulation ("NMES"), and Interferential Current ("IFC"), Percutaneous Electrical Muscle Stimulation ("PEMS"), Percutaneous Electrical Nerve Stimulation ("PENS"), pulsed magnetic field neuromuscular depolarization systems, functional electrical stimulation ("FES"), and electroacupuncture, which may use alternating or modulated alternating current waveforms, asymmetrical or symmetrical biphasic pulsed current waveforms, and monophasic pulsed current waveforms, or sine wave modulation. Of course, one skilled in the art will appreciate that other types of electrical stimulation may also be used in accordance with the present invention.

As used herein, the term "direct current" refers to an electric current which flows in one direction only through a circuit or equipment creating a net ion flow. The term "direct current" includes both constant (continuous) and pulsed (interrupted) direct current. The associated direct current, in contrast to alternating current, is of unchanging polarity. Direct current corresponds to a drift or displacement of electric charge in one unvarying direction around the closed loop or loops of an electric circuit. The polarity may be reversed from time to time; however, net ion flow must be created. Direct currents and voltages may be of constant magnitude or may vary with time.

As used herein, the term "motor cortex" refers to the primary motor cortex (or M1) and optionally the secondary motor cortices, such as the posterior parietal cortex, the premotor cortex, and the supplemental motor area.

As used herein, the term "somatosensory cortex" refers to the lateral postcentral gyrus and is roughly the same as Brodmann areas 3, 1, and 2.

As used herein, the term "motor point" refers to an area of tissue that can be electrically stimulated by lower levels of electricity compared to surrounding areas. The motor point overlies the innervation zone of a muscle where the motor nerve endings are concentrated or where the nerve trunk enters the muscle. The motor point is often used as a placement site for surface electrodes used to stimulate the muscle. In the following embodiments, motor points of the muscles are preferably stimulated.

As used herein, the term "neurological disorder" refers to strokes, traumatic brain injury, cerebral palsy, dystonias, hydrocephalus, toxicity, inflammation, muscular dystrophies, motor neuron diseases, inflammatory myopathies, neuromuscular junction disorders, peripheral nerve disorders, as well as neurodegenerative disorders such as, multiple sclerosis, Parkinson's disease and other neurological conditions resulting in a reduction of motor function. Examples of motor neuron diseases include, but are not limited to, adult spinal muscular atrophy, amyotrophic lateral sclerosis or Lou Gehrig's Disease, infantile progressive spinal muscular atrophy or SMA Type 1 or Werdnig-Hoffman, intermediate spinal muscular atrophy or SMA Type 2, juvenile spinal muscular atrophy or SMA Type 3 or Kugelberg-Welander, spinal bulbar muscular atrophy (SBMA) or Kennedy's Disease, or X-linked SBMA. Examples of neuromuscular junction diseases include, but are not limited to, myasthenia gravis, Lambert-Eaton Syndrome, and congenital myasthenic syndrome.

Examples of peripheral nerve disorders include, but are not limited to, Charcot-Marie-Tooth Disease or peroneal muscular atrophy, Dejerine-Sottas Disease, and Friedreich's Ataxia. Other myopathies include myotonia congenita or Thomsen's and Becker's Disease, paramyotonia congenita, central core disease, periodic paralysis (PP) hypokalemic and hyperkalemic, endocrine myopathies, and mitochondrial myopathies.

The term "stroke" refers to the multitude of subcategories of cerebrovascular diseases including thrombotic or embolic infarction as well as intracerebral hemorrhage from a vascular or post operative nature.

In a preferred aspect, the present invention is used in the treatment of neurological disorders following stroke. Stroke is the second most common cause of death and the leading cause of adult disability in the United States today. 700,000 strokes occur each year in the United Sates leaving 500,000 survivors with residual disability. Forty percent of these survivors have moderate impairment and functional limitation related to motor function and basic mobility while 15-30% are severely disabled. Patients with intact cortical function have an advantage when it comes to brain plasticity during the functional reorganization that occurs following stroke. Patients with hemorrhagic strokes or left hemiparesis (right hemispheric lesion) are believed to have greater motor impairment and poorer prognosis for recovery of motor function than patients with ischemic strokes or right hemiparesis (left hemispheric lesions).

As used herein, the term "neutral" in the context of an electrode means that the stimulation at that region will not cause a significant physical or neurological change. Typically, this means than the region (e.g. the forehead, neck, or shoulder) receives less than 0.015 amps per square centimeter of current.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "therapeutically effective amount" as used herein, means that amount of an active agent which, alone or in combination with other drugs, provides a therapeutic benefit in the prevention, treatment, or management a neurological disorder. Different therapeutically effective amounts may be applicable for each disorder, as will be readily known by those of ordinary skill in the art.

As used herein, the term "tissue" refers to an aggregation of morphologically similar cells and associated intercellular matter acting together to perform one or more specific functions in the body, including epithelial, connective, muscle, and neural tissue.

As used herein, the term "treatment" refers to the treatment of a neurological disorder in a patient, such as a mammal (particularly a human), which includes preventing, ameliorating, suppressing, or alleviating one or more of the symptoms of the neurological disorder.

As used herein, the term "agonist muscle" broadly refers to a muscle that is resisted or counteracted by another muscle, the "antagonist muscle." Examples of agonist/antagonist muscle pairs include abductors/adductors, flexors/extensors, supinators/pronators, protractors/retractors, and evertors/invertors.

As used herein, the term "abductors" refers to muscles that generally cause movement away from the body centerline while "adductors" are muscles that generally cause movement toward the body centerline.

As used herein, the term "flexors" refers to muscles that generally reduce the angle of a joint, while the "extensors" reduce the angle of the joint. For example, both the flexor carpi radialis and flexor carpi ulnaris are both flexors of the wrist. The extensor carpi radialis longus, in conjunction with extensor carpi radialis brevis, is an extensor of the wrist.

As used herein, the term "pronator" refers to a muscle that causes the movement of the wrist from the palm facing front to the palm facing hack. The opposing movement, which turns the palm forward, is directed by a "supinator."

As used herein, the term "protractor" refers to a muscle that moves a part of the body anteriorly in the horizontal plan while a "retractor" is involved in the reverse movement.

As used herein, the term "evertor" refers to a muscle involved in the twisting motion of the foot that turns the sole outward while the opposite movement of turning the sole inward is performed by an "inverter" muscle.

Referring to FIG. 1, an exemplary embodiment of an electrical stimulation system that may be used in accordance with the method of the present invention. The electrical stimulation system comprises a neuromuscular stimulation device 10 and a transcranial electrical stimulation device 100. It will be appreciated by those skilled in the art that while the neuromuscular simulation device 10 and transcranial electrical stimulation device 100 may be combined in to a single device operated by a single electronic control unit. However, for simplicity, separate devices will be described herein.

Neuromuscular Stimulation Device

As shown in FIG. 1A, the neuromuscular stimulation device is designated generally as reference numeral 10. The neuromuscular electrical stimulation device 10 generally comprises an electronic control unit 12 with a plurality of output connectors 14, 16, which are connected to a plurality of output cables 18, 20 and associated electrode pairs 18a, 18b, and 20a, 20b, respectively. Although two output connectors 14, 16 are shown in FIG. 1A, it should be understood that electronic control unit 12 may include any number of output connectors (such as one, two, six, or eight output connectors) in accordance with the present invention. In addition, one or more of the cables may be bifurcated into multiple (e.g., 2, 3, 4, 5, or 6) electrodes.

Output cables 18, 20 each comprise any suitable type of insulated conductive cable, such as a coaxial cable. In the illustrated embodiment, output cable 18 includes a back section 22 with a connector 24 (such as a male jack) that attaches to output connector 14, and a front section 26 that splits into a first split end 26a and a second split end 26b. Similarly, output cable 20 includes a back section 28 with a connector 30 (such as a male jack) that attaches to output connector 16, and a front section 32 that splits into a first split end 32a and a section split end 32b. Of course, it should be understood that each of output cables 18, 20 could alternatively be manufactured out of two separate leads (instead of having a front section with split ends). In addition, output cables 18, 20 could be connected directly to electronic control unit 12 without the use of connectors.

As can be seen in FIG. 1A, electrodes 18a, 18b are attached to split ends 26a, 26b of output cable 18, respectively. Similarly, electrodes 20a, 20b are attached to split ends 32a, 32b of output cable 20, respectively. As such, output cable 18 and electrodes 18a, 18b together form a first output channel (referred to hereinafter as "channel A"), and output cable 20 and electrodes 20a, 20b together form a second output channel (referred to hereinafter as "channel B"). Although two channels are shown in FIG. 1, it should be understood that any number of channels may be used in accordance with the present invention (provided, of course, that the number of channels corresponds to the number of output connectors of electronic control unit 12).

In the illustrated example, electrodes 18a and 20a each comprise a relative positive electrode, and electrodes 18b and 20b each comprise a relative negative electrode. As will be described in greater detail herein below, each of the electrical pulses applied to electrodes 18a, 18b and electrodes 20a, 20b may comprise, for example, a monophasic waveform (which has absolute polarity), a biphasic asymmetric waveform (which has relative polarity), or a biphasic symmetric waveform (which has no polarity). Thus, as used herein, the term "positive electrode" refers to a relative positive electrode and the term "negative electrode" refers to a relative negative electrode (regardless of whether the electrical pulse comprises a monophasic waveform, an asymmetric biphasic waveform, or a symmetric biphasic waveform (which behaves like the relative positive or relative negative electrode during each phase of the waveform)).

Electrodes 18a, 18b and 20a, 20b are each adapted to be positioned in electrical conduct with tissue of selected regions of a patient, as will be described in greater detail herein below with reference to FIGS. 3A-3W. In the illustrated embodiment, each of electrodes 18a, 18b and 20a, 20b comprises a transcutaneous electrode having a surface electrode pad that may be placed on the skin of a patient. As is known in the art, each of electrodes 18a, 18b and 20a, 20b may be formed of metal or some other physiologically acceptable conductive material and may take on a variety of different sizes and shapes. Of course, one or more of electrodes 18a, 18b and 20a, 20b may alternatively comprise a percutaneous electrode, such as a needle electrode, or any other type of suitable electrode in accordance with the present invention.

Electronic control unit 12 also includes internal circuitry (not shown) for selectively generating a series of electrical pulses in accordance with a procedure for treating a neurological disorder. The series of electrical pulses generated by the circuitry are provided at output connectors 14, 16 and, as such, may be applied to a patient through channel A and/or channel B. The series of electrical pulses may comprise a variety of different types of pulse train patterns, such as: a plurality of cycles of a biphasic sequential pulse train pattern; a plurality of cycles of a biphasic overlapping pulse train pattern; a plurality of cycles of a triphasic sequential pulse train pattern; a plurality of cycles of a triphasic overlapping pulse train pattern; a functional pulse train pattern; a low-frequency pulse train pattern; or a frequency-sequenced pulse burst train pattern. Each of these pulse train patterns will be described in detail herein below with reference to FIGS. 2A-2H. One skilled in the art will understand that a variety of different circuit configurations may be used to generate the various pulse train patterns, such as the circuitry described in Palermo U.S. Pat. No. 5,562,718, which is incorporated herein by reference.

A variety of different neuromuscular electrical stimulation devices may be used and/or adapted for use in accordance with the present invention. For example, one could easily incorporate the protocols disclosed herein into the OMNIS-TIM® FX² patterned electrical neuromuscular stimulator or the OMNISTIM® FX² Pro patterned electrical neuromuscular stimulator, both of which are sold by the assignee of the present application. Of course, other types of electrical stimulation devices could also be used, which are generally available in the industry.

Referring now to FIGS. 2A-2H, examples of the various types of pulse train patterns that may be used in accordance with the present invention will now be described herein below. Each of the pulse train patterns is comprised of a series of individual electrical pulses arranged into a particular pattern. Each of the electrical pulses may comprise either a monophasic or biphasic waveform, which may be, for example, asymmetric, symmetric, square, sinusoidal, overlapping sinusoidal (interferential), and the like. Preferably, each of the electrical pulses comprises a biphasic asymmetric square wave having a pulse duration that ranges between 30 microseconds and 400 microseconds (preferably less than 100 microseconds) during the positive and negative phases and a current amplitude that typically ranges between 25 milliamps and 140 milliamps. It will be appreciated that the higher currents may be tolerable (for example up to 200 milliamps) when the pulse width is lowered.

It has been found that electrical pulses having a short pulse duration and high current amplitude selectively trigger p-type calcium channels (preferably having a pulse duration of 30-100 microseconds and a current amplitude of 25-140 milliamps). Activation of p-type calcium channels will in turn trigger the release of nerve growth factor ("NGF") to sustain axon regeneration and repair. This repeated p-type calcium channel activation increases the calcium pool at the neuromuscular junction, which facilitates enhanced muscle recruitment. Twitch contractions may increase in intensity during the treatment even though the stimulation output is not increased as observed empirically. This additional calcium at the neuromuscular junction lasts for several hours post-treatment, which facilitates voluntary movement. See Regeneron Corp. (Tarrytown, N.Y.) Neural stimulation effects presentation, Society for Neuroscience, San Diego 1998 (short and long term nerve growth potentiation using repetitive electric stimulation).

Biphasic Sequential Pulse Train Pattern

Figure 2A:
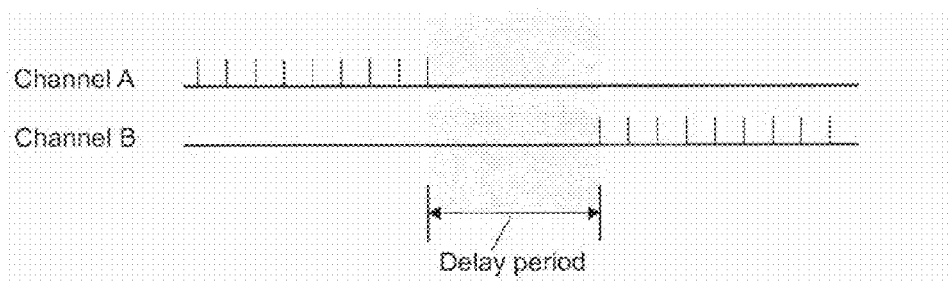
FIG. 2A is a timing diagram of a biphasic sequential pulse train pattern that may be applied to the output channels of the neuromuscular electrical stimulation device of FIG. 1.

Referring to FIG. 2A, electrical stimulation system 10 may be used to apply a plurality of cycles of a biphasic sequential pulse train pattern to a patient. In a typical biphasic sequential pulse train pattern, a first phase of electrical pulses is applied to channel A and a second phase of electrical pulses is applied to channel B with a delay period therebetween.

In the illustrated example, the first phase of electrical pulses is applied to channel A for approximately 60 milliseconds to 120 milliseconds (and most preferably for 100 milliseconds). At the conclusion of the first phase of electrical pulses, there is a delay period of approximately 0 milliseconds to 100 milliseconds (and most preferably 80 milliseconds) before the second phase of electrical pulses is applied to channel B. Then, the second phase of electrical pulses is applied to channel B for approximately 60 milliseconds to 120 milliseconds (and most preferably for 100 milliseconds). The frequency of the individual electrical pulses in each phase is approximately 30 Hz to 100 Hz (and most preferably 50 Hz).

The biphasic sequential pulse train pattern described above may be repeated approximately every 0.33 seconds (3 Hz) to 3 seconds (0.33 Hz). Preferably, the pulse train pattern is applied to the patient for a total treatment time of approximately 10 minutes to 30 minutes (and most preferably for 20 minutes), as desired for a particular treatment.

Biphasic Overlapping Pulse Train Pattern

Figure 2B:
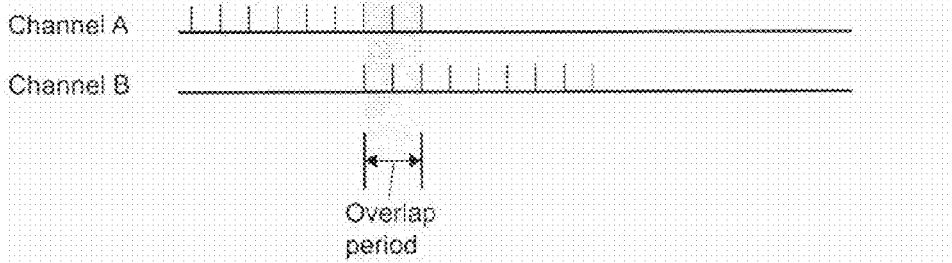
FIG. 2B is a timing diagram of a biphasic overlapping pulse train pattern that may be applied to the output channels of the neuromuscular electrical stimulation device of FIG. 1.

Referring to FIG. 2B, electrical stimulation system 10 may also be used to apply a plurality of cycles of a biphasic overlapping pulse train pattern to a patient. In a typical biphasic overlapping pulse train pattern, a first phase of electrical pulses is applied to channel A and a second phase of electrical pulses is applied to channel B with an overlap period therebetween.

In the illustrated example, the first phase of electrical pulses is applied to channel A for approximately 60 milliseconds to 120 milliseconds (and most preferably for 100 milliseconds). When the first phase of electrical pulses has reached a time period of between 40 milliseconds and 100 milliseconds (and most preferably 80 milliseconds), the second phase of electrical pulses is applied to channel B for approximately 60 milliseconds to 120 milliseconds (and most preferably for 100 milliseconds). Thus, there is an overlap period of approximately 20 milliseconds to 80 milliseconds (and most preferably 20 milliseconds) during which both channel A and channel B are providing electrical stimulation to the patient. The frequency of the individual electrical pulses in each phase is approximately 30 Hz to 100 Hz (and most preferably 50 Hz).

The biphasic overlapping pulse train pattern described above may be repeated approximately every 0.33 seconds (3 Hz) to 3 seconds (0.33 Hz). Preferably, the pulse train pattern is applied to the patient for a total treatment time of approximately 10 minutes to 60 minutes (and most preferably 20 minutes), as desired for a particular treatment.

Triphasic Sequential Pulse Train Pattern

Figure 2C:
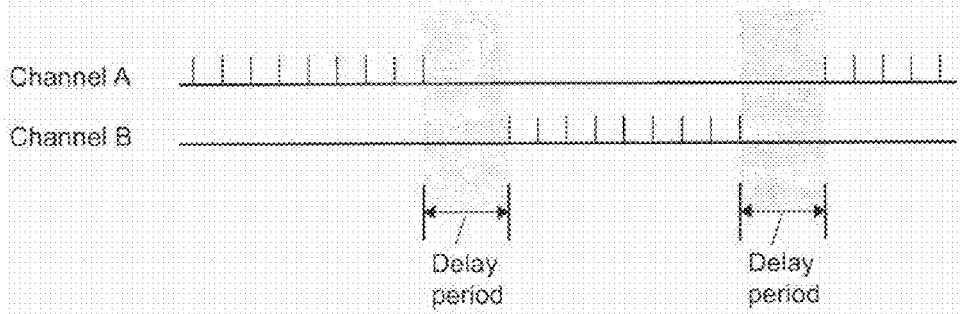
FIG. 2C is a timing diagram of a triphasic sequential pulse train pattern that may be applied to the output channels of the neuromuscular electrical stimulation device of FIG. 1.

Referring to FIG. 2C, electrical stimulation system 10 may also be used to apply a plurality of cycles of a triphasic sequential pulse train pattern to a patient. In a typical triphasic sequential pulse train pattern, a first phase of electrical pulses is applied to channel A, a second phase of electrical pulses is applied to channel B, and a third phase of electrical pulses is applied to channel A, wherein there is a delay period between the first and second phases of electrical pulses and another delay period between the second and third phases of electrical pulses.

In the illustrated example, the first phase of electrical pulses is applied to channel A for approximately 60 milliseconds to 120 milliseconds (and most preferably for 100 milliseconds). At the conclusion of the first phase of electrical pulses, there is a delay period of approximately 0 milliseconds to 100 milliseconds (and most preferably 80 milliseconds) before the second phase of electrical pulses is applied to channel B. Then, the second phase of electrical pulses is applied to channel B for approximately 60 milliseconds to 120 milliseconds (and most preferably for 100 milliseconds). At the conclusion of the second phase of electrical pulses, there is a delay period of approximately 0 milliseconds to 100 milliseconds (and most preferably 80 milliseconds) before the third phase of electrical pulses is applied to channel A. Then, the third phase of electrical pulses is applied to channel A for approximately 36 milliseconds to 72 milliseconds (and most preferably for 60 milliseconds). The frequency of the individual electrical pulses in each phase is approximately 30 Hz to 100 Hz (and most preferably 50 Hz).

The triphasic sequential pulse train pattern described above may be repeated approximately every 0.3 seconds (3.3 Hz) to 3 seconds (0.33 Hz). Preferably, the pulse train pattern is applied to the patient for a total treatment time of approximately 10 minutes to 60 minutes (and most preferably 20 minutes), as desired for a particular treatment.

Figure 2D:
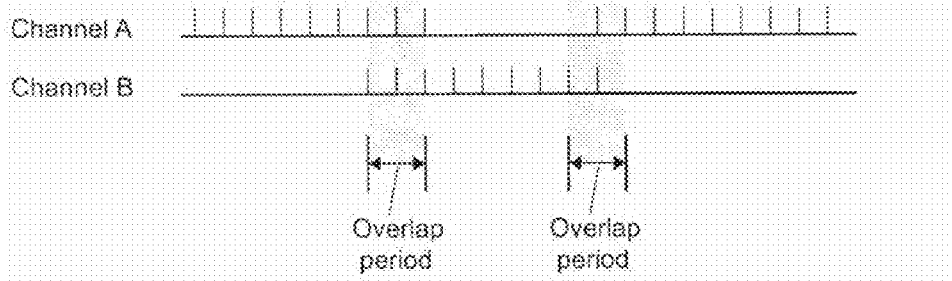
FIG. 2D is a timing diagram of a triphasic overlapping pulse train pattern that may be applied to the output channels of the neuromuscular electrical stimulation device of FIG. 1.

Referring to FIG. 2D, electrical stimulation system 10 may also be used to apply a plurality of cycles of a triphasic overlapping pulse train pattern to a patient. In a typical triphasic overlapping pulse train pattern, a first phase of electrical pulses is applied to channel A, a second phase of electrical pulses is applied to channel B, and a third phase of electrical pulses is applied to channel A, wherein there is an overlap period between the first and second phases of electrical pulses and another overlap period between the second and third phases of electrical pulses.

In the illustrated example, the first phase of electrical pulses is applied to channel A for approximately 60 milliseconds to 120 milliseconds (and most preferably for 100 milliseconds). When the first phase of electrical pulses has reached a time period of between 40 milliseconds and 100 milliseconds (and most preferably 80 milliseconds), the second phase of electrical pulses is applied to channel B for approximately 60 milliseconds to 120 milliseconds (and most preferably 100 milliseconds). Thus, there is an overlap period of approximately 0 milliseconds to 100 milliseconds (and most preferably 20 milliseconds) during which both channel A and channel B are providing electrical stimulation to the patient. When the second phase of electrical pulses has reached a time period of between 40 milliseconds and 100 milliseconds (and most preferably 80 milliseconds), the third phase of electrical pulses is applied to channel A for approximately 36 milliseconds to 72 milliseconds (and most preferably 60 milliseconds) the third phase of electrical pulses has a shorter time duration than that of the first phase of electrical pulses). Thus, there is an overlap period of approximately 0 milliseconds to 72 milliseconds (and most preferably 20 milliseconds) during which both channel B and channel A are providing electrical stimulation to the patient. The frequency of the individual electrical pulses in each phase is approximately 30 Hz to 100 Hz (and most preferably 50 Hz).

The triphasic overlapping pulse train pattern described above may be repeated approximately every 0.33 seconds (3 Hz) to 3.0 seconds (0.33 Hz). Preferably, the pulse train pattern is applied to the patient for a total treatment time of approximately 10 minutes to 60 minutes (and most preferably 20 minutes), as desired for a particular treatment.

Functional Pulse Train Pattern

Electrical stimulation system 10 may also be used to apply a functional pulse train pattern to a patient. The functional pulse train pattern is applied to channel A and channel B (or to additional channels) so as to mimic the electrical sequencing of particular muscles involved during normal functional activity. One skilled in the art will understand that the functional pulse train pattern for a particular functioning activity (e.g., chewing, moving the bolus, or swallowing) may be obtained through the use of an electromyographic (EMG) recording device. The sequence of firing of the muscles, firing frequencies, and the duration and frequency of the firing of the muscles may thus be determined for standardized healthy normal subjects and may then be programmed into the appropriate stimulation pattern. Preferably, the functional pulse train pattern is applied to the patient for a total treatment time of approximately 10 minutes to 60 minutes (and most preferably 20 minutes), as desired for a particular treatment. Examples include, but are not limited to, gripping, holding, pinching, sit-to-stand activities, cycling, walking, and ankle dorsiflexion.

Low-Frequency Pulse Train Pattern

Figure 2E:
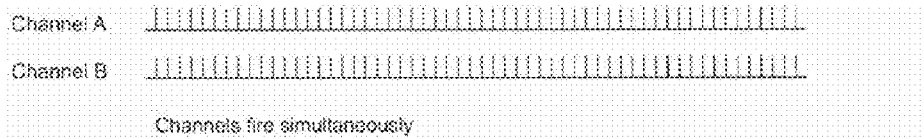
FIG. 2E is a timing diagram of a low-frequency pulse train pattern that may be applied to the output channels of the neuromuscular electrical stimulation device of FIG. 1.

Referring to FIG. 2E, electrical stimulation system 10 may also be used to apply a low-frequency pulse train pattern to a patient. The low-frequency pulse train pattern may be applied to channel A and/or channel B, wherein the individual electrical pulses are generated on each channel at a frequency of between 4 Hz and 200 Hz. Generally, the frequency of the electrical pulses is selected in order to provide the desired response and release of stimulatory or inhibitory neurotransmitters centrally and spinally while providing the greatest comfort to the patient. If channel A and channel B are both used, the low-frequency pulse train pattern may be applied simultaneously to channel A and channel B, or a different frequency may be applied on each channel to a different area associated with various phases of swallowing. Preferably, the low-frequency pulse train pattern is applied to the patient for a total treatment time of approximately 5 minutes to 60 minutes (and most preferably 20 minutes), as desired for a particular treatment.

Frequency-Sequenced Pulse Burst Train Pattern

Figure 2F:
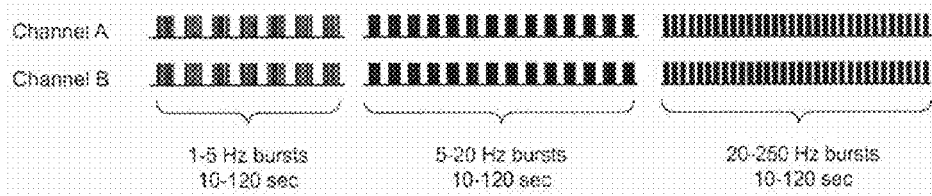
FIG. 2F is a timing diagram of a first frequency-sequenced pulse burst train pattern that may be applied to the output channels of the neuromuscular electrical stimulation device of FIG. 1.
Figure 2G:
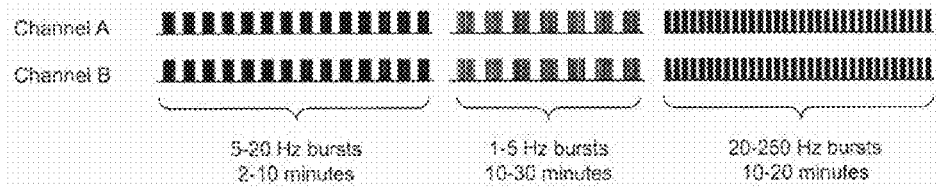
FIG. 2G is a timing diagram of a second frequency-sequenced pulse burst train pattern that may be applied to the output channels of the neuromuscular electrical stimulation device of FIG. 1.
Figure 2H:
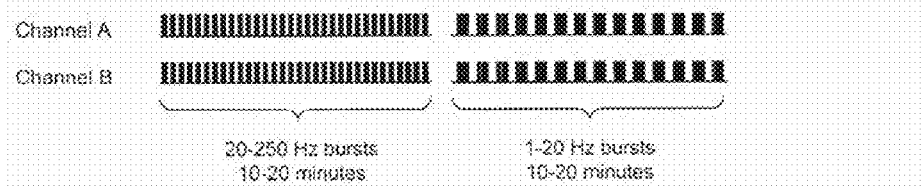
FIG. 2H is a timing diagram of a third frequency-sequenced pulse burst train pattern that may be applied to the output channels of the neuromuscular electrical stimulation device of FIG. 1.

Referring to FIGS. 2F-2H, electrical stimulation system 10 may also be used to apply a frequency-sequenced pulse burst train pattern to a patient. The frequency-sequenced pulse burst train pattern may be applied to channel A and/or channel B, wherein different sequences of modulated electrical pulses are generated at different frequencies. Preferably, the different burst frequencies are selected so as to selectively generate the production of endorphin, dynorphin, and enkephalin/serotonin during each of the respective sequences, which is believed to have beneficial effects in the treatment of the neurological disorders of the present invention.

In the example shown in FIG. 2F, the frequency-sequenced pulse burst train pattern typically has a carrier frequency of 500 Hz to 100,000 Hz with a first sequence of modulated electrical pulses generated at a burst frequency of approximately 0.1 Hz to 10 Hz (preferably 1 to 5 Hz) for a duration of approximately 1 second to 150 seconds (preferably 10 to 120 seconds), a second sequence of modulated electrical pulses generated at a burst frequency of approximately 5 Hz to 20 Hz for a duration of approximately 1 to 150 seconds (preferably 10 seconds to 120 seconds), and a third sequence of modulated electrical pulses generated at a burst frequency of approximately 20 Hz to 250 Hz for a duration of approximately 1 to 150 seconds (preferably 10 seconds to 120 seconds). Preferably, the frequency-sequenced pulse burst train pattern is applied to the patient for a total treatment time of approximately 1 minute to 60 minutes. Using this therapy, the patient begins to receive the effects of all of the neurotransmitters relatively quickly as the frequencies cycle through rapidly. This therapy is also very comfortable and moderately aggressive.

In the example shown in FIG. 2G, the frequency-sequenced pulse burst train pattern typically has a carrier frequency of 500 Hz to 100,000 Hz with a first sequence of modulated electrical pulses generated at a burst frequency of approximately 5 Hz to 20 Hz for a duration of approximately 1 minute to 15 minutes (preferably 2-10 minutes), a second sequence of modulated electrical pulses generated at a burst frequency of approximately 0.1 Hz to 10 Hz (preferably 1-5 Hz) for a duration of approximately 1 minute to 60 minutes (preferably 10 to 30 minutes), and a third sequence of modulated electrical pulses generated at a burst frequency of approximately 20 Hz to 250 Hz for a duration of approximately 1 minute to 30 minutes (preferably 10 to 20 minutes). Preferably, the frequency-sequenced pulse burst train pattern is applied to the patient for a total treatment time of approximately 3 minutes to 50 minutes. This therapy is the most aggressive and least tolerated but provides the longest lasting effect. The initial effect is dynorphin (5-20 Hz), followed by endorphin (1-5 Hz), and then by enkephalin/serotonin (20-250 Hz). Since it takes 15 to 30 minutes to activate endorphin and only 5-10 minutes to activate enkephalin/serotonin, both are present at the completion of the treatment for maximum effect.

In the example shown in FIG. 2H, the frequency-sequenced pulse burst train pattern has a carrier frequency of 500 Hz to 100,000 Hz with a first sequence of modulated electrical pulses generated at a burst frequency of approximately 20 Hz to 250 Hz for a duration of approximately 1 minute to 30 minutes (preferably 10 to 20 minutes), and a second sequence of modulated electrical pulses generated at a burst frequency of approximately 0.1 Hz to 20 Hz (preferably 1 to 20 Hz) for a duration of approximately 1 minute to 20 minutes (preferably 10 to 20 minutes). Preferably, the frequency-sequenced pulse burst train pattern is applied to the patient for a total treatment time of approximately 20 minutes to 40 minutes. This therapy is the least aggressive and best tolerated but provides the shortest lasting effect. The initial effect is enkephalin/serotonin (20-250 Hz) followed by endorphin (1-20 Hz). Since it takes about 15-30 minutes to activate endorphin and only about 5-10 minutes to activate enkephalin/serotonin, both are present at the completion of the treatment. However, the enkephalin/serotonin has begun to deplete as it has a relatively short half life (15 minutes to 2 hours) compared to endorphin (2-6 hours). Stimulation at higher frequencies is better tolerated and thus more appropriate to start with for more sensitive patients.

It will be appreciated that when multiple channels are used (e.g., in the case of biphasic and triphasic pulse patterns), the first pulse pattern is preferably applied to the muscle most seriously affected. For example, if a patient complains of muscle weakness in chewing primarily on the right side of the body, the motor point of the masseter muscle on the right side of the patient's body preferably receives the pulse pattern on channel A and the motor point of the masseter muscle on the left side of the patient's body preferably receives the pulse pattern on channel B.

Transcranial Stimulation Device

Figure 1B:
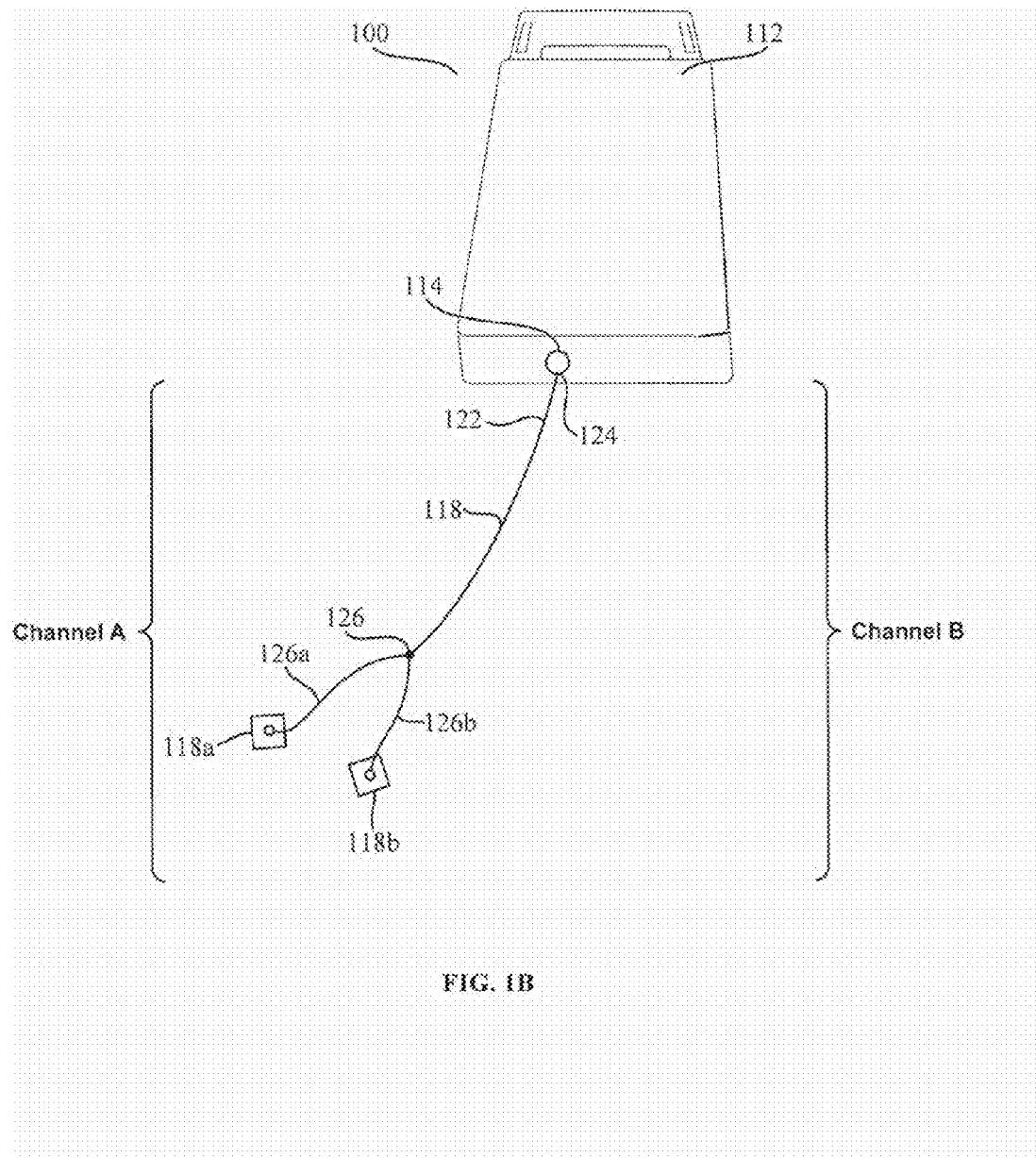
FIG. 1B is a block diagram of a transcranial direct current electrical stimulation device that may be used in accordance with the electrical stimulation system and method of the present invention.

As shown in FIG. 1B, the transcranial stimulation device is designated generally as reference numeral 100. The neuromuscular electrical stimulation device 100 generally comprises an electronic control unit 112 with one or more output connectors 114 which are connected to one or more output cables 118 and associated electrode pairs 118a, 118b respectively. Although one output connector 114 is shown in FIG. 1B, it should be understood that electronic control unit 112 may include any number of output connectors (such as one, two, three, four, five, six, seven, eight, or more output connectors) in accordance with the present invention. In addition, one or more of the cables may be bifurcated into multiple (e.g., 2, 3, 4, 5, or 6) electrodes.

Output cable 118 each comprises any suitable type of insulated conductive cable, such as a coaxial cable. In the illustrated embodiment, output cable 118 includes a back section 122 with a connector 124 (such as a male jack) that attaches to output connector 114, and a front section 126 that splits into a first split end 126a and a second split end 126b. Of course, it should be understood that each of output cable 118 could alternatively be manufactured out of two separate leads (instead of having a front section with split ends). In addition, output cable 118 could be connected directly to electronic control unit 112 without the use of connectors.

As can be seen in FIG. 1B, electrodes 118a, 118b are attached to split ends 126a, 126b of output cable 118, respectively. As such, output cable 118 and electrodes 118a, 118b together form a first output channel. Although one channel is shown in FIG. 1B, it should be understood that any number of channels may be used in accordance with the present invention (provided, of course, that the number of channels corresponds to the number of output connectors of electronic control unit 112).

In the illustrated example, electrode 118a comprise a positive electrode, and electrode 118b comprise a negative electrode. As will be described in greater detail herein below, the direct current applied to each electrodes 118a, 18b may comprise, for example, a continuous direct current or a monophasic (monopolar) waveform (which has absolute polarity). Thus, as used herein, the term "positive electrode" refers to a positive electrode and the term "negative electrode" refers to a negative electrode (regardless of whether the electrical pulse comprises a continuous direct current or monophasic waveform.

Electrodes 118a, 118b are each adapted to be positioned in electrical contact with the transcranial tissue of selected regions of a patient, as will be described in greater detail herein below with reference to FIGS. 4A-4E. In the illustrated embodiments, each of electrodes 118a, 118b comprises a transcutaneous electrode having a surface electrode pad that may be placed on the skin of a patient. As is known in the art, each of electrodes 118a, 118b may be formed of metal or some other physiologically acceptable conductive material and may take on a variety of different sizes and shapes. Of course, one or more of electrodes 118a, 118b may alternatively comprise any other type of suitable electrode in accordance with the present invention.

Electronic control unit 112 also includes internal circuitry (not shown) for selectively generating a series of electrical pulses in accordance with a procedure for treating a neurological disorder. The series of electrical pulses generated by the circuitry are provided at output connector 114, as such, may be applied to a patient through the channels. One skilled in the art will understand that a variety of different circuit configurations may be used to generate the direct current.

A variety of different transcranial direct current electrical stimulation devices may be used and/or adapted for use in accordance with the present invention. For example, one could easily incorporate the protocols disclosed herein into the Iomed Phoresor II direct current stimulator. Of course, other types of electrical stimulation devices could also be used, which are generally available in the industry.

Figure 4A:
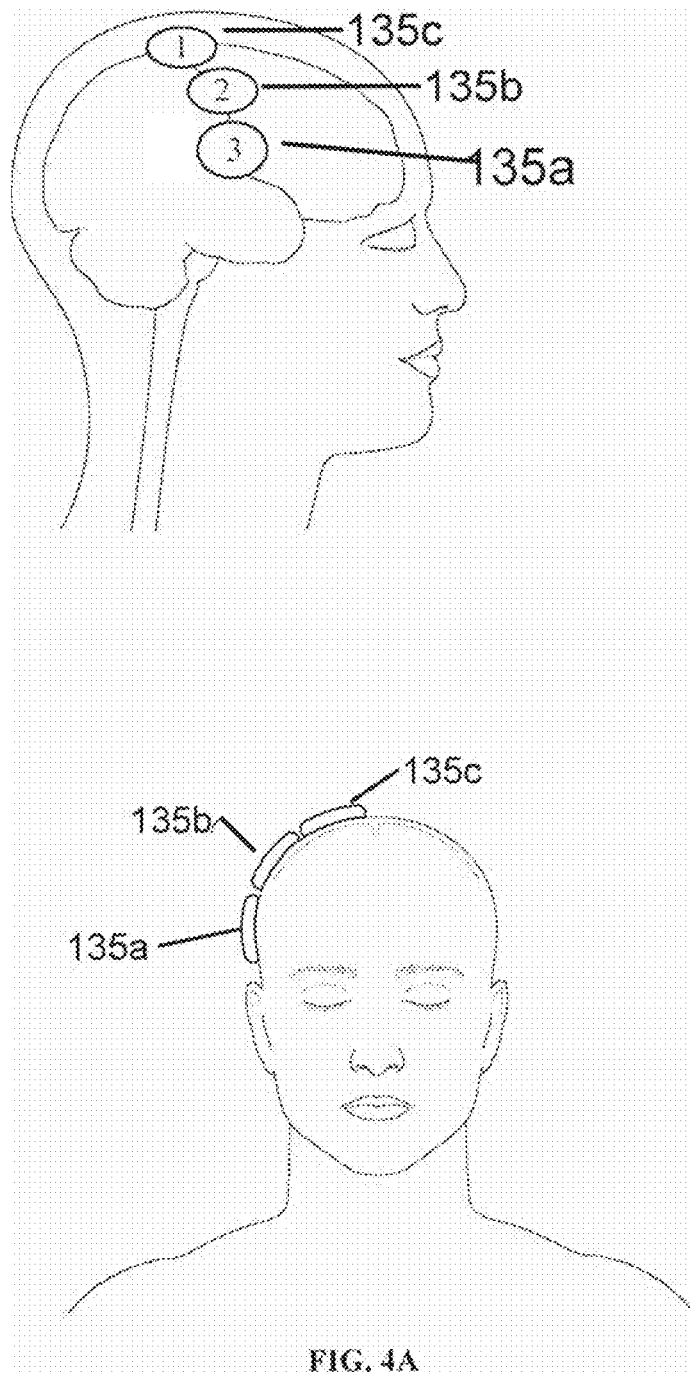
FIG. 4A illustrates a method for treating a neurological disorder in a patient by applying transcranial direct current electrical stimulation to the patient, in which the somatosensory and motor control region of the facial musculature, lower extremity musculature, or upper extremity musculature are stimulated. The top panel is a lateral view of the patient, and the bottom panel is a frontal view of the patient. The transcranial direct current stimulation is combined with neuromuscular electrical stimulation as generally illustrated in FIGS. 3A-3W.

Referring now to FIGS. 4A-4E, at least one of electrode 118a, 118b is adapted to be positioned in electrical contact with tissue of overlying selected regions of the patient's brain. These regions are generally the motor cortex or, more preferably, the somatosensory and motor cortex. In general, as shown in FIG. 4A, there are three primary regions 135a, 135b, or 135c for transcranial electrode placement and stimulation: the cranial region overlying the brain somatosensory and motor control of the facial muscles 135a; the cranial region overlying the brain somatosensory and motor control of the upper extremity muscles 135b; and the cranial region overlying the brain somatosensory and motor control of the lower extremity muscles 135c. It will be appreciated that by decreasing the size of the electrode or otherwise focusing the field, the stimulation may be primarily on the motor cortex region (about 1 cm anterior-laterally).

Figure 4B:
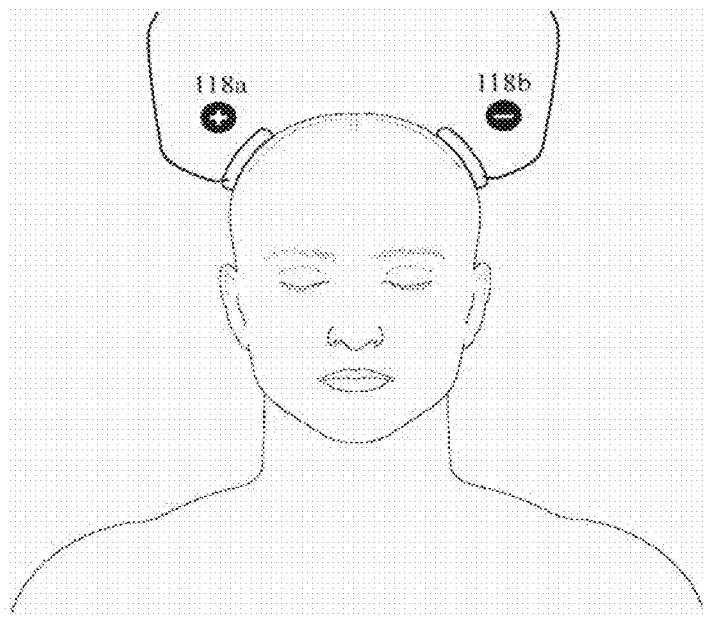
FIGS. 4B-C illustrates three alternative electrode placements for the transcranial stimulation shown in FIG. 4A. In both FIGS. 4B and 4C, the positive electrode 118a is placed over the somatosensory and motor control region of the brain associated with the target muscle.
Figure 4C:
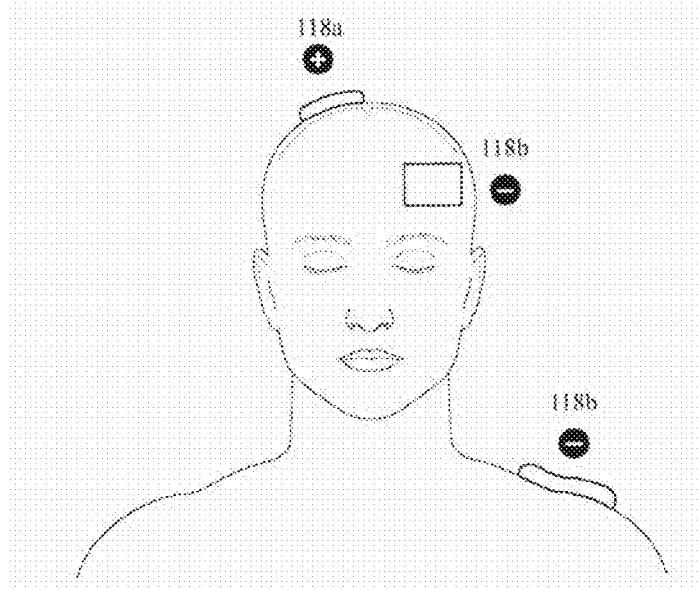

Preferably, the positive electrode is applied overlying the brain target region 135a, 135b, or 135c. The other electrode (typically the positive electrode) is then applied in one of three positions. First, as shown in FIG. 4B, the negative electrode is positioned contralaterally to the same motor control area of the brain. In such a case, the positive electrode is typically about the same size as the negative electrode. Second, as shown in FIG. 4C, the negative electrode is placed in a "neutral" site. Preferred neutral sites are on the forehead on the opposite prefrontal cortex or on the patient's neck or shoulder. In these latter two instances, the negative electrode is typically larger in size than the positive electrode. The size differences focus the field near the smaller electrode to provide more specificity in stimulation of the brain somatosensory and motor control regions.

It will also be appreciated that the brain target region 135a, 135b, and 135c is opposite the affected target area in the periphery. For example, if the patient has a stroke affecting the right side of the brain, the left side of the body is expected to lose function. Applying the positive electrode over the right brain location that controls the left side of the body produces an improvement in function of the left side of the body.

Figure 4D:
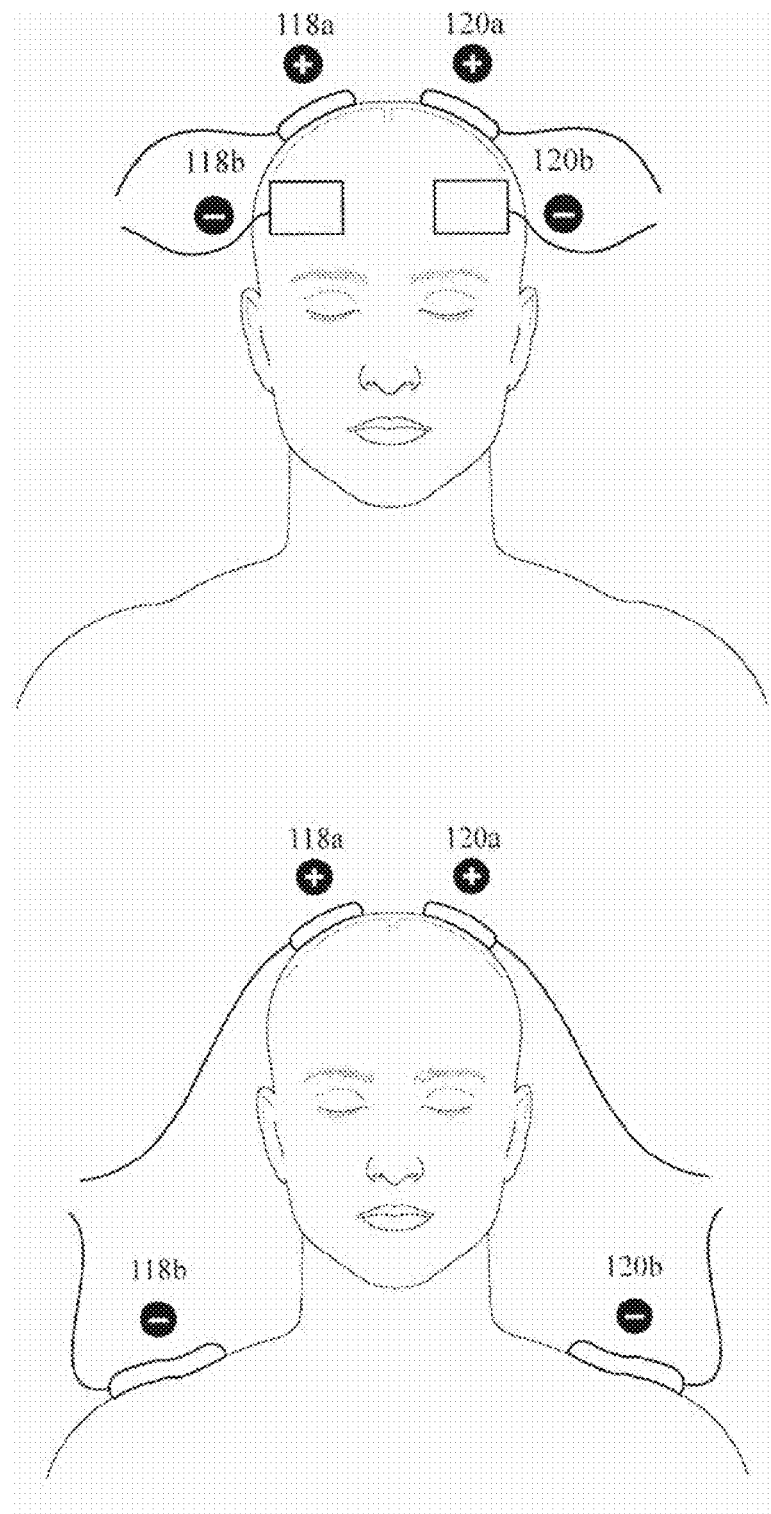
FIG. 4D illustrates two alternative embodiments for electrode placements for the bilateral transcranial direct current stimulation of a patient.

FIG. 4D illustrates two alternative embodiments for the electrode placement for a transcranial direct current stimulator comprising two channels, each having two electrodes 118, 118b and 120a, 120b. These embodiments are also particularly well suited for neurological disorders which affect both sides of the patient's body, such as those involving multiple sclerosis.

As shown in FIG. 4D (top panel), in one embodiment, the first electrode 118a of the first channel is positioned in electrical contact with the cranium overlying the somatosensory and motor control region of the brain (e.g., 135a, 135b, or 135c), and the second electrode 118b of the first channel is positioned in electrical contact with the patient's prefrontal cortex on the forehead on the same side of the body. The electrodes 120a, 120b of the second channel are positioned bilaterally in a similar fashion. This conformation is denoted as a bipolar cranial-forehead electrode placement.

As shown in FIG. 4D (bottom panel), in another embodiment, the first electrode 118a of the first channel is positioned in electrical contact with cranium overlying the somatosensory and motor control region of the brain (e.g., 135a, 135b, or 135c), and the second electrode 118b of the first channel is positioned in electrical contact with the patient's shoulder or neck on the same side of the body. The electrodes 120a, 120b of the second channel are positioned bilaterally in a similar fashion. This conformation denoted as a bipolar cranial-neck electrode placement.

Figure 4E:
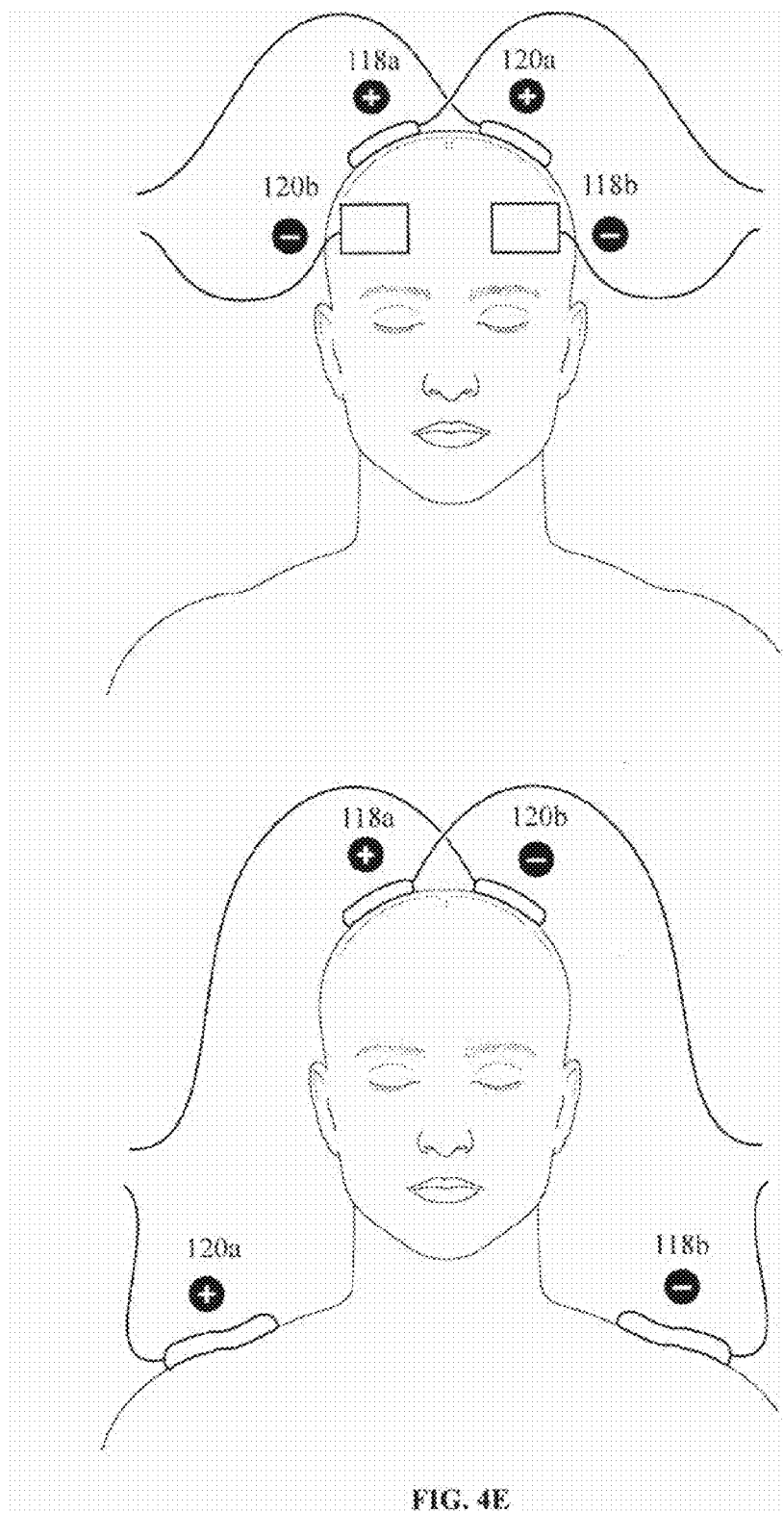
FIG. 4E illustrates two alternative embodiments for electrode placements for the interferential transcranial direct current stimulation of a patient.

FIG. 4E illustrates two alternative embodiments for the electrode placement for a transcranial direct current stimulator comprising two channels, each having two electrodes 118a, 118b and 120a, 120b. These embodiments are also particularly well suited for neurological disorders which affect both sides of the patient's body, such as those involving multiple sclerosis or Parkinson's disease.

In one embodiment (top panel of FIG. 4E), the first electrode 118a of the first channel is positioned in electrical contact with the cranium overlying the somatosensory motor control region of the brain (e.g., 135a, 135b, or 135c), and the second electrode 118b of the first channel is positioned in electrical contact with the patient's prefrontal cortex on the forehead on the opposite side of the body. The electrodes 120a, 120b of the second channel are positioned in a similar fashion. That is, the first electrode 120a of the second channel is positioned contralaterally to first electrode 118a of the first channel, and the second electrode 120b of the second channel is positioned contralaterally to the second electrode 118b of the first channel. This conformation is denoted as a quadripolar cranial-forehead electrode placement. This embodiment is especially useful for transcranially stimulating the regions of the brain associated with somatosensory and motor control of the lower extremities, which are located in the deeper regions of the brain.

In still another embodiment (bottom panel of FIG. 4E), the first electrode 118a of the first channel is positioned in electrical contact with the cranium overlying the somatosensory and motor control region of the brain (e.g., 135a, 135b, or 135c), and the second electrode 118b of the first channel is positioned in electrical contact with the patient's shoulder or neck on the opposite side of the body. The electrodes 120a, 120b of the second channel are positioned in a similar fashion. Thus, the first electrode 120a of the second channel is positioned contralateral to the somatosensory and motor control region of the brain (e.g., 135a, 135b, or 135c), and the second electrode 120b of the second channel is positioned in electrical contact with the patient's shoulder or neck on the opposite side of the body (i.e., but on the same side as the target region 135a, 135b, or 135c). This conformation is denoted as a quadripolar cranial-neck-shoulder electrode placement. This embodiment is especially useful for transcranially stimulating the regions of the brain associated with somatosensory and motor control of the lower extremities, which are located in the deeper regions of the brain.

The transcranial direct current may be continuous, pulsed, and/or burst modulated. The current is preferably a low amperage current, typically less than 10 mA, and more preferably about 0.5 to 2 mA, with about 1 mA being most preferred. The pulse duration for the pulsed direct current is preferably ranges between 0.5 microsecond to 60 minutes, more preferably between about 1 and 10 microseconds, and may be uniform or non-uniform. The pulse frequency of the pulsed direct current preferably ranges between continuous to 1 MHz.

The direct current is applied for a period of time sufficient to reduce the neuronal threshold for firing under the positive electrode and/or increase the firing threshold under the negative electrode. Although not bound by a particular theory, the threshold of nerve activation is likely lowered near the positive electrode because the increase in electron density makes it easier form NMDA and other ion channels to open, and thus creates an easier presynaptic depolarization.

Figure 5A:
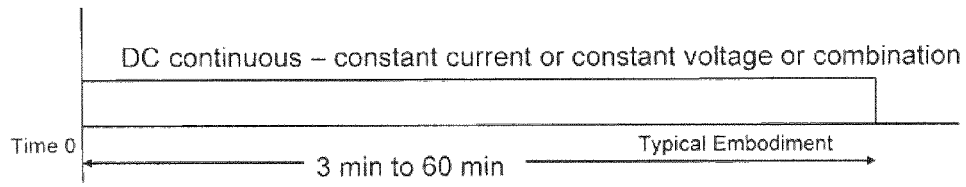
In FIG. 5A, a constant direct current is applied to the patient.

FIG. 5 illustrates the timing diagram of the transcranial direct current stimulation. In FIG. 5A, a constant direct current is applied to the patient. The direct current is a continuous current, and may be constant current or constant voltage or a combination thereof. The constant DC is usually applied for a period between 1 and 60 minutes.

Figure 5B:
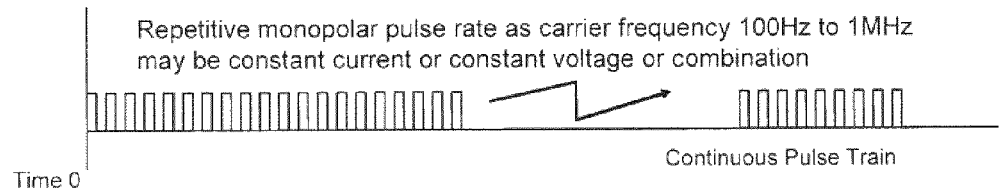
In FIG. 5B, a repetitive monopolar pulse train is applied at a suitable carrier frequency.

In FIG. 5B, the direct current stimulation waveform comprises a series of monopolar with a mid-frequency pattern applied to one or more channels of electrodes/The direct current may be constant current, constant voltage, or a combination thereof. Typically, the carrier frequency is between 100 Hz and 1 MHz.

Figure 5C:
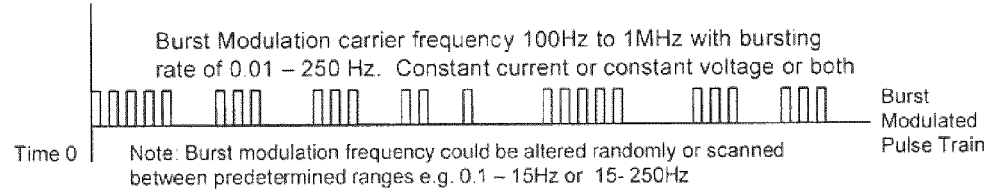
FIG. 5C is a timing diagram of a monopolar burst modulated pulse train pattern that may be applied to the output channels of the transcranial electrical stimulation device of FIG. 1B.

In FIG. 5C, the direct current stimulation waveform comprises monopolar bursts that may be applied to one or more output channels of electrodes. The frequency-sequenced pulse burst train pattern has a carrier frequency of 100 Hz to 1 MHz, with a first sequence of modulated electrical pulses generated at a burst frequency of approximately 0.01 Hz to 250 Hz. The duration of each burst ranges between approximately 1 seconds to 120 seconds, and the time between each burst ranges between 1 seconds to 120 second. The frequency may be altered randomly or set at predetermined ranges (e.g. 0.1 to 15 Hz, or 15 to 250 Hz). Preferably, the frequency-sequenced pulse burst train pattern is applied to the patient for a total treatment time of approximately 1 minute to 60 minutes.

Figure 6:
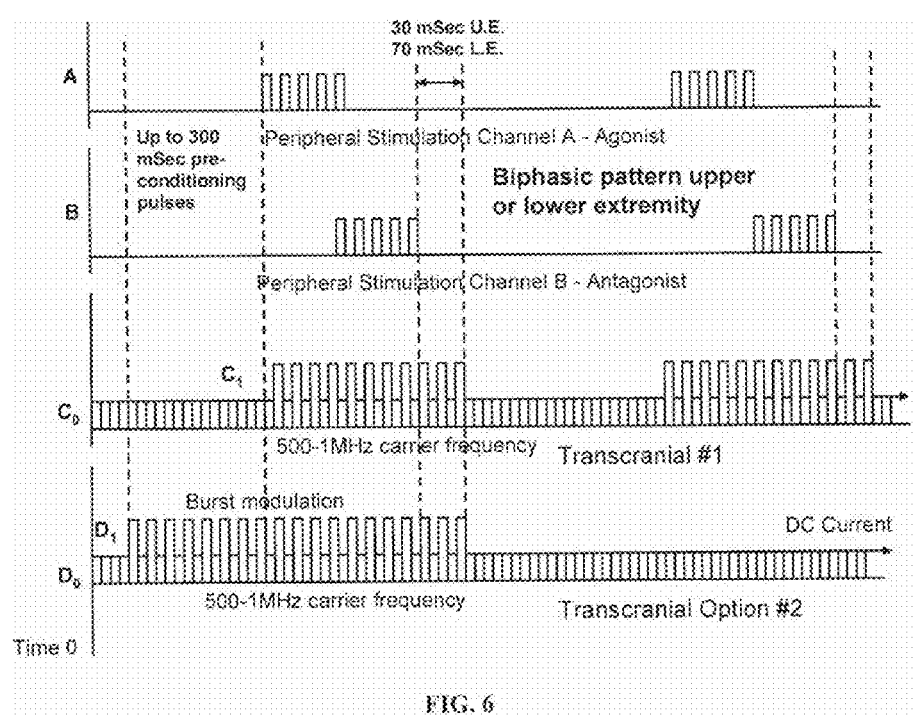
FIG. 6 is a timing diagram of an exemplary electrical stimulation system in accordance with the present invention. The top two panels illustrate an exemplary timing diagram for the neuromuscular stimulation, while the bottom two panels illustrate alternative exemplary timing diagrams for the transcranial direct current stimulation.

FIG. 6 demonstrates the an exemplary time linkage between the peripheral patterned electrical stimulation and the transcranial direct current stimulation as the latter is modulated by a carrier signal that increases its current intensity to coincide with the peripheral stimulation timing. The top two firing patterns demonstrate a prototypic biphasic peripheral stimulation timing and the third pattern demonstrates an underlying direct current flow either continuous or phasic with an increase in intensity beginning at about the same time as the peripheral stimulus and ending at or shortly after the time of the peripheral stimulation. Given the delay of nerve transmission from the upper or lower extremity to the brain, the transcortical stimulation may continue for an additional time period to allow for the peripheral to brain delay. The fourth line firing pattern demonstrates a prestimulation intensity increase that begins approximately 300 mSec before the peripheral stimulation pulses in an attempt to mimic the central neurophysiological event described as the "berieftshaftpotential" or the preactivation of the brain just prior to the activation of the motor neurons for intentional movement.

Combination Therapies

The neurological disorder treatment methods of the present invention are well-adapted to be used with other conventional therapies, including, but not limited to, changing the diet, swallowing exercises, changes in body posture, strengthening exercises, coordination exercises, and even surgery. Therapeutic agents useful for treating neurological disorders can be found in the Merck Index and the United States Pharmacopeia, which are periodically updated.

In particular, the electrical stimulation methods of the present invention may also be combined with the administration of therapeutically effective amounts of various pharmaceuticals useful for treating neurological disorders, such as dopamine uptake inhibitors, norepinephrine reuptake inhibitors, selective serotonin reuptake inhibitors, monoamine oxidase inhibitors, serotonin and noradrenaline reuptake inhibitors, norepinephrine uptake inhibitors, dopamine agonists, acetocholinesterase inhibitors, catechol O-methyltransferase inhibitors, and anticholinergic agents. Antioxidants can also be used with other neuroprotective agents as adjuncts to transcranial stimulation. The agents may be given alone or co-administered to the patient. The agents may also be administered along with pharmaceutically acceptable carriers and excipients.

Suitable antioxidants of the present invention include herbal, amino acid, mineral, vitamin, and enzymatic antioxidants. Useful, herbal antioxidants include, but are not limited to, beta carotene, various bioflavonoids (co-enzyme Q10, *curcuma, ginkgo biloba* (preferably an extract), ginseng (preferably American, Korean, or Siberian), Gotu Kola, grape pip (proanthocyanidins), and quercetin). Useful amino acid antioxidants include, but are not limited to, L-arginine. L-glutathione, L-lysine, L-methionine, L-taurine, and L-carnitine. Useful mineral antioxidants include, but are not limited to, boron, selenium (e.g., sodium selenite and selenium methionine), manganese (e.g., citrate), magnesium (preferably elemental), and zinc. Useful vitamin antioxidants include, but are not limited to, vitamins A, B, C, E, and folic acid (pteroylglutamic acid). The preferred B vitamins are $B_1$ (thiamine HCl), $B_2$ (preferably riboflavin 5'-phosphate), $B_3$ (niacinamide), $B_6$ (preferably pyridoxine HCl and activated pyridoxal 5'-phosphate), and $B_{12}$ (methylcobalamin). Other preferred vitamins are vitamin A (palminate), and vitamin E (d-alpha tocopheryl succinate). Other preferred vitamers include alpha-lipoic acid, lutein, lycopene (a carotenoid), succinate, ubiquinone (co-enzyme Q10), and zeaxanthin (a yellow carotenoid). Examples of enzymatic antioxidants include superoxide dismutase and catalase. Other forms or equivalents of these stated compounds may be utilized in alternative embodiments.

Suitable dopamine uptake inhibitors include, but are not limited to, bupropion, amineptine, phenmetrazine, methylphenidate, vanoxerine, CFT, dextropmethorphan, MDPV, and pharmaceutically acceptable salts thereof. Most preferred are bupropion (WELLBUTRIN®) and methylphenidate (RITALIN®).

Suitable norepinephrine reuptake inhibitors include, but are not limited to, tertiary amine tricyclics and secondary amine tricyclics. Suitable examples of tertiary amine tricyclics include: amitriptyline, clomipramine, doxepin, imipramine, and trimipramine, and pharmaceutically acceptable salts thereof. Suitable examples of secondary amine tricyclics include: amoxapine, desipramine, maprotiline, nortriptyline, and protriptyline, and pharmaceutically acceptable salts thereof. Another norepinephrine reuptake inhibitor of use in the present invention is reboxetine.

Suitable selective serotonin reuptake inhibitors include, but are not limited to, alaproclate, citalopram, dapoxetine, escitalopram oxalate, fluoxetine, fluvoxamine, paroxetine, sertraline, zimelidine, and pharmaceutically acceptable salts thereof.

Suitable monoamine oxidase inhibitors include, but are not limited to, harmaline, iproniazid, iproclozide, isocarboxazid, moclobemide, nialamide, pargyline, phenelzine, tranylcypromine, selegiline, toloxatone, tranylcypromine, rasagiline, many tryptamines, and pharmaceutically acceptable salts thereof. Of these, selegiline (ELDEPRYL®) is most preferred.

Suitable serotonin and noradrenaline reuptake inhibitors include, but are not limited to, desipramine, duloxetine, milnacipran, nefazodone, venlafaxine, and pharmaceutically acceptable salts thereof. Of these, venlafaxine (EFFEXOR®) is most preferred.

Suitable norepinephrine uptake inhibitors include, but are not limited to, atomoxetine, bupropion, maprotiline, reboxetine, and viloxazine.

Suitable dopamine agonists include, but are not limited to, carbidopa, levodopa, bromocriptine, pergolide, dihydroergocryptine mesylate, ropinirole, pramipexole, cabergoline, apomorphine, piribedil, rotigotine, and lisuride hydrogen maleate. Of these, carbidopa-levodopa (SINEMET®) is most preferred.

Suitable acetocholinesterase inhibitors include, but are not limited to, various organophosphates (metrifonate), carbamates (physostigmine, neostigmine, pyridostigmine, ambenonium, demarcarium, rivastigmine), phenanthrine derivatives (galantamine), peperidines (donepezil), tancrine, and edrophonium.

Suitable catechol O-methyltransferase inhibitors include, but are not limited to, entacapone and tolcapone.

Suitable anticholinergic agents include trihexyphenidyl, benzotropine, scopolamine, atropine, dicyclomine, flavoxate, ipratropium, oxybutynin, pirenzepine, tiotropium, tolterodine, tropicamide, solifenacin, solifenacin, darifenacin, atracurium, doxacurium, mivacurium, pancuronium, tuborcurarine, and vecuronium. Of these, trihexyphenidyl is most preferred.

While several exemplary embodiments of the present invention are discussed below, those skilled in the art will readily appreciate that various modifications may be made to these embodiments, and the invention is not limited to the specific electrode placements and pulse train patterns described therein.

First Exemplary Embodiment

Figure 3A:
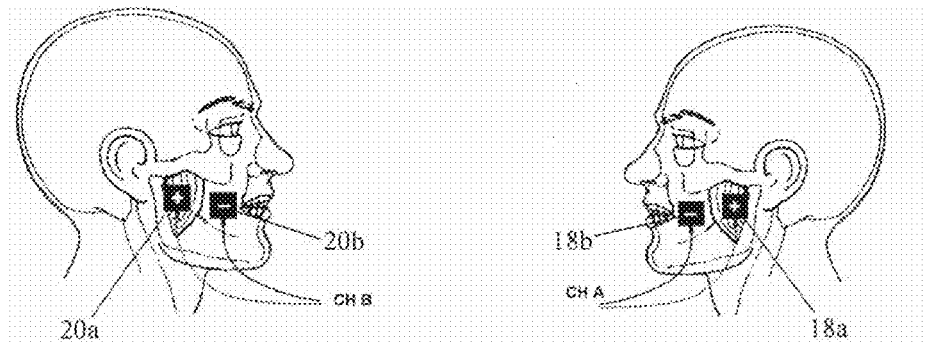
FIG. 3A illustrates a method for treating a neurological disorder in a patient by applying neuromuscular electrical stimulation in accordance with a first exemplary embodiment of the present invention, in which the facial muscles (e.g. the masseter and/or pterygoid and buccinator and/or orbicularis oris muscles) of the patient are stimulated. The neuromuscular electrical stimulation is combined with transcranial direct current electrical stimulation as generally illustrated in FIG. 4.

In a first exemplary embodiment of the present invention, as generally illustrated in FIG. 3A, a pair of electrodes is positioned in electrical contact with the patient's tissue in order to provide electrical stimulation to one or more of the face muscles. A second pair of electrodes is positioned bilaterally in a similar manner. In addition, at least one of a pair of electrodes is positioned in electrical contact of the area of the cranium overlying the brain somatosensory and motor control of the face 135a as illustrated in FIG. 4A.

More specifically, as shown in FIG. 3A, a first electrode 18a is positioned in electrical contact with tissue to stimulate a motor point of the patient's masseter muscle and/or pterygoid muscle (medial and/or lateral). Most preferably, first electrode 18a comprises a surface electrode that is positioned on the patient's skin about 1 body inch anterior to the lower angle of the mandible at the prominence of the masseter muscle, along the distal corner of the patient's mouth. A second electrode 18b is positioned is electrical contact with tissue to stimulate the patient's buccinators muscle and/or orbicularis oris muscle. Most preferably, second electrode 18b comprises a surface electrode that is positioned on the patient's skin at the distal corner of the mouth. Another pair of electrodes 20a, 20b is provided bilaterally in a similar position as generally illustrated in FIG. 3A.

In this exemplary embodiment, the pulse train pattern applied to the facial muscles comprises a biphasic overlapping pulse train pattern having the following parameters:
Pulse duration of individual electrical pulses: 50-70 microseconds
Current amplitude of individual electrical pulses: 25-70 milliamps
Duration of first phase: 100 milliseconds
Duration of overlap: 20 milliseconds
Duration of second phase: 100 milliseconds
Frequency of pulse train pattern: 1.6 hertz
Total treatment time: 20 minutes
Total number of treatments: 18 (over six weeks)
Frequency of individual electrical pulses (in each phase): 50 hertz In this exemplary embodiment, a continuous direct or pulsed direct current of approximately 1 mA with a current density of greater than 0.015 mA/cm$^2$ is simultaneously applied transcranially to the brain somatosensory and motor cortex region controlling the facial muscles 135a.

Second Exemplary Embodiment

Figure 3B:
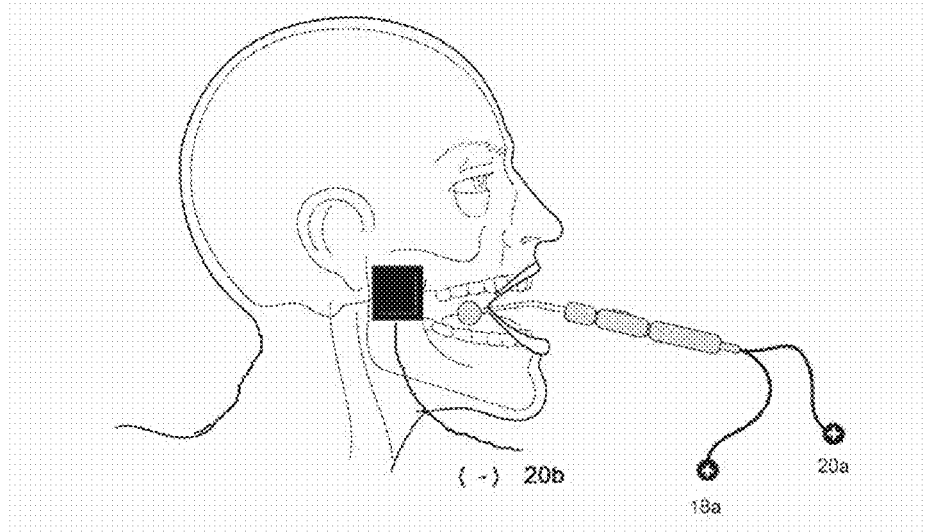
FIG. 3B illustrates a method for treating a neurological disorder in a patient by applying neuromuscular electrical stimulation in accordance with a second exemplary embodiment of the present invention, in which the facial muscles (e.g. the buccinator and/or orbicularis oris and masseter muscles) and the tongue and/or pharynx of the patient are stimulated. The neuromuscular electrical stimulation is combined with transcranial direct current electrical stimulation as generally illustrated in FIG. 4.

In a second exemplary embodiment of the present invention, as generally illustrated in FIG. 3B, a pair of electrodes is positioned in electrical contact with the patient's tissue in order to provide electrical stimulation to one or more portions of the tongue to improve motor control of the tongue and to the muscles associated with chewing and/or swallowing. A second pair of electrodes is positioned bilaterally in a similar manner. In addition, at least one of a pair of electrodes is positioned in electrical contact of the area of the cranium overlying the brain somatosensory and motor control of the face 135a as illustrated in FIG. 4A.

More specifically, as shown in FIG. 3B, a first electrode 18a is positioned in electrical contact with tissue to stimulate a motor point of the patient's tongue. Most preferably, first electrode 18a comprises a surface electrode that is positioned on the patient's skin tongue or pharynx. A second electrode 18b is positioned is electrical contact with tissue to stimulate the patient's masseter and/or facial muscles. Most preferably, second electrode 18b comprises a surface electrode that is positioned in electrical contact with tissue to simulate a motor point of the patient's masseter muscle and/or buccinators muscle and/or orbicularis oris muscle. Most preferably, second electrode 18b comprises a surface electrode that is positioned on the patient's skin along the jaw about one inch anterior to the lower angle of the mandible at the prominence of the masseter muscle or over the motor point of the patient's buccinator muscle and/or orbicularis oris muscle. Another pair of electrodes 20a, 20b is provided bilaterally in a similar position as generally illustrated in FIG. 3B.

In this exemplary embodiment, the pulse train pattern comprises a biphasic overlapping pulse train pattern having the following parameters:
Pulse duration of individual electrical pulses: 50-70 microseconds Current amplitude of individual electrical pulses: 25-70 milliamps
Duration of first phase: 100 milliseconds
Duration of overlap: 20 milliseconds
Duration of second phase: 100 milliseconds
Frequency of pulse train pattern: 1.6 hertz
Total treatment time: 20 minutes
Total number of treatments: 18 (over six weeks)
Frequency of individual electrical pulses (in each phase): 50 hertz In this exemplary embodiment, a continuous direct or pulsed direct current of approximately 1 mA with a current density of greater than 0.015 mA/cm$^2$ is simultaneously applied transcranially to the brain somatosensory and motor cortex region controlling the facial muscles 135a.

Third Exemplary Embodiment

Figure 3C:
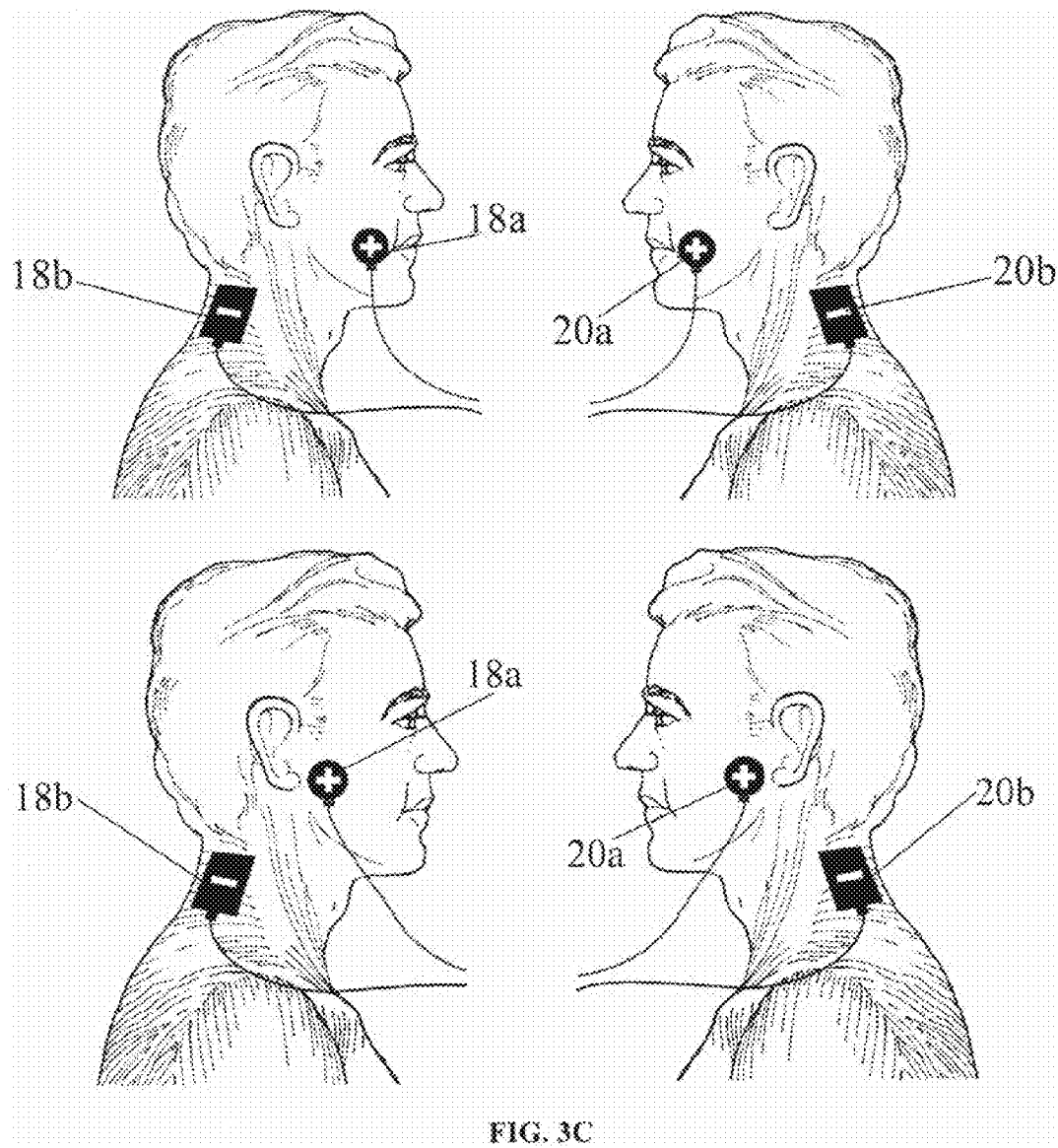
FIG. 3C (top panel) illustrates a method for treating a neurological disorder in a patient by applying neuromuscular electrical stimulation in accordance with a second exemplary embodiment of the present invention, in which the facial muscles (e.g., the buccinator and/or orbicularis oris muscles) and the cervical paraspinal muscles of the patient are stimulated. The neuromuscular electrical stimulation is combined with transcranial direct current electrical stimulation as generally illustrated in FIG. 4.

In a second exemplary embodiment of the present invention, as generally illustrated in FIG. 3C, a pair of electrodes is positioned in electrical contact with the patient's tissue in order to provide electrical stimulation to one or more of the face muscles used to create proper lip seal and to the muscles associated with the posterior neck region. A second pair of electrodes is positioned bilaterally in a similar manner. In addition, at least one of a pair of electrodes is positioned in electrical contact of the area of the cranium overlying the brain somatosensory and motor control of the face 135a as illustrated in FIG. 4A.

Figure 3D:
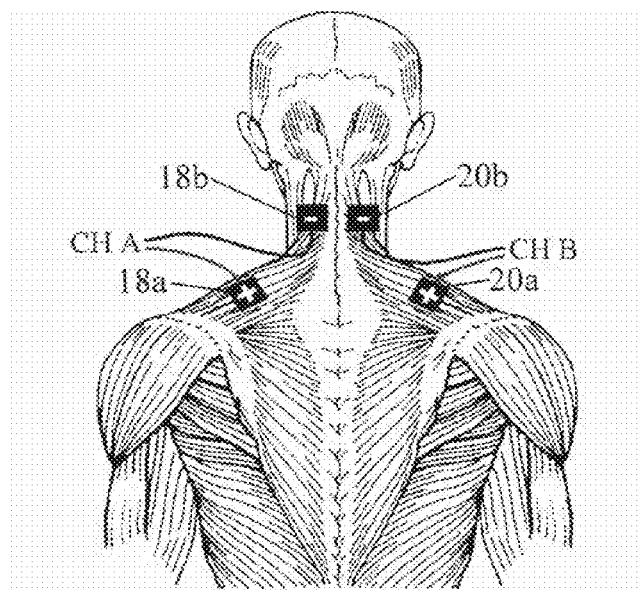
FIG. 3D illustrates a method for treating a neurological disorder in a patient by applying neuromuscular electrical stimulation in accordance with a fourth exemplary embodiment of the present invention, in which the trapezius muscles and the cervical paraspinal muscles of the patient are stimulated. The neuromuscular electrical stimulation is combined with transcranial direct current electrical stimulation as generally illustrated in FIG. 4.
Figure 3E:
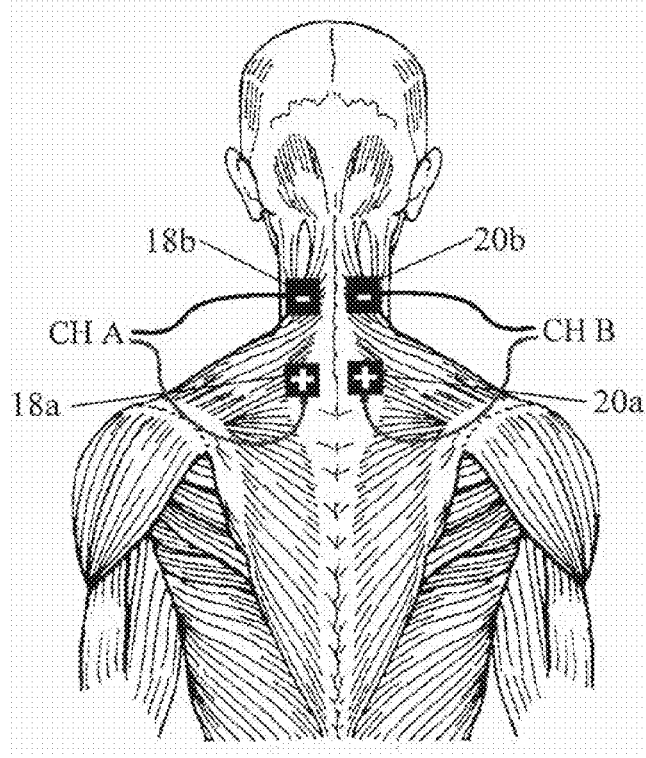
FIG. 3E illustrates a method for treating a neurological disorder in a patient by applying neuromuscular electrical stimulation in accordance with a fifth exemplary embodiment of the present invention, in which the cervical paraspinal and thoracic paraspinal muscles of the patient are stimulated. The neuromuscular electrical stimulation is combined with transcranial direct current electrical stimulation as generally illustrated in FIG. 4.
Figure 3F:
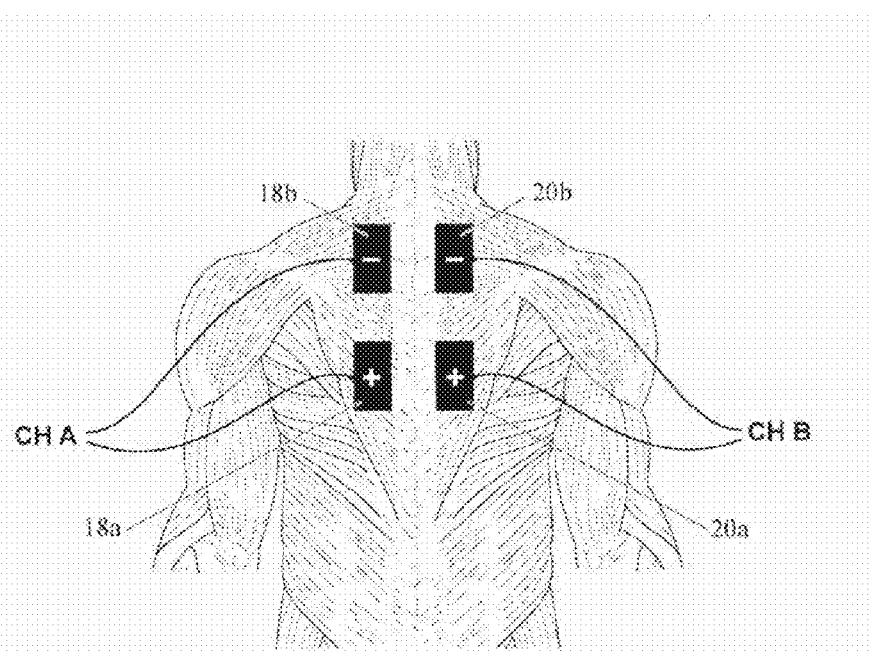
FIG. 3F illustrates a method for treating a neurological disorder in a patient by applying neuromuscular electrical stimulation in accordance with a sixth exemplary embodiment of the present invention, in which the lower cervical/upper thoracic paraspinal and mid to lower thoracic paraspinal muscles of the patient are stimulated. The neuromuscular electrical stimulation is combined with transcranial direct current electrical stimulation as generally illustrated in FIG. 4.
Figure 3G:
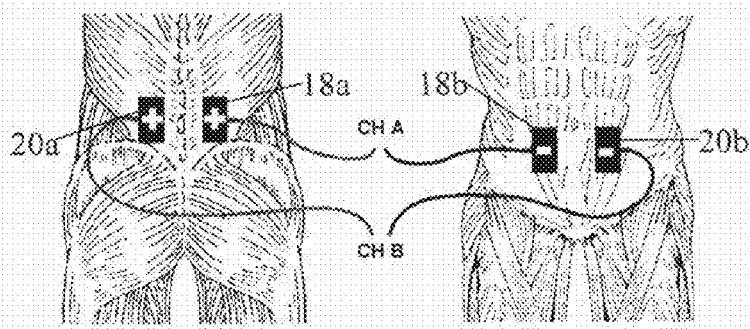
FIG. 3G illustrates a method for treating a neurological disorder in a patient by applying neuromuscular electrical stimulation in accordance with a seventh exemplary embodiment of the present invention, in which the lumbar paraspinal muscles and abdominal muscles of the patient are stimulated. The neuromuscular electrical stimulation is combined with transcranial direct current electrical stimulation as generally illustrated in FIG. 4. This embodiment is particularly useful in promoting lumbar stabilization in a patient.

More specifically, as shown in FIG. 3G, a first electrode 18a is positioned in electrical contact with tissue to stimulate a motor point of the patient's buccinator and/or orbicularis oris muscles as demonstrated in FIG. 3C (lower panel), or masseter and/or pterygoid muscles (upper panel). Most preferably, first electrode 18a comprises a surface electrode that is positioned on the patient's skin or over the motor point of the patient's buccinator muscle and/or orbicularis oris muscle. Most preferably, first electrode 18a comprises a surface electrode that is positioned on the patient's skin along the distal corner of the patient's mouth in (upper panel) or along the jaw about one inch anterior to the lower angle of the mandible at the prominence of the masseter muscle (lower panel). A second electrode 18b is positioned in electrical contact with tissue to stimulate the patient's cervical paraspinal muscles. Most preferably, second electrode 18b comprises a surface electrode that is positioned on the patient's skin in the posterior neck region just lateral to the one or more of the cervical vertebrae, most preferably near the C1, C2, C3, and/or C4 cervical vertebrae. Another pair of electrodes 20a, 20b is provided bilaterally in a similar position as generally illustrated in FIG. 3B.

In this exemplary embodiment, the pulse train pattern comprises a biphasic overlapping pulse train pattern having the following parameters:
Pulse duration of individual electrical pulses: 50-70 microseconds
Current amplitude of individual electrical pulses: 25-70 milliamps
Duration of first phase: 100 milliseconds
Duration of overlap: 20 milliseconds
Duration of second phase: 100 milliseconds
Frequency of pulse train pattern: 1.6 hertz
Total treatment time: 20 minutes
Total number of treatments: 18 (over six weeks)
Frequency of individual electrical pulses (in each phase): 50 hertz In this exemplary embodiment, a continuous direct or pulsed direct current of approximately 1 mA with a current density of greater than 0.015 mA/cm$^2$ is simultaneously applied transcranially to the brain somatosensory and motor cortex region controlling the facial muscles 135a.

Fourth Exemplary Embodiment

In a fourth exemplary embodiment of the present invention, as generally illustrated in FIG. 3D, a pair of electrodes is positioned in electrical contact with the patient's tissue in order to provide electrical stimulation to one or more of the muscles associated with swallowing in the posterior neck region and the muscles involved in maintaining proper posture during swallowing. A second pair of electrodes is positioned bilaterally in a similar manner. In addition, at least one of a pair of electrodes is positioned in electrical contact of the area of the cranium overlying the brain somatosensory and motor control of the face and neck 135 a as illustrated in FIG. 4A More specifically, as shown in FIG. 3D, a first electrode 18a is positioned in electrical contact with tissue to stimulate a motor point of the patient's upper trapezius muscle. Most preferably, first electrode 18a comprises a surface electrode that is positioned on the patient's skin along at the midpoint of the upper trapezius. A second electrode 18b is positioned is electrical contact with tissue to stimulate the patient's cervical paraspinal muscles. Most preferably, second electrode 18b comprises a surface electrode that is positioned on the patient's skin in the posterior neck region just lateral to the one or more of the cervical vertebrae, most preferably near the C1, C2, C3, and/or C4 cervical vertebrae. Another pair of electrodes 20a, 20b is provided bilaterally in a similar position as generally illustrated in FIG. 3D.

In this exemplary embodiment, the pulse train pattern comprises a biphasic overlapping pulse train pattern having the following parameters:
Pulse duration of individual electrical pulses: 50-70 microseconds
Current amplitude of individual electrical pulses: 20-70 milliamps
Duration of first phase: 100 milliseconds
Duration of overlap: 20 milliseconds
Duration of second phase: 100 milliseconds
Frequency of pulse train pattern: 1.6 hertz
Total treatment time: 20 minutes
Total number of treatments: 18 (over six weeks)
Frequency of individual electrical pulses (in each phase): 50 hertz In this exemplary embodiment, a continuous direct or pulsed direct current of approximately 1 mA with a current density of greater than 0.015 mA/cm$^2$ is simultaneously applied transcranially to the brain somatosensory and motor cortex region controlling the facial muscles 135a.

Fifth Exemplary Embodiment

In a fifth exemplary embodiment of the present invention, as generally illustrated in FIG. 3E, two pair of electrodes is positioned in electrical contact with the patient's neck. In addition, at least one of a pair of electrodes is positioned in electrical contact of the area of the cranium overlying the brain somatosensory and motor control of the face and neck 135a as illustrated in FIG. 4A. This embodiment is particularly useful for improving posture in patients suffering from a neurological disorder.

More specifically, as shown in FIG. 3E, a first electrode 18*a* is positioned in electrical contact with tissue to stimulate the patient's lower cervical and upper thoracic paraspinal muscles. Most preferably, first electrode 18*a* comprises a surface electrode that is positioned on the patient's skin along at the midpoint of the upper trapezius just lateral to the spinal cord, most preferably near the C6, C7, T1, T2, T3, and/or T4 cervical and thoracic vertebrae. A second electrode 18*b* is positioned is electrical contact with tissue to stimulate the patient's cervical paraspinal muscles. Most preferably, second electrode 18*b* comprises a surface electrode that is positioned on the patient's skin in the posterior neck region just lateral to the one or more of the cervical vertebrae, most preferably near the C1, C2, C3, and/or C4 cervical vertebrae. Another pair of electrodes 20*a*, 20*b* is provided bilaterally in a similar position as generally illustrated in FIG. 3E.

In this exemplary embodiment, the pulse train pattern comprises a biphasic overlapping pulse train pattern having the following parameters:
Pulse duration of individual electrical pulses: 50-70 microseconds
Current amplitude of individual electrical pulses: 20-70 milliamps
Duration of first phase: 100 milliseconds
Duration of overlap: 20 milliseconds
Duration of second phase: 100 milliseconds
Frequency of pulse train pattern: 1.6 hertz
Total treatment time: 20 minutes
Total number of treatments: 18 (over six weeks)
Frequency of individual electrical pulses (in each phase): 50 hertz In this exemplary embodiment, a continuous direct or pulsed direct current of approximately 1 mA with a current density of greater than 0.015 mA/cm$^2$ is simultaneously applied transcranially to the brain somatosensory and motor cortex region controlling the neck muscles 135*a*.

Sixth Exemplary Embodiment

In a sixth exemplary embodiment of the present invention, as generally illustrated in FIG. 3F, two pair of electrodes is positioned in electrical contact with the patient's mid-back or upper back. In addition, at least one of a pair of electrodes is positioned in electrical contact of the area of the cranium overlying the brain somatosensory and motor control of the mid-back and upper back 135*b* as illustrated in FIG. 4A. This embodiment is particularly useful for improving posture in patients suffering from a neurological disorder.

More specifically, as shown in FIG. 3F, the electrodes are positioned in electrical contact with the erector spinae and trapezius muscles. The first electrode 18*a* is in electrical contact with tissue to stimulate the patient's thoracic paraspinal muscles. Most preferably, second electrode 18*a* comprises a surface electrode that is positioned on the patient's skin in just lateral to the one or more of the thoracic vertebrae, most preferably near the T3, T4, T5, T6, T7, T8, and/or T9 thoracic vertebrae. A second electrode 18*b* is positioned in electrical contact with tissue to stimulate the patient's upper thoracic paraspinal muscles. Most preferably, first electrode 18*a* comprises a surface electrode that is positioned on the patient's skin along at the midpoint of the upper trapezius just lateral to the spinal cord, most preferably near the C7, T1, T2, T3, and/or T4 cervical and thoracic vertebrae. Another pair of electrodes 20*a*, 20*b* is provided bilaterally in a similar position as generally illustrated in FIG. 3F.

In this exemplary embodiment, the pulse train pattern comprises a biphasic overlapping pulse train pattern having the following parameters:
Pulse duration of individual electrical pulses: 50-70 microseconds
Current amplitude of individual electrical pulses: 20-70 milliamps
Duration of first phase: 100 milliseconds
Duration of overlap: 20 milliseconds
Duration of second phase: 100 milliseconds
Frequency of pulse train pattern: 1.6 hertz
Total treatment time: 20 minutes
Total number of treatments: 36
Frequency of individual electrical pulses (in each phase): 50 hertz In this exemplary embodiment, a continuous direct or pulsed direct current of approximately 1 mA with a current density of greater than 0.015 mA/cm$^2$ is simultaneously applied transcranially to the brain somatosensory and motor cortex region controlling the mid-back and upper back muscles 135*b*.

Seventh Exemplary Embodiment

In a seventh exemplary embodiment of the present invention, as generally illustrated in FIG. 3G, a pair of electrodes is positioned in electrical contact with the patient's tissue in order to provide electrical stimulation to one or more of the muscles associated with lumbar stabilization. A second pair of electrodes is positioned bilaterally in a similar manner. In addition, at least one of a pair of electrodes is positioned in electrical contact of the area of the cranium overlying the brain somatosensory and motor control of the trunk 135*c* as illustrated in FIG. 4A.

More specifically, as shown in FIG. 3G, a first electrode 18*a* is positioned in electrical contact with the tissue of the patient's lumbar region. Most preferably, first electrode 18*a* comprises a surface electrode that is positioned posteriorly on the patient's skin in the lower back region over the lower paraspinal muscles just lateral to one or more of the lower thoracic and/or lumbar vertebrae, most preferably near the L1, L2, L3, L4, and/or L5 lumbar vertebrae. A second electrode 18*b* is positioned is electrical contact with tissue to stimulate the patient's abdominal muscles. Most preferably, second electrode 18*b* comprises a surface electrode that is positioned anteriorly on the patient's skin at about the level of the umbilicus, about half-way between the anterior superior iliac spine ("ASIS") and the anterior midline over the combined abdominal muscle. Another pair of electrodes 20*a*, 20*b* is provided bilaterally in a similar position as generally illustrated in FIG. 3G.

In this exemplary embodiment, the pulse train pattern comprises a triphasic overlapping pulse train pattern having the following parameters:
Pulse duration of individual electrical pulses: 50-70 microseconds
Current amplitude of individual electrical pulses: 20-90 milliamps
Duration of first phase: 200 milliseconds
Duration of overlap: 40 milliseconds
Duration of second phase: 200 milliseconds
Duration of overlap: 40 milliseconds
Duration of third phase: 120 milliseconds
Frequency of pulse train pattern: 0.67 hertz
Frequency of individual electrical pulses (in each phase): 50 hertz
Total treatment time: 20 minutes Total number of treatments: 18 (over six weeks)

In this exemplary embodiment, a continuous direct or pulsed direct current of approximately 1 mA with a current density of greater than 0.015 mA/cm$^2$ is simultaneously applied transcranially to the brain somatosensory and motor cortex region controlling the lumbar and abdominal muscles 135c.

Eighth Exemplary Embodiment

Figure 3H:
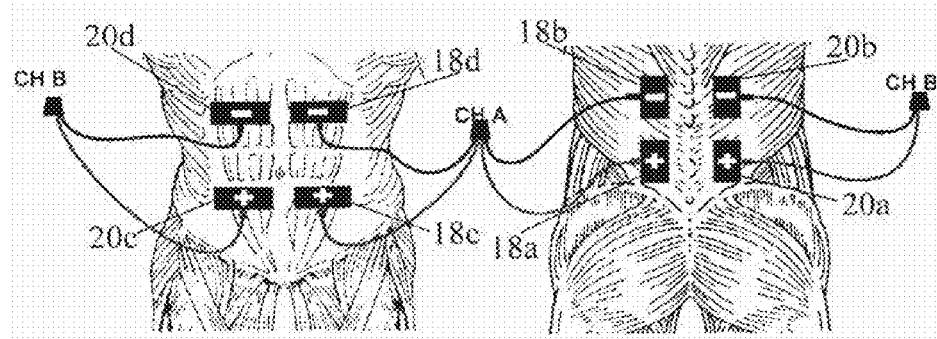
FIG. 3H illustrates a method for treating a neurological disorder in a patient by applying neuromuscular electrical stimulation in accordance with an eighth exemplary embodiment of the present invention, in which the thoracic and/or lumbar paraspinal muscles and abdominal muscles of the patient are stimulated. The neuromuscular electrical stimulation is combined with transcranial direct current electrical stimulation as generally illustrated in FIG. 4. This embodiment is particularly useful in promoting trunk flexion/extension in a patient.

In an eighth exemplary embodiment of the present invention, as generally illustrated in FIG. 3H, four pairs of electrodes are positioned in electrical contact with the patient's tissue in order to provide electrical stimulation to one or more of the muscles involved in trunk flexion and extension. Two channels may be used with a bifurcating cable as illustrated in FIG. 3H.

More specifically, as shown in FIG. 3H, a first electrode 18a is positioned in electrical contact with the tissue of the patient's upper lumbar and upper abdominal region. Most preferably, first electrode 18a comprises a surface electrode that is positioned posteriorly on the patient's skin in the lower back region over the multifidus muscle, just lateral to one or more of the lower thoracic and/or lumbar vertebrae, most preferably near the L1, L2, L3, L4, and/or L5 lumbar vertebrae. The second electrode 18b of the first channel is also placed posteriorly on the patient's skin in the lower back region over the multifidus muscle, just lateral to one or more of the lower thoracic and/or lumbar vertebrae, most preferably near the T9, T10, T11. T12, L1, L2, and/or L3 lumbar vertebrae. A third electrode 18c and fourth electrode 18d are placed over the same side abdominal muscles at the same vertebral level to stimulate the patient's lower abdominal muscles. Another set of four electrodes 20a, 20b, 20c, and 20d are provided bilaterally in a similar position as generally illustrated in FIG. 3H.

In this exemplary embodiment, the pulse train pattern comprises a triphasic overlapping pulse train pattern having the following parameters:
Pulse duration of individual electrical pulses: 50-70 microseconds
Current amplitude of individual electrical pulses: 20-70 milliamps
Duration of first phase: 200 milliseconds
Duration of overlap: 40 milliseconds
Duration of second phase: 200 milliseconds
Duration of overlap: 40 milliseconds
Duration of third phase: 120 milliseconds
Frequency of pulse train pattern: 0.67 hertz
Frequency of individual electrical pulses (in each phase): 50 hertz
Total treatment time: 20 minutes
Total number of treatments: 18 (over six weeks)

in this exemplary embodiment, a continuous direct or pulsed direct current of approximately 1 mA with a current density of greater than 0.015 ma/cm$^2$ is simultaneously applied transcranially to the brain somatosensory and motor cortex region controlling the lumbar and abdominal muscles 135c.

Ninth Exemplary Embodiment

Figure 3I:
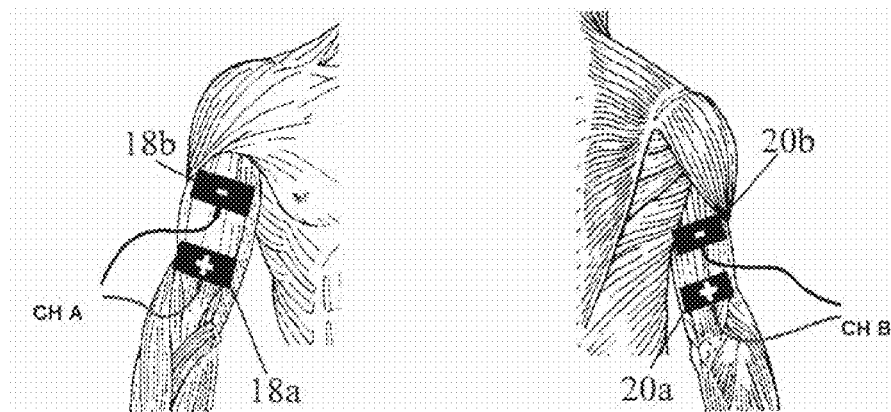
FIG. 3I illustrates a method for treating a neurological disorder in a patient by applying neuromuscular electrical stimulation in accordance with a ninth exemplary embodiment of the present invention, in which the biceps brachii and triceps brachii muscles of the patient are stimulated. The neuromuscular electrical stimulation is combined with transcranial direct current electrical stimulation as generally illustrated in FIG. 4. This embodiment is particularly useful in promoting arm flexion/extension in a patient.

In a ninth exemplary embodiment of the present invention, as generally illustrated in FIG. 3I, a pair of electrodes is positioned in electrical contact with the patient's tissue in order to provide electrical stimulation to one or more of the muscles involved in the elbow flexion. A second pair of electrodes is positioned in electrical contact with the patient's tissue in order to provide stimulation to one or more of the muscles involved in elbow extension. In addition, at least one of a pair of electrodes is positioned in electrical contact of the area of the cranium overlying the brain somatosensory and motor control of the upper extremity 135b as illustrated in FIG. 4A.

More specifically, as shown in FIG. 3I, first and second electrodes 18a, 18b are positioned in electrical contact with tissue to stimulate the biceps brachii muscle of the patient. Most preferably, first electrode 18a comprises a surface electrode that is positioned on the patient's skin anteriorly on the upper arm above the biceps brachii muscle insertion. Most preferably, the second electrode 18b comprises a surface electrode that is positioned anteriorly on the patient's skin on the upper arm just below the biceps brachii muscle origin. Another pair of electrodes 20a, 20b is provided in electrical contact with tissue to stimulate the triceps brachii muscle of the patient. Most preferably, first electrode 20a comprises a surface electrode that is positioned posteriorly on the patient's skin on the upper arm above the triceps brachii muscle insertion. Most preferably, the second electrode 20b comprises a surface electrode that is positioned on the patient's skin on the upper arm just above the triceps brachii muscle origin.

During treatment, the first and second channels are positioned on the right or left arm, and a patterned pulse train is applied as discussed more fully below. It will be appreciated that the muscles involved in elbow flexion and extension may be bilaterally stimulated when the electrical stimulation device contains at least four channels. Alternatively, two electrical stimulation devices can be used for bilateral stimulation: one to simulate the right arm, and one to stimulate the left arm such as for stimulation of the bilateral biceps or triceps in a reciprocating functional pattern similar to FIG. 3N.

In this exemplary embodiment, the pulse train pattern comprises a triphasic overlapping pulse train pattern having the following parameters:
Pulse duration of individual electrical pulses: 50-70 microseconds.
Current amplitude of individual electrical pulses: 30-70 milliamps
Duration of first phase: 100 milliseconds
Duration of overlap: 20 milliseconds
Duration of second phase: 100 milliseconds
Duration of overlap: 20 milliseconds
Duration of third phase: 60 milliseconds
Frequency of pulse train pattern: 0.67 seconds
Total treatment time: 20 minutes
Total number of treatments: 18 (over six weeks)
Frequency of individual electrical pulses (in each phase): 50 hertz In this exemplary embodiment, a continuous direct or pulsed direct current of approximately 1 mA with a current density of greater than 0.015 ma/cm$^2$ is simultaneously applied transcranially to the brain somatosensory and motor cortex region controlling the upper extremities 135b.

Tenth Exemplary Embodiment

Figure 3J:
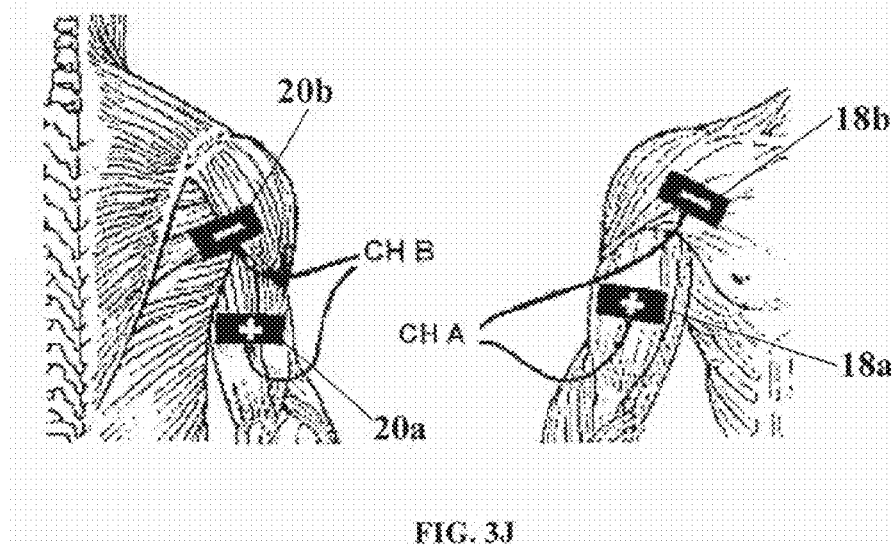
FIG. 3J illustrates a method for treating a neurological disorder in a patient by applying neuromuscular electrical stimulation in accordance with a tenth exemplary embodiment of the present invention, in which the muscles associated with shoulder internal and external rotation are stimulated. The neuromuscular electrical stimulation is combined with transcranial direct current electrical stimulation as generally illustrated in FIG. 4.
Figure 3K:
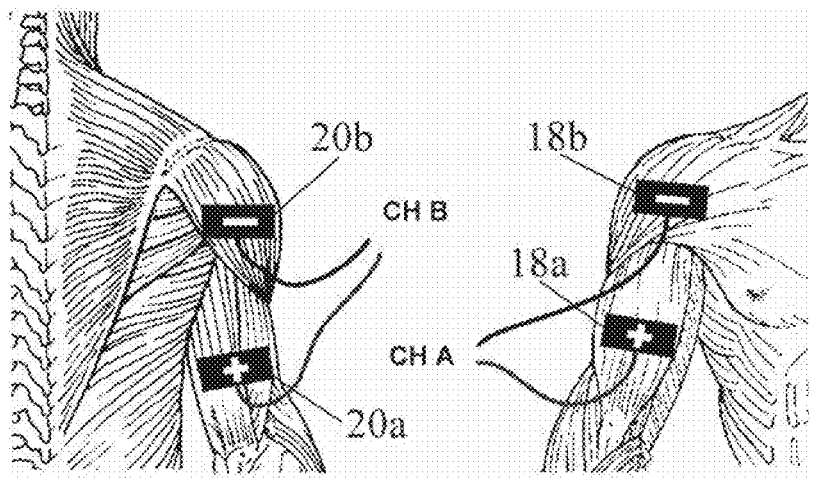
FIG. 3K illustrates a method for treating a neurological disorder in a patient by applying neuromuscular electrical stimulation in accordance with an eleventh exemplary embodiment of the present invention, in which the muscles associated with shoulder flexion and extension are stimulated. The neuromuscular electrical stimulation is combined with transcranial direct current electrical stimulation as generally illustrated in FIG. 4.

In a tenth exemplary embodiment of the present invention, as generally illustrated in FIG. 3J, two pairs of electrodes are positioned in electrical contact with the patient's tissue in order to provide electrical stimulation to one or more of the muscles involved in the internal and external rotation of the shoulder. In addition, at least one of a pair of electrodes is positioned in electrical contact of the area of the cranium overlying the brain somatosensory and motor control of the upper extremity 135b as illustrated in FIG. 4A.

More specifically, as shown in FIG. 3J, first pair of electrodes 18a, 18b are provided to provide simulation to muscles involved in the internal rotation of the shoulder. A first electrode 18a is positioned in electrical contact with tissue to stimulate the biceps brachii muscle. Most preferably, first electrode 18a comprises a surface electrode that is positioned on the patient's skin near the midpoint of the biceps brachii muscle. A second electrode 18b is positioned is electrical contact with tissue to stimulate the patient's pectoralis major and anterior deltoid muscle. Most preferably, second electrode 18b comprises a surface electrode that is positioned anteriorly on the patient's skin just above the axilla.

Another pair of electrodes 20a, 20b is provided to stimulate the muscles involved in the external rotation of the shoulder. A first electrode 20a is positioned in electrical contact with tissue to stimulate the triceps brachi muscle. Most preferably, first electrode 20a comprises a surface electrode that is positioned in near the midpoint of the triceps brachii. A second electrode 20b is positioned is electrical contact with tissue to stimulate the infraspinatus teres minor and the posterior deltoid muscle. Most preferably, second electrode 20b comprises a surface electrode that is positioned posteriorly on the patient's skin just above the underarm.

During treatment, the first and second channels are positioned on the right or left arm, and a patterned pulse train is applied as discussed more fully below. It will be appreciated that the muscles involved in shoulder rotation may be bilaterally stimulated when the electrical stimulation device contains at least four channels. Alternatively, two electrical stimulation devices can be used for bilateral stimulation: one to simulate the right shoulder, and one to stimulate the left shoulder.

In this exemplary embodiment, the pulse train pattern comprises a triphasic overlapping pulse train pattern having the following parameters:
Pulse duration of individual electrical pulses: 50-70 microseconds
Current amplitude of individual electrical pulses: 30-70 milliamps
Duration of first phase: 100 milliseconds
Duration of overlap: 20 milliseconds
Duration of second phase: 100 milliseconds
Duration of overlap: 20 milliseconds
Duration of third phase: 60 milliseconds
Frequency of pulse train pattern: 0.67 hertz
Total treatment time: 20 minutes
Total number of treatments: 18 (over six weeks)
Frequency of individual electrical pulses (in each phase): 50 hertz In this exemplary embodiment, a continuous direct or pulsed direct current of approximately 1 mA with a current density of greater than 0.015 ma/cm$^2$ is simultaneously applied transcranially to the brain somatosensory and motor cortex region controlling the upper extremities 135b.

Eleventh Exemplary Embodiment

In an eleventh exemplary embodiment of the present invention, as generally illustrated in FIG. 3J, two pairs of electrodes are positioned in electrical contact with the patient's tissue in order to provide electrical stimulation to one or more of the muscles involved in the flexion and extension of the shoulder and elbow. In addition, at least one of a pair of electrodes is positioned in electrical contact of the area of the cranium overlying the brain somatosensory and motor control of the upper extremity 135b as illustrated in FIG. 4A

More specifically, as shown in FIG. 3J, first pair of electrodes 18a, 18b are provided to provide simulation to muscles involved in the flexion of the shoulder and elbow. A first electrode 18a is positioned in electrical contact with tissue to stimulate the biceps brachii muscle. Most preferably, first electrode 18a comprises a surface electrode that is positioned on the patient's skin near the midpoint of the biceps brachii muscle. A second electrode 18b is positioned is electrical contact with tissue to stimulate the patient's anterior deltoid muscle. Most preferably, second electrode 18b comprises a surface electrode that is positioned anteriorly on the patient's skin just above the axilla.

Another pair of electrodes 20a, 20b is provided to stimulate the muscles involved in the extension of the shoulder. A first electrode 20a is positioned in electrical contact with tissue to stimulate the triceps brachi muscle. Most preferably, first electrode 20a comprises a surface electrode that is positioned in near the distal end of the triceps brachii. A second electrode 20b is positioned is electrical contact with tissue to stimulate the posterior deltoid muscle. Most preferably, second electrode 20b comprises a surface electrode that is positioned posteriorly on the patient's skin just above the axilla.

During treatment, the first and second channels are positioned on the right or left arm, and a patterned pulse train is applied as discussed more fully below. It will be appreciated that the muscles involved in shoulder rotation may be bilaterally stimulated when the electrical stimulation device contains at least four channels. Alternatively, two electrical stimulation devices can be used for bilateral stimulation: one to simulate the right shoulder, and one to stimulate the left shoulder.

In this exemplary embodiment, the pulse train pattern comprises a triphasic overlapping pulse train pattern having the following parameters:
Pulse duration of individual electrical pulses: 50-70 microseconds
Current amplitude of individual electrical pulses: 30-70 milliamps
Duration of first phase: 100 milliseconds
Duration of overlap: 20 milliseconds
Duration of second phase: 100 milliseconds
Duration of overlap: 20 milliseconds
Duration of third phase: 60 milliseconds
Frequency of pulse train pattern: 0.67 hertz
Total treatment time: 20 minutes
Total number of treatments: 18 (over six weeks)
Frequency of individual electrical pulses (in each phase): 50 hertz In this exemplary embodiment, a continuous direct or pulsed direct current of approximately 1 mA with a current density of greater than 0.015 ma/cm$^2$ is simultaneously applied transcranially to the brain somatosensory and motor cortex region controlling the upper extremities 135b.

Twelfth Exemplary Embodiment

Figure 3L:
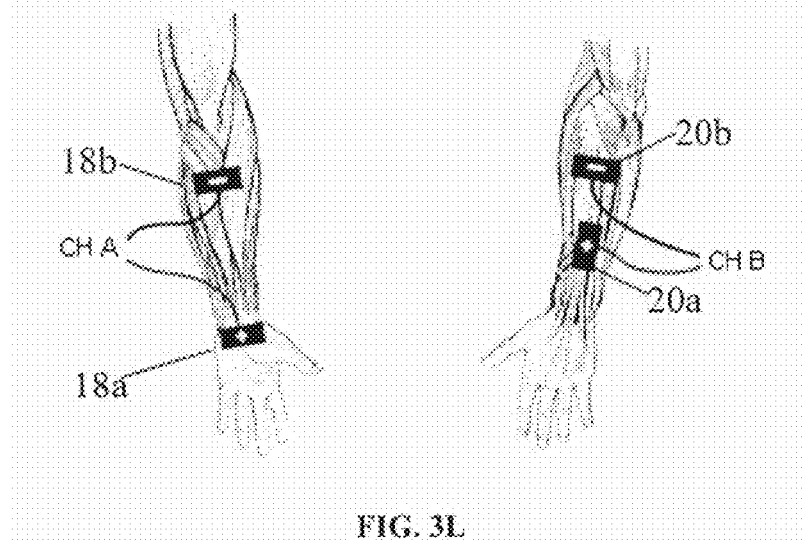
FIG. 3L illustrates a method for treating a neurological disorder in a patient by applying neuromuscular electrical stimulation in accordance with a twelfth exemplary embodiment of the present invention, in which the muscles associated with wrist and finger flexion and extension are stimulated. The neuromuscular electrical stimulation is combined with transcranial direct current electrical stimulation as generally illustrated in FIG. 4.

In an twelfth exemplary embodiment of the present invention, also generally illustrated in FIG. 3L, a pair of electrodes is positioned in electrical contact with the patient's tissue in order to provide electrical stimulation to one or more of the muscles associated with wrist flexion, extension, pronation and supination and extension and/or finger flexion and extension as a treatment for neurological disorders in the upper extremities. The treated muscles include the flexor digitorum superficialis, flexor carpi radialis, flexor carpi ulnaris, extensor digitorum, extensor digiti minimi muscle, extensor carpi ulnaris, extensor carpi radialis longus, and/or extensor carpi radialis brevis. In addition, at least one of a pair of electrodes is positioned in electrical contact of the area of the cranium overlying the brain somatosensory and motor control of the upper extremity 135b as illustrated in FIG. 4A.

More specifically, as generally shown in FIG. 3L, a two-channel system is used to apply electrical stimulation to muscles of the wrist and fingers. In the first channel, a first electrode 18a is positioned in electrical contact with tissue of the proximal palmar surface to stimulate the hand intrinsic muscles. Most preferably, first electrode 18a comprises a surface electrode that is positioned on the patient's skin across the thenar and the hypothenar eminence on the palmar/anterior side of the forearm at the base of the wrist just below the wrist crease. A second electrode is positioned in electrical contact with tissue to stimulate the muscles of the volar surface of the proximal forearm. Most preferably, second electrode 18b comprises a surface electrode that is positioned on the patient's skin on the palmar/anterior side of lower arm just below the elbow joint.

For the second channel, the first electrode 20a is positioned in electrical contact with a tissue to stimulate a motor point of the patient's extensor digitorum and pollicis muscles. Most preferably, first electrode 20a comprises a surface electrode that is positioned on the patient's skin on the dorsal/posterior side of the lower arm about ⅓ of the way between the wrist crease and elbow joint. The second electrode 20b is positioned in electrical contact with tissue to stimulate a motor point of the patient's proximal extensor muscles of the forearm. Most preferably, second electrode 20b comprises a surface electrode that is positioned on the patient's skin on the dorsal/posterior side of the lower arm just below the elbow joint.

During treatment, the first and second channels are positioned on the right or left arm, and a patterned pulse train is applied to the arm and wrist as discussed more fully below. It will be appreciated that the muscles involved in wrist extension and flexion may be bilaterally stimulated when the electrical stimulation device contains at least four channels. Alternatively, two electrical stimulation devices can be used for bilateral stimulation: one to simulate the right wrist and fingers, and one to stimulate the left wrist and fingers.

In this exemplary embodiment, the pulse train pattern comprises a triphasic overlapping pulse train pattern having the following parameters:
Pulse duration of individual electrical pulses: 50-70 microseconds
Current amplitude of individual electrical pulses: 30-70 milliamps
Duration of first phase: 100 milliseconds
Duration of overlap: 20 milliseconds
Duration of second phase: 100 milliseconds
Duration of overlap: 20 milliseconds
Duration of third phase: 60 milliseconds
Frequency of pulse train pattern: 0.67 hertz
Total treatment time: 20 minutes
Total number of treatments: 18 (over six weeks)
Frequency of individual electrical pulses (in each phase): 50 hertz In this exemplary embodiment, a continuous direct or pulsed direct current of approximately 1 mA with a current density of greater than 0.015 ma/cm$^2$ is simultaneously applied transcranially to the brain somatosensory and motor cortex region controlling the upper extremities 135b.

Thirteenth Exemplary Embodiment

Figure 3M:
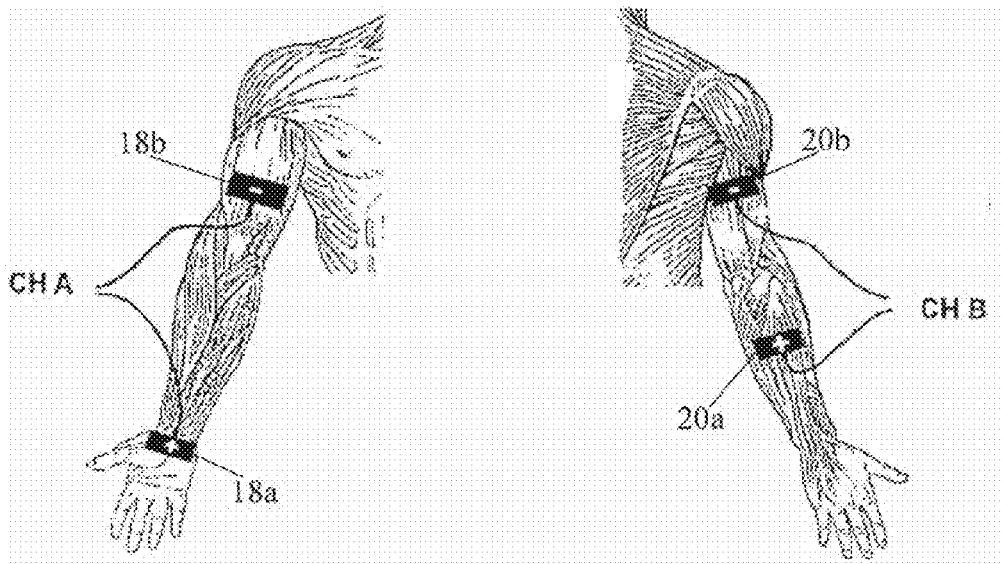
FIG. 3M illustrates a method for treating a neurological disorder in a patient by applying neuromuscular electrical stimulation in accordance with a thirteenth exemplary embodiment of the present invention, in which the muscles associated with upper extremity motor control are stimulated. The neuromuscular electrical stimulation is combined with transcranial direct current electrical stimulation as generally illustrated in FIG. 4.

In a thirteenth exemplary embodiment of the present invention, as generally illustrated in FIG. 3M, two pairs pair of electrodes are positioned in electrical contact with the patient's tissue in order to provide electrical stimulation to one or more of the muscles involved in movements of the upper extremities.

More specifically, as shown in FIG. 3M, first pair of electrodes 18a, 18b are provided to provide simulation to the anterior portion of the arm. A first electrode 18a is positioned in electrical contact with tissue of the proximal palmar surface to stimulate the hand intrinsic muscles. Most preferably, first electrode 18a comprises a surface electrode that is positioned on the patient's skin across the thenar and the hypothenar eminence on the palmar/anterior side of the forearm at the base of the wrist just below the wrist crease. A second electrode 18b is positioned is electrical contact with tissue to stimulate the patient's biceps brachii muscles and median and ulnar nerves. Most preferably, second electrode 18b comprises a surface electrode that is positioned anterior and medially (to capture the median and ulnar nerve bundle) on the patient's skin near the midpoint of the biceps brachii muscle.

Another pair of electrodes 20a, 20b is provided to stimulate the posterior muscles of the arm. The first electrode 20a is positioned in electrical contact with tissue to stimulate a motor point of the patient's proximal extensor muscles of the forearm. Most preferably, first electrode 20a comprises a surface electrode that is positioned on the patient's skin on the dorsal/posterior side of the lower arm just below the elbow joint A second electrode 20b is positioned is electrical contact with tissue to stimulate the patient's triceps brachii muscles. Most preferably, second electrode 20b comprises a surface electrode that is positioned posteriorly on the patient's skin near the midpoint of the triceps brachii muscle.

During treatment, the first and second channels are positioned on the right or left arm, and a patterned pulse train is applied to the arm and wrist as discussed more fully below. It will be appreciated that the muscles involved in arm movement may be bilaterally stimulated when the electrical stimulation device contains at least four channels. Alternatively, two electrical stimulation devices can be used for bilateral stimulation: one to simulate the right wrist and lingers, and one to stimulate the left wrist and lingers.

In this exemplary embodiment, the pulse train pattern comprises a triphasic overlapping pulse train pattern having the following parameters:
Pulse duration of individual electrical pulses: 50-70 microseconds
Current amplitude of individual electrical pulses: 30-70 milliamps
Duration of first phase: 100 milliseconds
Duration of overlap: 20 milliseconds
Duration of second phase: 100 milliseconds
Duration of overlap: 20 milliseconds
Duration of third phase: 60 milliseconds
Frequency of pulse train pattern: 0.67 hertz
Total treatment time: 20 minutes
Total number of treatments: 18 (over six weeks)
Frequency of individual electrical pulses (in each phase): 50 hertz In this exemplary embodiment, a continuous direct or pulsed direct current of approximately 1 mA with a current density of greater than 0.015 ma/cm$^2$ is simultaneously applied transcranially to the brain somatosensory and motor cortex-region controlling the upper extremities 135b.

Fourteenth Exemplary Embodiment

Figure 3N:
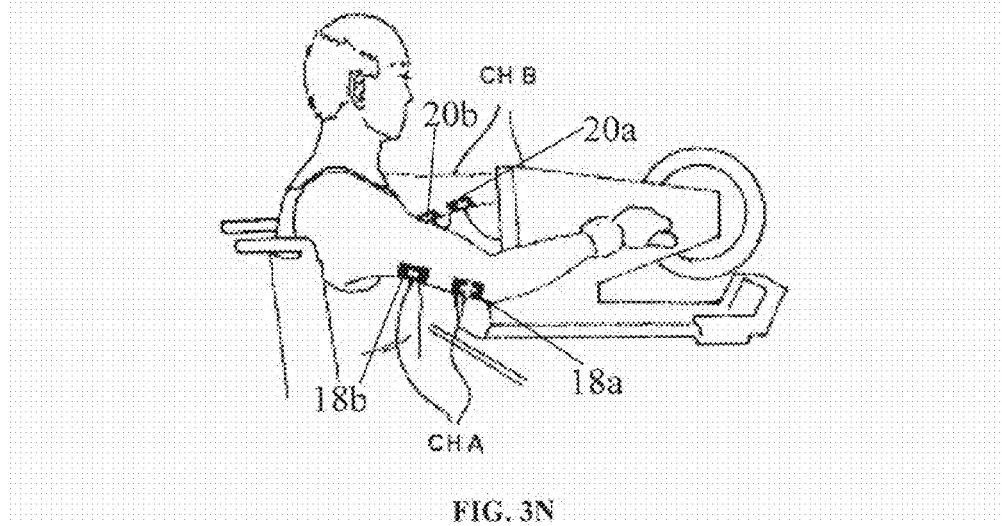
FIG. 3N illustrates a method for treating a neurological disorder in a patient by applying neuromuscular electrical stimulation in accordance with a fourteenth exemplary embodiment of the present invention, in which the triceps brachii muscles are stimulated during a physical activity, such as cycling. The neuromuscular electrical stimulation is combined with transcranial direct current electrical stimulation as generally illustrated in FIG. 4.

In a fourteenth exemplary embodiment of the present invention, as generally illustrated in FIG. 3N, two pairs of electrodes are positioned in electrical contact with the patient's tissue in order to provide electrical stimulation to the patient's triceps brachii muscles. In addition, at least one of a pair of electrodes is positioned in electrical contact of the area of the cranium overlying the brain somatosensory and motor control of the upper extremity 135b as illustrated in FIG. 4A. An alternative placement is illustrated in FIG. 4D using a two channel stimulator placed bilaterally over the brain somatosensory and motor control of the upper extremity 135b. The patient is preferably instructed to participate in alternating reciprocal movements during treatment, such as those involved in cycling.

More specifically, as shown in FIG. 3N, first and second electrodes 18a, 18b are positioned in electrical contact with tissue to stimulate the triceps brachii muscle of the patient. Another pair of electrodes 20a, 20b is provided in electrical contact with tissue to stimulate the other triceps brachii muscle of the patient.

In this exemplary embodiment, the pulse train pattern comprises a functional pulse train pattern having the following parameters:
Pulse duration of individual electrical pulses: 50-70 microseconds
Current amplitude of individual electrical pulses: 30-70 milliamps
Duration of first phase: 200 milliseconds
Duration of delay: 300 milliseconds
Duration of second phase: 200 milliseconds
Duration of delay: 300 milliseconds
Frequency of pulse train pattern: 1.0 hertz
Total treatment time: 10-20 minutes
Total number of treatments: 18 (over six weeks)
Frequency of individual electrical pulses (in each phase): 50 hertz In this exemplary embodiment, a continuous direct or pulsed direct current of approximately 1 mA with a current density of greater than 0.015 ma/cm² is simultaneously applied transcranially to the brain somatosensory and motor cortex region controlling the upper extremities 135b either unilaterally as in FIG. 4A or bilaterally as in FIG. 4D. The timing parameters to be adjusted for the desired speed or cycles per minute. The current embodiment demonstrates timing pattern for upper extremity cycling at 1 Hz.

Fifteenth Exemplary Embodiment

Figure 3O:
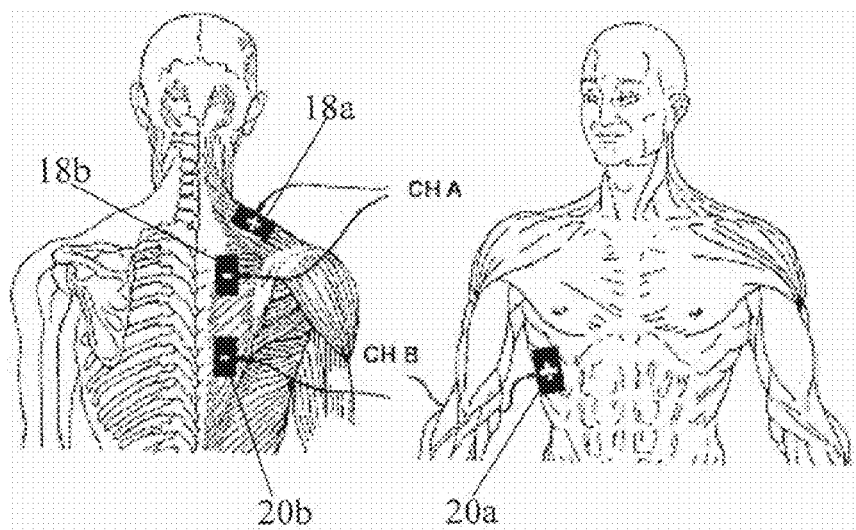
FIG. 3O illustrates a method for treating a neurological disorder in a patient by applying neuromuscular electrical stimulation in accordance with a fifteenth exemplary embodiment of the present invention, in which the muscles associated with scapular abduction and upward rotation are stimulated. The neuromuscular electrical stimulation is combined with transcranial direct current electrical stimulation as generally illustrated in FIG. 4.

In a fifteenth exemplary embodiment of the present invention, as shown in FIG. 3O, two pairs of electrodes are positioned in electrical contact with the patient's tissue in order to provide electrical stimulation to one or more of the muscles involved in movements of the scapula, specifically scapular abduction and upward rotation.

More specifically, as shown in FIG. 3O, first pair of electrodes 18a, 18b are applied to provide simulation to the upper and mid trapezius and rhomboids. Most preferably, first electrode 18a comprises a surface electrode that is positioned on the patient's skin across the midpoint of the upper trapezius, and the second electrode 18b comprises a surface electrode that is positioned on the patient's skin to stimulate the trapezius and lower cervical and upper thoracic paraspinal muscles near the C6, C7, T1, T2, T3, and/or T4 cervical and thoracic vertebrae The second pair of electrodes 20a, 20b are applied to provide stimulation to the lower trapezius and serratus anterior muscles and nerves. The first electrode 20a of the second channel is positioned in electrical contact with tissue to simulate the serratus anterior muscle, and the second electrode 20b is positioned in electrical contact with tissue to simulate the lower trapezius muscle and the thoracic paraspinal muscles near the T3, T4, T5, T6, T7, T8, and/or T9 thoracic vertebrae of said patient, In this exemplary embodiment, the pulse train pattern comprises a triphasic overlapping pulse train pattern having the following parameters:
Pulse duration of individual electrical pulses: 50-70 microseconds
Current amplitude of individual electrical pulses: 30-70 milliamps
Duration of first phase: 100 milliseconds
Duration of overlap: 20 milliseconds
Duration of second phase: 100 milliseconds
Duration of overlap: 20 milliseconds
Duration of third phase: 60 milliseconds
Frequency of pulse train pattern: 0.67 hertz
Total treatment time: 20 minutes
Total number of treatments: 18 (over six weeks)
Frequency of individual electrical pulses (in each phase): 50 hertz In this exemplary embodiment, a continuous direct or pulsed direct current of approximately 1 mA with a current density of greater than 0.015 ma/cm² is simultaneously applied transcranially to the brain somatosensory and motor cortex region controlling the upper extremities 135b.

Sixteenth Exemplary Embodiment

Figure 3P:
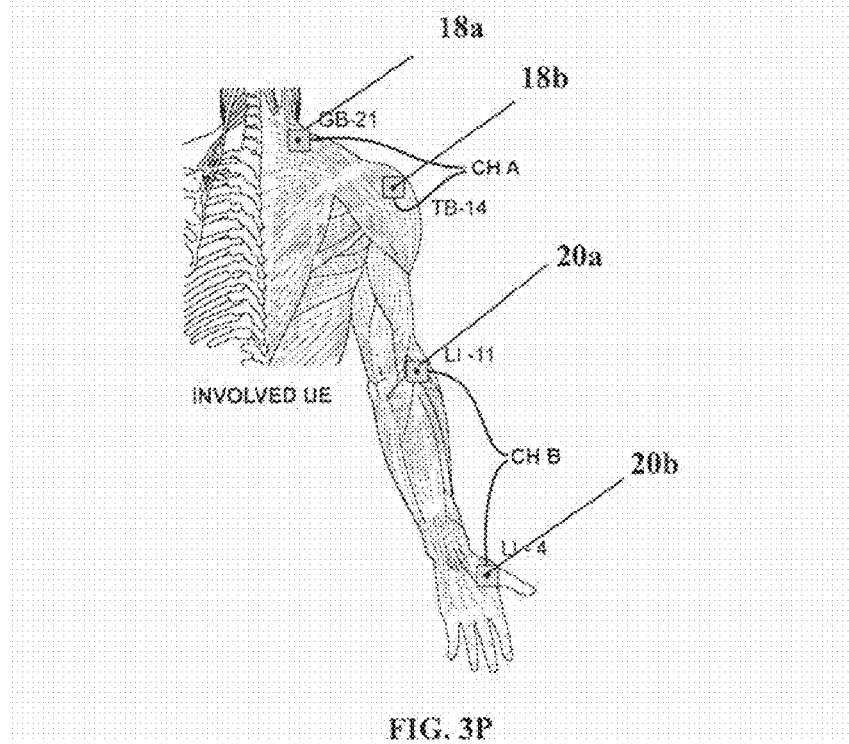
FIG. 3P illustrates a method for treating a neurological disorder in a patient by applying neuromuscular electrical stimulation in accordance with a sixteenth exemplary embodiment of the present invention, in which the muscles of the upper extremity are stimulated, such as the first dorsal interosseous or hand intrinsic muscles, the muscles in proximity to the elbow (such as the extensor carpi radialis longus and brevis at their origin near the elbow, including the radial nerve), the posterior shoulder muscles, and the cervical paraspinal muscles are stimulated. The neuromuscular electrical stimulation is combined with transcranial direct current electrical stimulation as generally illustrated in FIG. 4.

In a sixteenth exemplary embodiment of the present invention, as generally illustrated in FIG. 3P, two pairs pair of electrodes are positioned in electrical contact with the patient's tissue in order to provide electrical stimulation to one or more of the muscles involved in movements of the upper extremities.

More specifically, as shown in FIG. 3P, first pair of electrodes 18a, 18b are provided to provide simulation to the posterior portion of the arm. A first electrode 18a is positioned in electrical contact with tissue of the posterior lateral neck surface. Most preferably, first electrode 18a comprises a surface electrode that is positioned on the patient's skin posterior lateral neck surface in the region of C6, C7, and T1. A second electrode 18b is positioned is electrical contact with tissue to stimulate the patient's posterior deltoid muscle. Most preferably, second electrode 18b comprises a surface electrode that is positioned on the dorsal surface of the deltoid muscle, posterior and inferior to the acromion.

Another pair of electrodes 20a, 20b is provided to stimulate the posterior muscles of the arm. The first electrode 20a is positioned in electrical contact with tissue to stimulate a motor point of the patient's proximal extensor muscles of the forearm. Most preferably, first electrode 20a comprises a surface electrode that is positioned on the patient's skin on the dorsal/posterior side of the lower arm, over the extensor carpi radialis longus origin. A second electrode 20b is positioned is electrical contact with tissue to stimulate the patient's first dorsal interosseus muscle. Most preferably, second electrode 20b comprises a surface electrode that is positioned posteriorly on the patient's skin in the web-space between the thumb and first metacarpal bone.

During treatment, the first and second channels are positioned on the right or left arm, and a patterned pulse train is applied to the arm as discussed more fully below. It will be appreciated that the muscles involved in arm movement may be bilaterally stimulated when the electrical stimulation device contains at least four channels. Alternatively, two electrical stimulation devices can be used for bilateral stimulation: one to simulate the right upper extremity, and one to stimulate the left upper extremity.

In this exemplary embodiment, the pulse train pattern comprises a low frequency pulse train pattern or a frequency-sequenced pulse burst train pattern having the following parameters:
Low Frequency Pulse Train Pattern:
Pulse duration of individual electrical pulses: 200 microseconds
Current amplitude of individual electrical pulses: 10-50 milliamps
Total treatment time: 20 minutes
Total number of treatments: 1.8 (over six weeks)
Frequency of individual electrical pulses (in each phase): 50 hertz
Frequency Sequenced Pulse Burst Train Pattern
Carrier Frequency: 500 Hz-100,000 Hz
First Sequence Burst Frequency: 2-20 Hz for up to 10 minutes
Second Sequence Burst Frequency: 0.1 Hz-5 Hz for up to thirty minutes
Third Sequence Burst Frequency: 20 Hz-250 Hz for up to 20 minutes
Current amplitude of individual electrical pulses: 10-50 milliamps
Total treatment time: up to 60 minutes
Total number of treatments: 18 (over six weeks)

In this exemplary embodiment, a continuous direct or pulsed direct current of approximately 1 mA with a current density of greater than 0.015 mA/cm$^2$ is simultaneously applied transcranially to the brain somatosensory and motor cortex region controlling the upper extremities 135b.

Seventeenth Exemplary Embodiment

Figure 3Q:
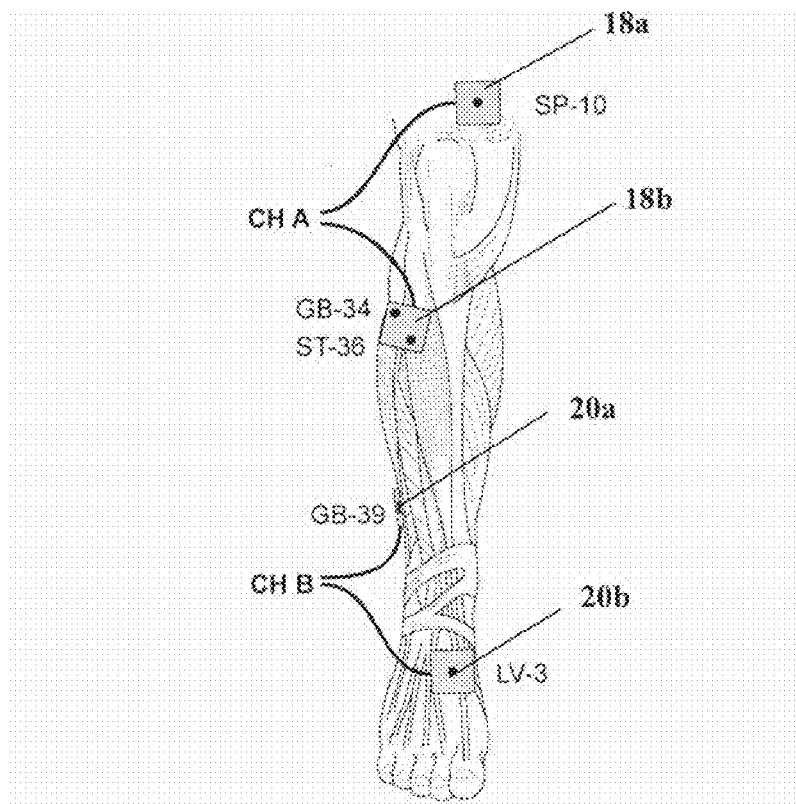
FIG. 3Q illustrates a method for treating a neurological disorder in a patient by applying neuromuscular electrical stimulation in accordance with a seventeenth exemplary embodiment of the present invention, in which the muscles of the lower extremity are stimulated, including but not limited to the muscles associated with the knee (e.g., vastus medialis muscle), leg (e.g., proximal anterior tibialis and distal peroneal muscles), and/or foot (e.g., extensor digitorum brevis muscle). The neuromuscular electrical stimulation is combined with transcranial direct current electrical stimulation as generally illustrated in FIG. 4.

In a seventeenth exemplary embodiment of the present invention, as generally illustrated in FIG. 3Q, two pairs pair of electrodes are positioned in electrical contact with the patient's tissue in order to provide electrical stimulation to one or more of the muscles involved in movements of the lower extremities.

More specifically, as shown in FIG. 3Q, first pair of electrodes 18a, 18b are provided to provide simulation to the anterior portion of the lower extremity. A first electrode 18a is positioned in electrical contact with tissue of the thigh above the patella. Most preferably, first electrode 18a comprises a surface electrode that is positioned on the patient's skin approximately 2 body inches proximal to the medial superior border of the patella over the quadricep muscles, such as the vastus medialis. A second electrode 18b is positioned is electrical contact with tissue to stimulate the patient's anterior tibialis. Most preferably, second electrode 18b comprises a surface electrode that is positioned anterior and inferior to the fibular head.

Another pair of electrodes 20a, 20b is provided to stimulate the lateral leg and dorsal foot muscles and nerves. The first electrode 20a is positioned in electrical contact with tissue to stimulate the distal peroneal muscles. Most preferably, first electrode 20a comprises a surface electrode that is positioned on the patient's skin on the a point three body inches above the lateral malleolus between the posterior border of the fibula over the peroneus tendons. A second electrode 20b is positioned is electrical contact with tissue to stimulate the extensor digitorum brevis muscle and deep peroneal nerve. Most preferably, second electrode 20b comprises a surface electrode that is positioned on the dorsum of the foot, over the first three metatarsal bones.

During treatment, the first and second channels are positioned on the right or left lower extremity and a patterned pulse train is applied to the arm as discussed more fully below. It will be appreciated that the muscles involved in arm movement may be bilaterally stimulated when the electrical stimulation device contains at least four channels. Alternatively, two electrical stimulation devices can be used for bilateral stimulation: one to simulate the right lower extremity, and one to stimulate the left lower extremity.

In this exemplary embodiment, the pulse train pattern comprises a low frequency pulse train pattern or a frequency-sequenced pulse burst train pattern having the following parameters:
Low Frequency Pulse Train Pattern:
Pulse duration of individual electrical pulses: 200 microseconds
Current amplitude of individual electrical pulses: 10-50 milliamps
Total treatment time: 20 minutes
Total number of treatments: 18 (over six weeks)
Frequency of individual electrical pulses (in each phase): 50 hertz
Frequency Sequenced Pulse Burst Train Pattern
Carrier Frequency: 500 Hz-100,000 Hz
First Sequence Burst Frequency: 2-20 Hz for up to 10 minutes
Second Sequence Burst Frequency: 0.1 Hz-5 Hz for up to thirty minutes
Third Sequence Burst Frequency: 20 Hz-250 Hz for up to 20 minutes
Current amplitude of individual electrical pulses: 10-50 milliamps
Total treatment time: up to 60 minutes
Total number of treatments: 1.8 (over six weeks)

In this exemplary embodiment, a continuous direct or pulsed direct current of approximately 1 mA with a current density of greater than 0.015 mA/cm$^2$ is simultaneously applied transcranially to the brain somatosensory and motor cortex region controlling the lower extremities 135c.

Eighteenth Exemplary Embodiment

Figure 3R:
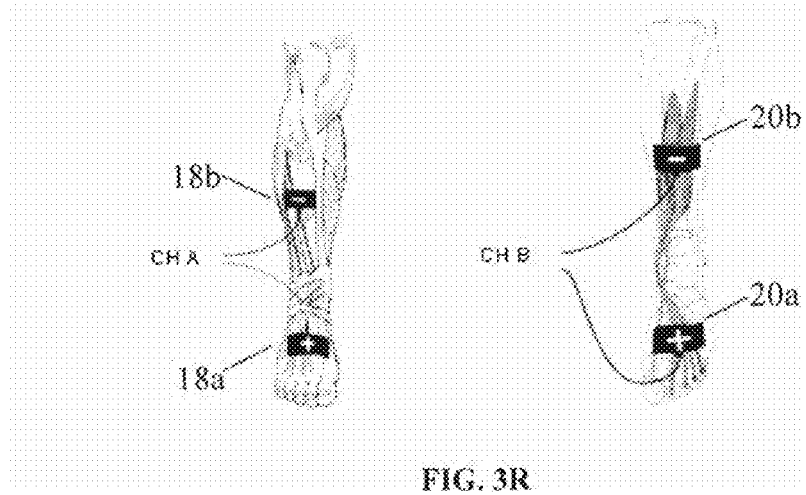
FIG. 3R illustrates a method for treating a neurological disorder in a patient by applying neuromuscular electrical stimulation in accordance with an eighteenth exemplary embodiment of the present invention, in which the muscles associated with toe extension/flexion as well as inversion/eversion are stimulated. The neuromuscular electrical stimulation is combined with transcranial direct current electrical stimulation as generally illustrated in FIG. 4.

In a eighteenth exemplary embodiment of the present invention, as generally illustrated in FIG. 3R, a pair of electrodes is positioned in electrical contact with the patient's tissue in order to provide electrical stimulation to one or more of the muscles associated with toe and ankle dorsiflexion (or extension) and flexion (or plantar flexion) as a treatment for neurological disorders afflicting the lower extremities. In addition, at least one of a pair of electrodes is positioned in electrical contact of the area of the cranium overlying the brain somatosensory and motor control of the lower extremity 135c as illustrated in FIG. 4A.

More specifically, as generally shown in FIG. 3R, a two-channel system is used to apply electrical stimulation to agonist/antagonist muscles involved in toe and ankle extension/flexion. In the first channel, a first electrode 18a is positioned is electrical contact with tissue to stimulate the motor point of the extensor digitorum brevis muscle (which extends the joints of the proximal phalanges of toes 1-4). Most preferably, second electrode 18b comprises a surface electrode that is positioned on the patient's skin at the anterior lateral mid shaft of the leg over the mid tibialis anterior and the approximate mid belly of the extensor digitorum longus and extensor hallicus longus. Most preferably, first electrode 18a comprises a surface electrode that is positioned on the patient's skin about mid-leg.

For the second channel, a first electrode 20*a* is positioned is electrical contact with tissue to stimulate the intrinsic muscles of the foot. Most preferably, first electrode 20*a* comprises a surface electrode that is positioned on the patient's skin on the sole of the foot at the anterior one-third junction to include the abductor hallucis. The second electrode 20*b* is positioned in electrical contact with tissue to stimulate the posterior tibialis and flexor hallicus muscles.

During treatment, the first and second channels are positioned on the right or left leg, and a patterned pulse train is applied to the leg as discussed more fully below. It will be appreciated that the muscles involved in toe extension and flexion may be bilaterally stimulated when the electrical stimulation device contains at least four channels. Alternatively, two electrical stimulation devices can be used for bilateral stimulation: one to simulate the right leg, and one to stimulate the left leg.

In this exemplary embodiment, the pulse train pattern comprises a triphasic overlapping pulse train pattern having the following parameters:
Pulse duration of individual electrical pulses: 50-70 microseconds
Current amplitude of individual electrical pulses: 30-70 milliamps
Duration of first phase: 200 milliseconds
Duration of overlap between first and second phase: 40 milliseconds
Duration of second phase: 200 milliseconds
Duration of overlap between second and third phase: 40 milliseconds
Duration of third phase: 120 milliseconds
Frequency of pulse train pattern: 0.67 hertz
Total treatment time: 20 minutes
Total number of treatments: 18 during six weeks
Frequency of individual electrical pulses (in each phase): 50 Hz In this exemplary embodiment, a continuous direct or pulsed direct current of approximately 1 mA with a current density of greater than 0.015 ma/cm$^2$ is simultaneously applied transcranially to the brain somatosensory and motor cortex region controlling the lower extremities 135*c*. If the bilateral lower extremities are involved, the transcranial stimulation could be applied bilaterally with the positive electrode placed as described in 135*c* on each side of the cranium and the negative electrodes placed either on the forehead utilizing larger electrodes or on a neutral position over the upper shoulder.

Nineteenth Exemplary Embodiment

Figure 3S:
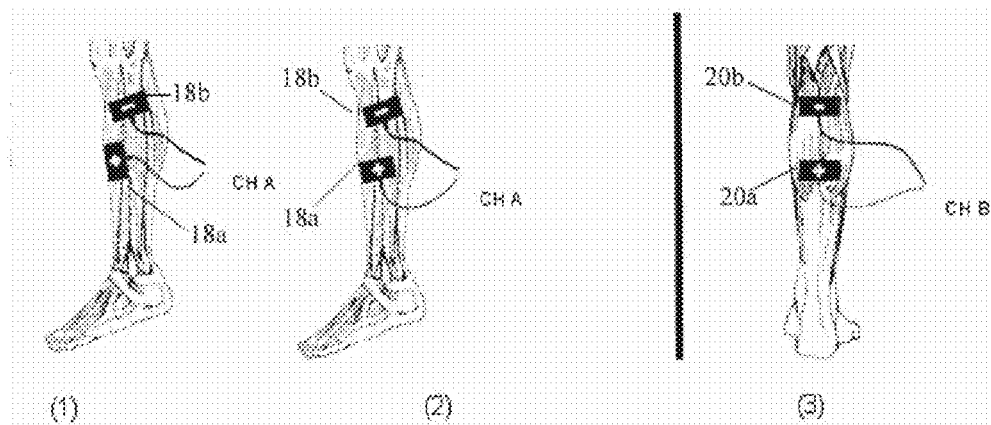
FIG. 3S illustrates a method for treating a neurological disorder in a patient by applying neuromuscular electrical stimulation in accordance with a nineteenth exemplary embodiment of the present invention, in which the muscles associated with ankle dorsiflexion/eversion and plantar flexion/eversion are stimulated. The neuromuscular electrical stimulation is combined with transcranial direct current electrical stimulation as generally illustrated in FIG. 4.

In a nineteenth exemplary embodiment of the present invention, generally illustrated in FIG. 3S, a pair of electrodes is positioned in electrical contact with the patient's tissue in order to provide electrical stimulation to one or more of the muscles associated with ankle dorsiflexion and eversion and plantar flexion as a treatment for neurological disorders that afflict the lower extremities. In addition, at least one of a pair of electrodes is positioned in electrical contact of the area of the cranium overlying the brain somatosensory and motor control of the lower extremity 135*c* as illustrated in FIG. 4A

More specifically, as shown in FIG. 3S, a two-channel system is used to apply electrical stimulation to muscles involved in ankle dorsiflexion and plantar flexion and/or ankle inversion and eversion. In the first channel (panel 1 of FIG. 3S), a first electrode 18*a* is positioned is electrical contact with tissue to stimulate the lower portion of the tibialis anterior muscle. Most preferably, first electrode 18*a* comprises a surface electrode that is positioned on the patient's skin over the mid belly of the anterior tibialis. A second electrode 18*b* is positioned in electrical contact with tissue to stimulate the patient's proximal tibialis anterior muscle. Most preferably, second electrode 18*b* comprises a surface electrode that is positioned on the patient's skin inferior to the fibular head.

Alternatively, in the first channel (panel 2 of FIG. 3S), a first electrode 18*a* is positioned is electrical contact with tissue to stimulate the anterior and lateral muscles of the leg. Most preferably, first electrode 18*a* comprises a surface electrode that is positioned on the patient's skin mid belly of the anterior tibialis as well as the peroneus muscles. A second electrode 18*b* is positioned in electrical contact with tissue to stimulate the patient's proximal tibialis anterior muscle. Most preferably, second electrode 18*b* comprises a surface electrode that is positioned on the patient's skin inferior to the fibular head.

For the second channel (panel 3 of FIG. 3S), a first electrode 20*a* and second electrode 20*b* are positioned in electrical contact with tissue to stimulate the patient's triceps surae Most preferably, first electrode 20*a* comprises a surface electrode that is positioned on the patient's skin directly over the junction of the gastrocnemius and the soleus muscles. Most preferably, second electrode 20*b* comprises a surface electrode that is positioned on the patient's skin posteriorly just inferior to the popliteal fossa over the tibial nerve and the two heads of the gastrocnemius muscle.

During treatment, the first and second channels are positioned on the right or left lee, and a patterned pulse train is applied to the leg as discussed more fully below. It will be appreciated that the muscles involved in toe extension and flexion may be bilaterally stimulated when the electrical stimulation device contains at least four channels. Alternatively, two electrical stimulation devices can be used for bilateral stimulation: one to simulate the right leg, and one to stimulate the left leg.

In this exemplary embodiment, the pulse train pattern comprises a triphasic overlapping pulse train pattern or a functional pattern that typically creates ankle dorsiflexion and eversion having the following parameters:
Triphasic Overlapping Pulse Train Pattern
Pulse duration of individual electrical pulses: 50-70 microseconds
Current amplitude of individual electrical pulses: 30-70 milliamps
Duration of first phase: 200 milliseconds
Duration of overlap between first and second phase: 40 milliseconds
Duration of second phase: 200 milliseconds
Duration of overlap between second and third phase: 40 milliseconds
Duration of third phase: 120 milliseconds
Frequency of pulse train pattern: 0.67 hertz
Total treatment time: 20 minutes
Total number of treatments: 18 during six weeks
Frequency of individual electrical pulses (in each phase): 50 Hz
Functional Pattern for Ankle Dorsiflexion and Eversion
Pulse duration of individual electrical pulses: 50-200 microseconds
Current amplitude of individual electrical pulses: 30-140 milliamps
Duration of first phase: 400 milliseconds
Duration of overlap: 250 milliseconds
Duration of second phase: 250 milliseconds
Frequency of pulse train pattern: 1.0 hertz Total treatment time: up to 30 minutes
Total number of treatments: 18 (over six weeks)
Frequency of individual electrical pulses (in each phase): 50 hertz In this exemplary embodiment, a continuous direct or pulsed direct current of approximately 1 mA with a current density of greater than 0.0.15 mA/cm$^2$ is simultaneously applied transcranially to the brain somatosensory and motor cortex region controlling the lower extremities 135c.

Twentieth Exemplary Embodiment

Figure 3T:
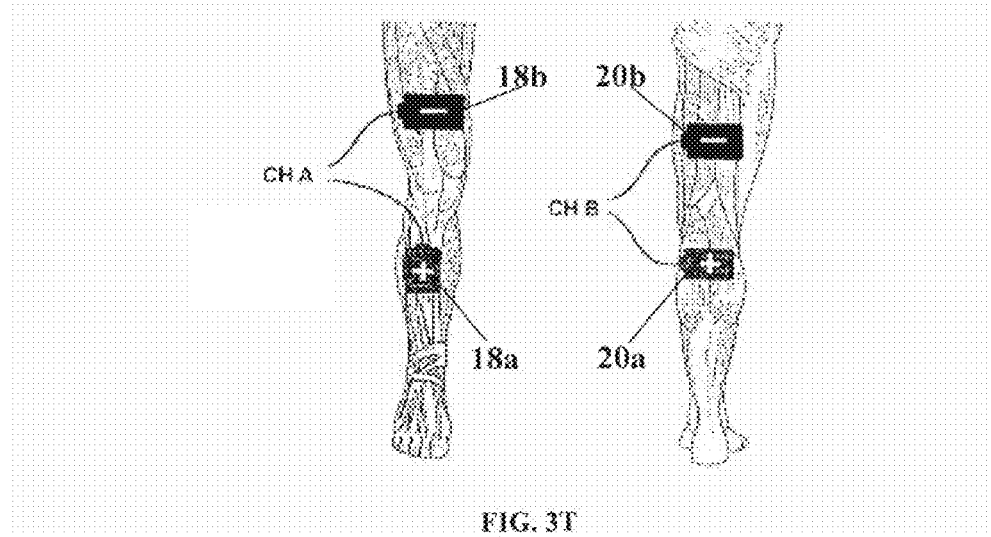
FIG. 3T illustrates a method for treating a neurological disorder in a patient by applying neuromuscular electrical stimulation in accordance with a twentieth exemplary embodiment of the present invention, in which the muscles associated with movement of the lower extremities are stimulated. The neuromuscular electrical stimulation is combined with transcranial direct current electrical stimulation as generally illustrated in FIG. 4.

In an twentieth exemplary embodiment of the present invention, generally illustrated in FIG. 3T, a pair of electrodes is positioned in electrical contact with the patient's tissue in order to provide electrical stimulation to one or more of the muscles associated with the lower extremities as a treatment for neurological disorders that afflict the lower extremities. In addition, at least one of a pair of electrodes is positioned in electrical contact of the area of the cranium overlying the brain somatosensory and motor control of the lower extremity 135c as illustrated in FIG. 4A.

More specifically, as generally shown in FIG. 3T, a two-channel system is used to apply electrical stimulation to muscles involved in movement of the lower extremity. In the first channel, a first electrode 18a is positioned in electrical contact with tissue to stimulate the patient's proximal tibialis anterior muscle. Most preferably, second electrode 18b comprises a surface electrode that is positioned on the patient's skin inferior to the fibular head. A second electrode 18b is positioned in electrical contact with tissue to stimulate the midpoint of the quadriceps muscles. In the second channel, a first electrode 20a is positioned is electrical contact with tissue to stimulate the patient's triceps surae. A second electrode 20b is positioned in electrical contact with tissue to stimulate the mid hamstrings.

During treatment, the first and second channels are positioned on the right or left leg, and a patterned pulse train is applied to the leg as discussed more fully below. It will be appreciated that the muscles involved in toe extension and flexion may be bilaterally stimulated when the electrical stimulation device contains at least four channels. Alternatively, two electrical stimulation devices can be used for bilateral stimulation: one to simulate the right leg, and one to stimulate the left leg.

In this exemplary embodiment, the pulse train pattern comprises a triphasic overlapping pulse train pattern having the following parameters:
Pulse duration of individual electrical pulses: 50-100 microseconds
Current amplitude of individual electrical pulses: 30-90 milliamps
Duration of first phase: 200 milliseconds
Duration of overlap between first and second phase: 40 milliseconds
Duration of second phase: 200 milliseconds
Duration of overlap between second and third phase: 40 milliseconds
Duration of third phase: 120 milliseconds.
Frequency of pulse train pattern: 0.67 hertz
Total treatment time: 20 minutes
Total number of treatments: 18 during six weeks
Frequency of individual electrical pulses (in each phase): 50 Hz In this exemplary embodiment, a continuous direct or pulsed direct current of approximately 1 mA with a current density of greater than 0.015 ma/cm$^2$ is simultaneously applied transcranially to the brain somatosensory and motor cortex region controlling the lower extremities 135c.

Twenty-First Exemplary Embodiment

Figure 3U:
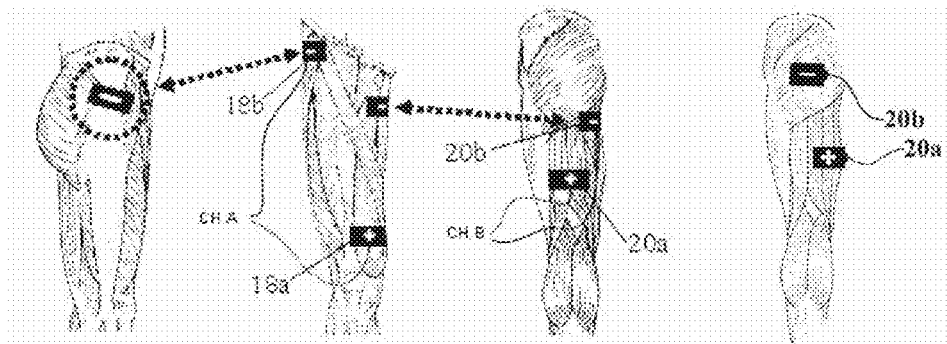
FIG. 3U illustrates a method for treating a neurological disorder in a patient by applying neuromuscular electrical stimulation in accordance with a twenty-first exemplary embodiment of the present invention, in which the muscles associated with hip abduction/adduction/extension and knee extension/flexion are stimulated. The neuromuscular electrical stimulation is combined with transcranial direct current electrical stimulation as generally illustrated in FIG. 4.

In a twenty-first exemplary embodiment of the present invention, generally illustrated in FIG. 3U, a pair of electrodes is positioned in electrical contact with the patient's tissue in order to provide electrical stimulation to one or more of the muscles associated with hip abduction and knee extension as well as hip adduction and knee flexion (stabilization) as a treatment for neurological disorders that afflict the lower extremities. In addition, at least one of a pair of electrodes is positioned in electrical contact of the area of the cranium overlying the brain somatosensory and motor control of the lower extremity 135c as illustrated in FIG. 4A.

More specifically, as generally shown in FIG. 3U, a two-channel system is used to apply electrical stimulation to muscles involved in hip abduction/adduction and knee extension/flexion. In the first channel, a first electrode 18a is positioned is electrical contact with the quadricep muscles, and in particular to stimulate the motor point of the vastus medialis, which functions as an extensor of the knee. A second electrode 18b is positioned in electrical contact with tissue to stimulate the gluteus medius, gluteus minimus, and tensor faciae latae. Preferably, the second electrode 18b is positioned about midway between the iliac crest and the greater trochanter. In the second channel, a first electrode 20a is positioned is electrical contact with tissue to stimulate the patient's hamstring muscles (biceps femoris, semitendinosus, and/or semimembraneous muscles) A second electrode 20b is positioned in electrical contact with tissue to stimulate the adductor magnus, adductor longus, adductor brevis, and medial hamstring muscles.

The far right panel of FIG. 3U shows the hip extensor alternative placement: In the second channel, a first electrode 20a is positioned in electrical contact with tissue to stimulate the adductor magnus, adductor longus, adductor brevis and medial hamstring muscles. A second electrode 20b is positioned in electrical contact with tissue to stimulate the mid-belly of the gluteus maximus.

During treatment, the first and second channels are positioned on the right or left leg, and a patterned pulse train is applied to the leg as discussed more fully below. It will be appreciated that the muscles involved in hip abduction/adduction and knee extension/flexion may be bilaterally stimulated when the electrical stimulation device contains at least four channels. Alternatively, two electrical stimulation devices can be used for bilateral stimulation: one to simulate the right leg, and one to stimulate the left leg.

In this exemplary embodiment, the pulse train pattern comprises a triphasic overlapping pulse train pattern having the following parameters:
Pulse duration of individual electrical pulses: 50-200 microseconds
Current amplitude of individual electrical pulses: 30-140 milliamps
Duration of first phase: 200 milliseconds
Duration of overlap between first and second phase: 40 milliseconds
Duration of second phase: 200 milliseconds
Duration of overlap between second and third phase: 40 milliseconds
Duration of third phase: 120 milliseconds
Frequency of pulse train pattern: 0.67 hertz
Total treatment time: 20 minutes
Total number of treatments: 18 during six weeks Frequency of individual electrical pulses (in each phase): 50 Hz In this exemplary embodiment, a continuous direct or pulsed direct current of approximately 1 mA with a current density of greater than 0.015 ma/cm$^2$ is simultaneously applied transcranially to the brain somatosensory and motor cortex region controlling the lower extremities 135c. For bilateral neuromuscular stimulation, the pattern would be biphasic and sequenced from one extremity to the other. If the bilateral lower extremities are involved, the transcranial stimulation could be applied bilaterally with the positive electrode placed as described in 135c on each side of the cranium and the negative electrodes placed either on the forehead utilizing larger electrodes or on a neutral position over the upper trapezius.

Twentieth-Second Exemplary Embodiment

Figure 3V:
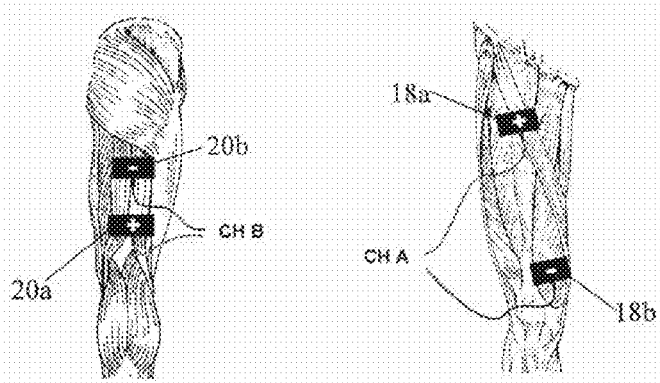
FIG. 3V illustrates a method for treating a neurological disorder in a patient by applying neuromuscular electrical stimulation in accordance with a twenty-second exemplary embodiment of the present invention, in which the muscles associated with knee flexion and extension are stimulated. The neuromuscular electrical stimulation is combined with transcranial direct current electrical stimulation as generally illustrated in FIG. 4.

In a twenty-second exemplary embodiment of the present invention, generally illustrated in FIG. 3V, a pair of electrodes is positioned in electrical contact with the patient's tissue in order to provide electrical stimulation to one or more of the muscles associated with knee extension and flexion as a treatment for neurological disorders that afflict the lower extremities. In addition, at least one of a pair of electrodes is positioned in electrical contact of the area of the cranium overlying the brain somatosensory and motor control of the lower extremity 135c as illustrated in FIG. 4A More specifically, as generally shown in FIG. 3V, a two-channel system is used to apply electrical stimulation to muscles involved in knee extension/flexion. In the first channel, a first electrode 18a is positioned in electrical contact with tissue to stimulate the rectus lemons and vastus lateralis muscles. A second electrode 18b is positioned is electrical contact with the vastus medialis muscles, and in particular to stimulate a motor point of the on the vastus medialis, which functions as an extensor of the knee. In the second channel, the electrode 20a is positioned in electrical contact with tissue to stimulate the distal portion of the patient's biceps femoris, semimembranosus, and/or semitendinosus muscles. Electrode 20b is positioned in electrical contact with tissue to stimulate the proximal portion of the patient's biceps femoris, semimembranosus, and/or semitendinosus muscles.

During treatment, the first and second channels are positioned on the right or left leg, and a patterned pulse train is applied to the leg as discussed more fully below. It will be appreciated that the muscles involved in hip knee extension/flexion may be bilaterally stimulated when the electrical stimulation device contains at least four channels. Alternatively, two electrical stimulation devices can be used for bilateral stimulation: one to simulate the right leg, and one to stimulate the left leg.

In this exemplary embodiment, the pulse train pattern comprises a triphasic overlapping pulse train pattern having the following parameters:
Pulse duration of individual electrical pulses: 50-200 microseconds
Current amplitude of individual electrical pulses: 30-140 milliamps
Duration of first phase: 200 milliseconds
Duration of overlap between first and second phase: 40 milliseconds
Duration of second phase: 200 milliseconds
Duration of overlap between second and third phase: 40 milliseconds
Duration of third phase: 120 milliseconds
Frequency of pulse train pattern: 0.67 hertz
Total treatment time: 20 minutes
Total number of treatments: 18 during six weeks
Frequency of individual electrical pulses (in each phase): 50 Hz In this exemplary embodiment, a continuous direct or pulsed direct current of approximately 1 mA with a current density of greater than 0.015 ma/cm$^2$ is simultaneously applied transcranially to the brain somatosensory and motor cortex region controlling the lower extremities 135e.

Figure 3W:
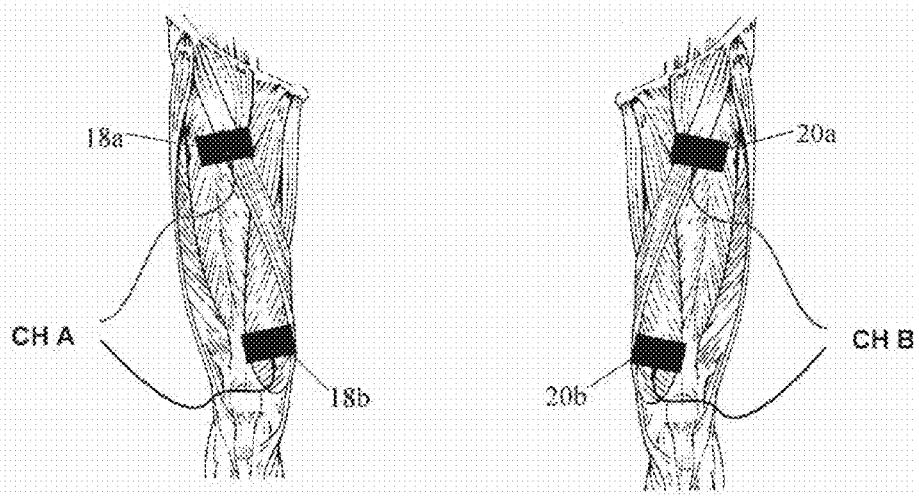
FIG. 3W illustrates a method for treating a neurological disorder in a patient by applying neuromuscular electrical stimulation in accordance with a twenty-third exemplary embodiment of the present invention, in which the muscles associated with bilateral knee extension are stimulated. The neuromuscular electrical stimulation is combined with transcranial direct current electrical stimulation as generally illustrated in FIG. 4.

Twenty-Third Exemplary Embodiment in a twenty-third exemplary embodiment of the present invention, generally illustrated in FIG. 3W, a pair of electrodes is positioned in electrical contact with the patient's tissue in order to provide electrical stimulation to one or more of the muscles associated with functional rehabilitation of walking, cycling, and sit-to-stand are used as a treatment for neurological disorders that afflict the lower extremities. In addition, at least one of a pair of electrodes is positioned in electrical contact of the area of the cranium overlying the brain somatosensory and motor control of the lower extremity. In addition, at least one of a pair of electrodes is positioned in electrical contact of the area of the cranium overlying the brain somatosensory and motor control of the lower extremity 135c as illustrated in FIG. 4A. Alternatively, two pairs of electrodes may be used as illustrated in FIG. 4E (either panel) with the negative electrode of the first channel being placed over 135c on FIG. 4A.

More specifically, as generally shown in FIG. 3W, a two-channel system is used to apply electrical stimulation to muscles involved in knee extension. In the first channel, a first electrode 18a is positioned in electrical contact with tissue to stimulate the rectus femoris, and vastus lateralis muscles. A second electrode 18b is positioned is electrical contact with the vastus medialis muscles, and in particular to stimulate a motor point of the on the vastus medians, which functions as an extensor of the knee. In the second channel, the electrode 20a is positioned in electrical contact with tissue to stimulate the contralateral knee extensors on the opposite side of the body.

In this exemplary embodiment, the pulse train pattern comprises a functional pulse train patterns having the following parameters:
Pulse Train Pattern for Walking:
Pulse duration of individual electrical pulses: 50-100 microseconds
Current amplitude of individual electrical pulses: 50-140 milliamps
Duration of first phase: 240 milliseconds
Duration of delay: 260 milliseconds
Duration of second phase: 240 milliseconds
Frequency of pulse train pattern: 1.0 hertz
Frequency of individual electrical pulses (in each phase): 50 hertz
Total treatment time: 10 minutes
Total number of treatments: 18 (over six weeks)
The timing parameters to be adjusted for the desired speed or cycles per minute. The current embodiment demonstrates timing pattern for lower extremity walking at 1 Hz.
Pulse Train Pattern for Cycling:
Pulse duration of individual electrical pulses: 50-200 microseconds
Current amplitude of individual electrical pulses: 50-140 milliamps
Duration of first phase: 340 milliseconds
Duration of delay: 160 milliseconds Duration of second phase: 340 milliseconds
Frequency of pulse train pattern: 1.0 hertz
Total treatment time: 10 minutes
Total number of treatments: 18 (over six weeks)
Frequency of individual electrical pulses (in each phase): 50 hertz The timing parameters to be adjusted for the desired speed or cycles per minute. The current embodiment demonstrates timing pattern for lower extremity cycling at 1 Hz.
Pulse Train Pattern for Sit-to-Stand:
Pulse duration of individual electrical pulses: 50-200 microseconds
Current amplitude of individual electrical pulses: 50-140 milliamps
Duration of first phase ramp: 2 seconds
Duration of first phase: 3 seconds
Frequency of pulse train pattern: 0.1 hertz
Total treatment time: 15 minutes
Total number of treatments: 18 (over six weeks)
Frequency of individual electrical pulses (in each phase): 50 hertz The timing parameters to be adjusted for the desired speed or cycles per minute. The current embodiment demonstrates timing pattern for sit-to-stand every 10 seconds. When using sit to stand training, both channels are stimulated simultaneously.

In these exemplary embodiments, a continuous direct or pulsed direct current of approximately 1 mA with a current density of greater than 0.015 ma/cm$^2$ is simultaneously applied transcranially to the brain somatosensory and motor cortex region controlling the lower extremities 135c as illustrated in FIG. 4A. An alternative placement for brain stimulation is illustrated in FIG. 4E (either panel) using a 2 channel stimulator placed in a quadripolar arrangement with the electrode 118a being the positive electrode applied to the brain somatosensory and motor cortex region controlling the lower extremities 135c as illustrated in FIG. 4A.

It will also be appreciated that the neurological disorder treatment methods of the present invention may readily be adapted by configuring the electrodes in a manner that is asymmetrical or bilateral in nature. For example, a combination of the Fifth and Seventh exemplary embodiments may be used. It is contemplated that all of the Exemplary embodiments may be combined in a similar manner to fit the patient's needs and symptoms (e.g. first embodiment for the first channel and either the second, third, fourth, fifth, sixth, or seventh embodiments for the second channel, and so on).

Case Study #1
This case study involved a 67 year-old female four months following a stroke affecting the left side of her body. She was unable to move her left hand at all voluntarily and required considerable effort by the therapy staff to move her fingers passively. After stretching, her hand moved rapidly back into full flexion of the fingers and thumb. The thumb had developed a flexion contracture. She had no voluntary supination and maintained the wrist at about 45 degrees of pronation. She had undergone three weeks of daily in-patient therapy beginning one week after the stroke and twice weekly outpatient therapy which involved stretching and facilitation techniques without success for the three months before this treatment program.

The patient was first treated with a transcranial constant direct current stimulator with the positive electrode (30 cm$^2$) was positioned to the right scalp overlying the brain somatosensory and motor region for the hand and upper extremity. The negative electrode (22 cm$^2$) was positioned over the left shoulder muscle as a neutral location. After applying transcranial direct current stimulation for ten minutes at 1.0 mA of constant direct current, the peripheral stimulation program began as described below.

During the patient experienced a very slight tingling sensation under both the positive and negative electrodes of the transcranial stimulator. No adverse effects were noted. The total treatment time for the transcranial stimulation was about 30 minutes.

After about 10 minutes, the patient was treated with Omnistim® FX$^2$ electrical stimulation with a therapy protocol described as the "upper extremity tri-phasic" with channel A negative (2"×4") electrode applied to the forearm flexors and the positive (2"×4") electrode applied to the hand intrinsics. Channel B applied to the forearm wrist and finger extensors with the negative (2"×4") electrode applied to the proximal forearm muscles and the positive (2"×4") electrode applied to the distal forearm muscles. Electrode placements and protocol follow description is the twelfth exemplary embodiment.

The intensity of the peripheral stimulation was increased to create minimal twitch muscle contractions with visible activation and minimal linger and wrist movement. The pulse train timing pattern comprises a triphasic overlapping pulse train pattern having the following parameters:
Phases one and three are applied through channel A
Phase two is applied through channel B
Pulse duration of individual electrical pulses: 50 microseconds
Current amplitude of individual electrical pulses: 60-90 milliamps
Duration of first phase: 100 milliseconds (5 pulses per train)
Duration of overlap: 20 milliseconds (1 pulse)
Duration of second phase: 100 milliseconds (5 pukes per train)
Duration of third phase: 60 milliseconds (5 pulses per train)
Duration of overlap of third phase over second phase: 20 milliseconds (1 pulse)
Frequency of pulse train pattern: 1.5 seconds (0.67 Hz)
Total treatment time: 20 minutes for the peripheral stimulation
Frequency of individual electrical pulses (in each phase): 50 hertz Following the combination of the transcranial direct current stimulation and the peripheral patterned stimulation, the patient stated that her hand felt somewhat more "normal," especially in the ulnar distribution. She was able to move her thumb through a partial flexion and extension range of motion of 45 degrees with voluntary effort but extension was inhibited by muscle contracture. All four fingers demonstrated immediate functional improvement with voluntary movement from initial position of full flexion to extension lacking only the last 20 degrees of metacarpal-phalangeal (MP) joint motion and 10 degrees of proximal inter phalangeal (PIP) joint motion. This motion was able to be repeated voluntarily and was maintained with only partial loss of range of motion.

At follow-up in 12 weeks she was still able to extend the fingers but declined to minus 45 degrees of MP extension but improved PIP extension to full range. A single repeat combination stimulation again improved her voluntary finger extension to minus 20 degrees MP motion. The maneuver was considerably faster taking only 1-2 seconds following this procedure. After the first procedure the finger extension through the same range took 4 seconds. She was also able to supinate the forearm to neutral.

Case Study #2
The second case study involves an 81 year-old male who suffered a stroke 34 years ago and who had not regained any voluntary movement of his left hand. He had sustained a right middle cerebral artery infarct at the time. Despite therapies, he had no voluntary return of movement to the wrist and hand. He had some shoulder and elbow motion. He was able to stretch the fingers and thumb using his right hand. He was not able to generate even a minimal voluntary twitch of any digit of the hand.

The patient was first treated with a transcranial constant direct current stimulator with the positive electrode (30 cm$^2$) was positioned to the right scalp overlying the brain motor region for the hand and upper extremity. The negative electrode (22 cm$^2$) was positioned over the left shoulder muscle as a neutral location. After applying transcranial direct current stimulation for ten minutes at 1.0 mA of constant direct current, the peripheral stimulation program began as described below.

During the treatment, patient experienced a very slight tingling sensation under both the positive and negative electrodes of the transcranial stimulator. No adverse effects were noted. The total treatment time for the transcranial stimulation was about 30 minutes.

After about 10 minutes, the patient was treated with Omnistim® FX$^2$ electrical stimulation with a therapy protocol described as the "upper extremity tri-phasic" with channel A negative (2"×4") electrode applied to the forearm flexors and the positive (2"×4") electrode applied to the hand intrinsics. Channel B applied to the forearm wrist and finger extensors with the negative (2"×4") electrode applied to the proximal forearm muscles and the positive (2"×4") electrode applied to the distal forearm muscles. Electrode placements and protocol follow description is the twelfth exemplary embodiment.

The intensity of the peripheral stimulation was increased to create minimal twitch muscle contractions with visible activation and minimal finger and wrist movement. The pulse train timing pattern comprises a triphasic overlapping pulse train pattern having the following parameters:
Phases one and three are applied through channel A
Phase two is applied through channel B
Pulse duration of individual electrical pulses: 50 microseconds
Current amplitude of individual electrical pulses: 60-90 milliamps
Duration of first phase: 100 milliseconds (5 pulses per train)
Duration of overlap: 20 milliseconds (1 pulse)
Duration of second phase: 100 milliseconds (5 pulses per train)
Duration of third phase: 60 milliseconds (5 pulses per train)
Duration of overlap of third phase over second phase: 20 milliseconds (1 pulse)
Frequency of pulse train pattern: 1.5 seconds (0.67 Hz)
Total treatment time: 20 minutes for the peripheral stimulation
Frequency of individual electrical pulses (in each phase): 50 hertz Following 20 minutes of neuromuscular stimulation combined with 30 minutes of the transcortical direct current stimulation with the positive placed over the right brain motor cortex approximating the hand region and the negative placed over the left side of the patient's upper shoulder, he was able to produce only most minimal but definite voluntary minimal twitch of the thumb but not any of the other fingers and the thumb movement lasted only about 15 minutes after the first stimulation program was completed.

Following a second session of the same combined stimulation protocol five days later, the patient was now able to produce voluntary movement of the thumb through a 45 degree range of motion and the fingers beginning at full flexion through 60 degrees of extension with equal motion at MP joints and the PIP joint. That was the first time he was able to move his fingers in the last 34 years.

This improvement lasted greater than 12 weeks with continued voluntary exercise. He also noted an improvement in the sensation of his hand.

Case Study #3

The third case example involves a 69 year-old male who sustained a left sided cerebrovascular accident resulting in right hemiparesis about nine months prior to the combined stimulation treatment. He had regained speech and swallowing but continues to have difficulty with ambulation and arm movement despite extensive rehabilitation therapies three times per week for the full nine months. He even had multiple sessions of the below noted FX2 electrical stimulation therapy without improvement.

The patient was first treated with a transcranial constant direct current stimulator with the positive electrode (30 cm$^2$) was positioned to the right scalp overlying the brain motor region for the left lower extremity. The negative electrode (22 cm$^2$) was positioned over the left upper trapezius muscle as a neutral location. After applying transcranial direct current stimulation for ten minutes at 1.0 mA of constant direct current, the peripheral stimulation program began as described below.

The patient was treated with OMNISTIM® FX2 electrical stimulation with a therapy protocol described as the "lower extremity tri-phasic" with channel. A negative (3"×5") electrode applied to the anterior lateral hip musculature and the positive (3"×5") electrode applied to the vastus medialis just medial and superior to the knee. Channel B applied to posterior hip and thigh with the negative (3"×5") electrode applied to the gluteus maximus muscle and the positive (3"×5") electrode applied to the medial aspect of mid hamstring muscles and hip adductors as described in the twenty-first exemplary embodiment with FIG. 3U (panel 2).

The intensity of the peripheral stimulation was such to create moderate muscle contractions that were well tolerated.

The pulse train timing pattern comprises a triphasic overlapping pulse train pattern having the following parameters:
Phases one and three are applied through channel A
Phase two is applied through channel B
Pulse duration of individual electrical pulses: 70 microseconds
Current amplitude of individual electrical pulses: 60-100 milliamps
Duration of first phase: 200 milliseconds
Duration of overlap: 40 milliseconds
Duration of second phase: 200 milliseconds
Duration of third phase: 120 milliseconds
Duration of overlap of third phase over second phase: 40 milliseconds
Frequency of pulse train pattern: 1.5 seconds (0.67 Hz)
Total treatment time: 20 minutes for the peripheral stimulation
Frequency of individual electrical pulses (in each phase): 50 hertz Phases one and three are applied through channel A After the first two sessions of transcranial direct current stimulation applied to the scalp overlying the left vertex corresponding to the motor strip region of the brain and EMG patterned electrical stimulation to the thigh and leg muscles—quadriceps, hamstrings, and gastroc—the patient showed no significant improvement in gait. As discussed above, the positive electrode location was initially over the lower extremity motor cortex at the left vertex but after the first two unsuccessful treatments, it was shifted laterally one cm posterior-laterally in an attempt to decrease the stimulation to the contralateral motor cortex.

The third session was a modification of the first two in which the transcranial application was moved one centimeter laterally away from the vertex and the peripheral stimulation was applied to the hip and thigh musculature as demonstrated in the twenty-first exemplary embodiment. Following 30 minutes of transcranial DC stimulation at 1 mA with 20 minutes of peripheral stimulation, the patient was able to again, transfer without assistance but his gait speed improved considerably. Before the third stimulation session, his shuttle walking took 29 seconds and repeated at 29 seconds tested 2 days prior and again just before the stimulation. Following the stimulation he was timed at 22 seconds and repeated at 22 seconds. Hip flexion and knee flexion improved to 30 degrees and he subjectively felt better balance.

Five days later, his gait had slowed to 25 seconds. After a fourth stimulation session using the same modified system of the third session, his shuttle time improved to 20 seconds average (21 and 19 seconds). He again noted a subjective improvement in balance. Normal fast gait for the same shuttle tested out to be 10 seconds. The improvement in gait and balance continued after 5 more days.

While the present invention has been described and illustrated hereinabove with reference to several exemplary embodiments, it should be understood that various modifications could be made to these embodiments without departing from the scope of the invention. Therefore, the invention is not to be limited to the exemplary embodiments described and illustrated hereinabove, except insofar as such limitations are included in the following claims.

What is claimed and desired to be secured by Letters Patent is as follows:

1. An electrical stimulation system for treating neurological disorders in a patient, said electrical stimulation system comprising:
    at least first, second, and third channels of electrodes; and
        an electronic control unit connected to said first and second channels of a electrodes and programmed to apply a neuromuscular pulse train pattern consisting of a plurality of cycles of a triphasic overlapping pulse train to said first and second channels of electrodes in accordance with a procedure for treating said neurological disorder; and
        an electronic control unit connected to said third channel of electrodes and programmed to apply a transcranial direct current in accordance with a procedure for treating said neurological disorder, wherein said third channel of electrodes are transcutaneous electrodes, and wherein said pulse train pattern and said transcranial direct current are programmed to be applied simultaneously.

2. The electrical stimulation system of claim 1, wherein said triphasic overlapping pulse train pattern comprises a first phase of electrical pulses applied to said first channel, a second phase of electrical pulses applied to said second channel, and a third phase of electrical pulses applied to said first channel, wherein said second phase of electrical pulses commences before termination of said first phase of electrical pulses and wherein said third phase of electrical pulses commences before termination of said second phase of electrical pulses.

3. The electrical stimulation system of claim 1, wherein said first channel comprises a first positive electrode adapted to be positioned in electrical contact with tissue of a first target body region of said patient and a first negative electrode adapted to be positioned in electrical contact with tissue of a second target body region of said patient, and
    wherein said second channel comprises a second positive electrode adapted to be positioned in electrical contact with a tissue of a third target body region of said patient and a second negative electrode adapted to be positioned in electrical contact with a tissue of a fourth target body region of said patient, and wherein said third channel comprises a third positive electrode adapted to be in transcranial electrical contact with a motor control region of said patient and a third negative electrode adapted to be in electrical contact with a tissue region contralateral to said motor control region or a neutral region of said patient.

4. The electrical stimulation system of claim 3 wherein said third negative electrode is larger in size than said third positive electrode.

5. The electrical stimulation system of claim 1 wherein said transcranial direct current is selected from the group consisting of constant, pulsed, modulated, or interferential current.

6. The electrical stimulation system of claim 1 wherein said electronic control unit connected to said first and second channels and said electronic control unit connected to said third channel are the same electronic control unit.

7. The electrical stimulation system of claim 1 wherein said electronic control unit connected to said third channel of electrodes is programmed to apply a transcranial direct current comprising a continuous or pulsed direct current with electrical pulses having a pulse duration of between 0.5 microseconds and 10 minutes.

8. The electrical stimulation system of claim 1 wherein said electronic control unit connected to said third channel of electrodes is programmed to apply a transcranial direct current of about 4 milliamps or less.

9. The electrical stimulation system of claim 1 wherein said electronic control unit connected to said third channel of electrodes is programmed to apply a transcranial direct current having a current less than 10 mA, a pulse duration between 0.5 microsecond to 10 microseconds, and a pulse frequency up to 1 MHz.

10. The electrical stimulation system of claim 1 wherein said electronic control unit connected to said first and second channels of electrodes is programmed to apply said pulse train pattern in which electrical pulses in the pattern have a pulse duration between 30 microseconds and 400 microseconds.

11. The electrical stimulation system of claim 1 wherein said electronic control unit connected to said first and second channels of electrodes is programmed to apply said pulse train pattern in which electrical pulses in the pattern have a current amplitude between 25 milliamps and 140 milliamps.

12. The electrical stimulation system of claim 1 wherein said electronic control unit connected to said first and second channels of electrodes is programmed to apply said pulse train pattern in which electrical pulses in the pattern having frequency between 4 Hz and 200 Hz and a current of no more than 1 milliamp.

13. The electrical stimulation system of claim 1, wherein said electronic control unit connected to said first and second channels of electrodes is programmed to apply a triphasic overlapping pulse train pattern comprising a first phase of electrical pulses applied to said first channel of 60 milliseconds to 120 milliseconds, a second phase of electrical pulses applied to said second channel of 60 milliseconds to 120 milliseconds, and a third phase of electrical pulses applied to said first channel of 36 milliseconds to 72 milliseconds, wherein said second phase of electrical pulses commences before termination of said first phase of electrical pulses and wherein said third phase of electrical pulses commences before termination of said second phase of electrical pulses.

14. The electrical stimulation system of claim 13, wherein said electronic control unit connected to said first and second channels of electrodes is programmed to apply a triphasic overlapping pulse train pattern wherein the individual electrical pulses in each phase is approximately 30 Hz to 100 Hz.

\* \* \* \* \*